(12) United States Patent
Kroemer et al.

(10) Patent No.: US 11,040,052 B2
(45) Date of Patent: Jun. 22, 2021

(54) METHODS AND PHARMACEUTICAL COMPOSITIONS FOR MODULATING AUTOPHAGY IN A SUBJECT IN NEED THEREOF

(71) Applicant: INSERM (INSTITUT NATIONAL DE LA SANTE ET DE LA RECHERCHE MEDICALE), Paris (FR)

(72) Inventors: Guido Kroemer, Paris (FR); Guillermo Marino, Paris (FR); Federico Pietrocola, Paris (FR)

(73) Assignee: INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 0 days.

(21) Appl. No.: 16/011,686

(22) Filed: Jun. 19, 2018

(65) Prior Publication Data

US 2019/0008884 A1    Jan. 10, 2019

Related U.S. Application Data

(63) Continuation of application No. 15/026,986, filed as application No. PCT/EP2014/071219 on Oct. 3, 2014, now abandoned.

(30) Foreign Application Priority Data

Oct. 3, 2013  (EP) .................................... 13306374

(51) Int. Cl.
| | |
|---|---|
| *A61K 31/7076* | (2006.01) |
| *A61K 31/225* | (2006.01) |
| *A61K 31/235* | (2006.01) |
| *A61K 31/4155* | (2006.01) |
| *A61K 31/7008* | (2006.01) |
| *A61K 31/4458* | (2006.01) |
| *A61K 45/06* | (2006.01) |
| *A61K 31/385* | (2006.01) |
| *A61K 31/22* | (2006.01) |
| *A61K 31/216* | (2006.01) |
| *A61K 31/194* | (2006.01) |
| *A61K 31/19* | (2006.01) |
| *A61K 31/405* | (2006.01) |

(52) U.S. Cl.
CPC .......... *A61K 31/7076* (2013.01); *A61K 31/19* (2013.01); *A61K 31/194* (2013.01); *A61K 31/216* (2013.01); *A61K 31/22* (2013.01); *A61K 31/225* (2013.01); *A61K 31/235* (2013.01); *A61K 31/385* (2013.01); *A61K 31/405* (2013.01); *A61K 31/4155* (2013.01); *A61K 31/4458* (2013.01); *A61K 31/7008* (2013.01); *A61K 45/06* (2013.01)

(58) Field of Classification Search
None
See application file for complete search history.

(56) References Cited

U.S. PATENT DOCUMENTS

| | | |
|---|---|---|
| 5,447,954 A | 9/1995 | Gribble et al. |
| 5,981,732 A | 11/1999 | Cowsert |
| 6,046,321 A | 4/2000 | Cowsert |
| 6,107,091 A | 8/2000 | Cowsert |
| 6,365,354 B1 | 4/2002 | Bennett et al. |
| 6,410,323 B1 | 6/2002 | Roberts et al. |
| 6,414,002 B1 | 7/2002 | Cheng et al. |
| 6,506,559 B1 | 1/2003 | Fire et al. |
| 6,573,099 B2 | 3/2003 | Graham |
| 6,566,131 B1 | 5/2003 | Cowsert |
| 6,566,135 B1 | 5/2003 | Watt |
| 2003/0069275 A1 | 4/2003 | Cheng et al. |
| 2003/0087935 A1 | 5/2003 | Cheng et al. |
| 2007/0142308 A1 | 6/2007 | Helmut et al. |
| 2011/0236506 A1* | 9/2011 | Schwartz ............... A61K 31/14 424/649 |
| 2013/0023587 A1 | 1/2013 | Shroeder et al. |

FOREIGN PATENT DOCUMENTS

| | | |
|---|---|---|
| WO | 93/22304 A1 | 11/1993 |
| WO | 99/32619 A1 | 7/1999 |
| WO | 01/36646 A1 | 5/2001 |
| WO | 01/68836 A2 | 9/2001 |
| WO | WO-2004100885 A2 * | 11/2004 ......... A61K 51/0491 |
| WO | 2009/008461 A1 | 1/2009 |
| WO | 2013/169956 A2 | 11/2013 |
| WO | 2013/175015 A1 | 11/2013 |

OTHER PUBLICATIONS

Guais, Adeline; et al; "Adding a combination of hydroxycitrate and lipoic acid (METABLOC™) to chemotherapy improves effectiveness against tumor development: experimental results and case report" Investigational New Drugs, 30, 200-211, 2012 (Year: 2012).*
Katan-Khaykovitch et al., "Dynamics of global histone acetylation and deacetylation in vivo: rapid restoration of normal histone acetylation status upon removal of activators and repressors." Genes Dev, 2002, 16(6):743-52.
Nakamura et al., "Biological significance of protein modifications in aging and calorie restriction", Ann N Y Acad Sci, 2010, 1197:33-9.
Rubinsztein et al., "In search of an autophagomometer." Autophagy, 2009, 5(5):585-9.
Takahashi et al., "Nucleocytosolic acetyl-coenzyme a synthetase is required for histone acetylation and global transcription." Mol Cell, 2006, 23(2):207-17.

(Continued)

*Primary Examiner* — David W Berke-Schlessel
(74) *Attorney, Agent, or Firm* — W&C IP

(57) ABSTRACT

The present invention provides novel methods for the modulation of autophagy and the treatment of autophagy-related diseases, including cancer, neurodegenerative diseases, liver diseases, muscle diseases and pancreatitis.

12 Claims, 11 Drawing Sheets

(56) References Cited

OTHER PUBLICATIONS

Figure 1:
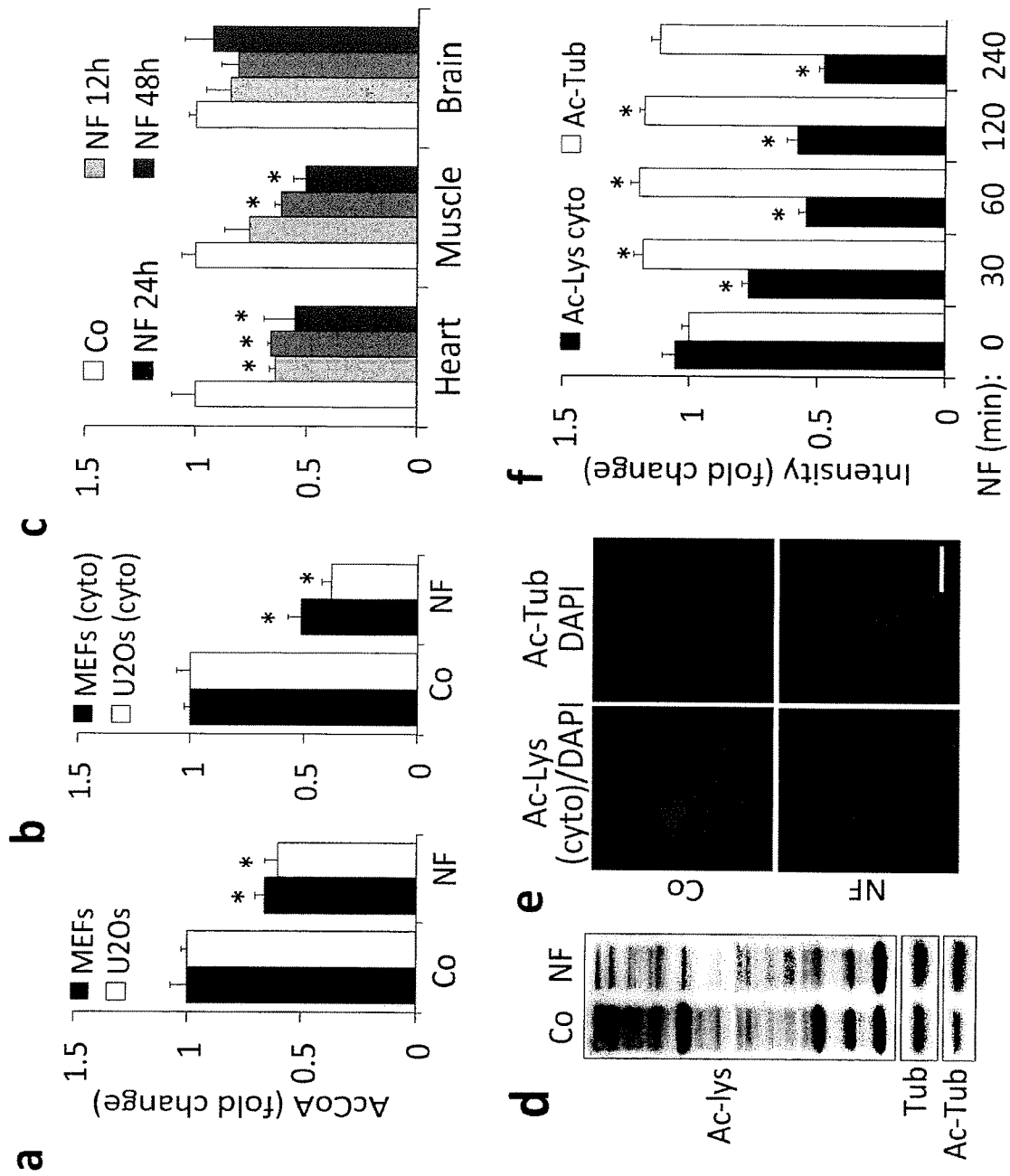

Wellen et al., "ATP-citrate lyase links cellular metabolism to histone acetylation." Science, 2009, 324(5930):1076-80.
Roche et al., "Pyruvate dehydrogenase kinase regulatory mechanisms and inhibition in treating diabetes, heart ischemia, and cancer." Cell Mol Life Sci, 2007, 64(7-8):830-49.
Jeong et al., "Transcriptional Regulation of Pyruvate Dehydrogenase Kinase." Diabetes Metab J, 2012, 36(5): 328-335.
Zacher et al., "Non-redox-active lipoate derivates disrupt cancer cell mitochondrial metabolism and are potent anticancer agents in vivo." J Mol Med (Berl), 2011, 89(11):1137-48.
Navarro et al., "Impaired oxidation of branched-chain amino acids in the medial thalamus of thiamine-deficient rats." Metab Brain Dis, 2008, 23(4):445-55.
Guo et al., "Autophagy-mediated tumor promotion." Cell, 2013, 155(6):1216-9.
Donohoe et al., "The Warburg Effect Dictates the Mechanism of Butyrate-Mediated Histone Acetylation and Cell Proliferation." Mol Cell, 2012, 48(4):612-26.
Gilbert et al., "Cytokines, obesity, and cancer: new insights on mechanisms linking obesity to cancer risk and progression." Annu Rev Med, 2013, 64:45-57.
Lin et al., "Autophagy: resetting glutamine-dependent metabolism and oxygen consumption." Autophagy, 2012, 8(10):1477-93.
Makarem et al., "Dietary fat in breast cancer survival." Annu Rev Nutr, 2013, 33:319-48.
Foster, "The role of the carnitine system in human metabolism." Ann N Y Acad Sci, 2004, 1033:1-16.
Casagrande et al., "Incidence of cancer following bariatric surgery: systematic review and meta-analysis." Obes Surg, 2014, 24(9):1499-509.
Zaugg et al., "Carnitine palmitoyltransferase 1C promotes cell survival and tumor growth under conditions of metabolic stress." Genes Dev, 2011, 25(10):1041-51.
Michaud et al., "Autophagy-dependent anticancer immune responses induced by chemotherapeutic agents in mice", Science, 2011, 334(6062):1573-7.
Lee et al., "Fasting vs dietary restriction in cellular protection and cancer treatment: from model organisms to patients." Oncogene, 2011, 30(30):3305-16.
Rubinsztein et al., "Potential therapeutic applications of autophagy." Nat Rev Drug Discov, 2007, 6(4):304-12.
Hebert et al., "Calorie restriction and SIRT3 trigger global reprogramming of the mitochondrial protein acetylome." Mol Cell, 2013, 49(1):186-99.
Klionsky et al., "Guidelines for the use and interpretation of assays for monitoring autophagy." Autophagy, 2012, 8(4):445-544.
Tee and al., "Effect of bariatric surgery on oncologic outcomes: a systematic review and meta-analysis." Surg Endosc, 2013, 27(12):4449-56.
Lowenstein et al., "Hydroxycitrate." Methods Enzymol, 1981, 72:486-97.
Watson et al., "Tricarballylate and hydroxycitrate: substrate and inhibitor of ATP: citrate oxaloacetate lyase." Arch Biochem Biophys, 1969, 135(1):209-17.
Onakpoya et al., "The Use of Garcinia Extract (Hydroxycitric Acid) as a Weight loss Supplement: A Systematic Review and Meta-Analysis of Randomised Clinical Trials." J Obes, 2011, 2011:509038.
Lee et al., "Fasting cycles retard growth of tumors and sensitize a range of cancer cell types to chemotherapy." Sci Transl Med, 2012, 4(124):124ra27.
Wellen et al., "A two-way street: reciprocal regulation of metabolism and signalling." Nat Rev Mol Cell Biol, 2012, 13(4):270-6.
Shi et al., "Acetyl-CoA induces transcription of the key G1 cyclin CLN3 to promote entry into the cell division cycle in *Saccharomyces cerevisiae*." Proc Natl Acad Sci U S A, 2013, 110(18):7318-7323.
Pietrocola et al., "Regulation of autophagy by stress-responsive transcription factors." Semin Cancer Biol, 2013, 23(5):310-22.
Lin et al., "GSK3-TIP60-ULK1 signaling pathway links growth factor deprivation to autophagy." Science, 2012, 336(6080).
Cheng et al., "Prolonged fasting reduces IGF-1/PKA to promote hematopoietic-stem-cell-based regeneration and reverse immunosuppression." Cell Stem Cell, 2014, 14(6):810-23.
Uhl et al., "Autophagy within the antigen donor cell facilitates efficient antigen cross-priming of virus-specific CD8+ T cells." Cell Death Differ, 2009, 16(7):991-1005.
Kim et al., "Differential regulation of distinct Vps34 complexes by AMPK in nutrient stress and autophagy." Cell, 2013, 152(1-2):290-303.
Kalaany et al., "Tumours with PI3K activation are resistant to dietary restriction." Nature, 2009, 458(7239):725-31.
Pellegatti et al., "Increased level of extracellular ATP at tumor sites: in vivo imaging with plasma membrane luciferase." PLoS One, 2008, 3(7):e2599.
Michaud et al., "Subversion of the chemotherapy-induced anticancer immune response by the ecto-ATPase CD39." Oncoimmunology, 2012, 1(3):393-395.
Sinclair et al., "Small-molecule allosteric activators of sirtuins." Annu Rev Pharmacol Toxicol, 2014, 54:363-80.
Harrison et al., "Rapamycin fed late in life extends lifespan in genetically heterogeneous mice." Nature, 2009, 460(7253):392-5.
Kibe et al., "Upregulation of colonic luminal polyamines produced by intestinal microbiota delays senescence in mice." Sci Rep, 2014, 4:4548.
Rabinowitz et al., "Autophagy and metabolism." Science, 2010, 330(6009):1344-8.
Campbell et al., "Pharmacokinetics, safety, and effects on exercise performance of L-arginine alpha-ketoglutarate in trained adult men." Nutrition, 2006, 22(9):872-81.
Zanchi et al., "HMB supplementation: clinical and athletic performance-related effects and mechanisms of action." Amino Acids, 2011, 40(4):1015-25.
Bowers et al., "Virtual ligand screening of the p300/CBP histone acetyltransferase: identification of a selective small molecule inhibitor." Chem Biol, 2010, 17(5):471-82.
Yeh et al., "Regulation of acetyl-coA carboxylase: properties of coA activation of acetyl-coA carboxylase." Proc Natl Acad Sci U S A, 1980, 77(6): 3351-3355.
Thompson et al., "Regulation of the p300 HAT domain via a novel activation loop." Nat Struct Mol Biol, 2004, 11(4):308-15.
Yang et al., "Reversible acetylation regulates salt-inducible kinase (SIK2) and its function in autophagy." J Biol Chem, 2013, 288(9):6227-37.
Loi et al., "Prognostic and predictive value of tumor-infiltrating lymphocytes in a phase III randomized adjuvant breast cancer trial in node-positive breast cancer comparing the addition of docetaxel to doxorubicin with doxorubicin-based chemotherapy: BIG 02-98." J Clin Oncol, 2013, 31(7):860-7.
Zitvogel et al., "Mechanism of action of conventional and targeted anticancer therapies: reinstating immunosurveillance." Immunity, 2013, 39(1):74-88.
Kepp et al., "Immunogenic cell death inducers as anticancer agents." Oncotarget, 2014, 5(14): 5190-5191.
Cao et al., "Mechanical unloading activates FoxO3 to trigger Bnip3-dependent cardiomyocyte atrophy." J Am Heart Assoc, 2013, 2(2):e000016.
Zhu et al., "Cardiac autophagy is a maladaptive response to hemodynamic stress." J Clin Invest, 2007, 117(7):1782-93.
Husnjak et al., "Ubiquitin-binding proteins: decoders of ubiquitin-mediated cellular functions." Annu Rev Biochem, 2012, 81:291-322.
Contreras et al., "Prevalence and risk factors associated with resistance-associated mutations to etravirine in a cohort of perinatally HIV-infected children." J Antimicrob Chemother, 2013, 68(10):2344-8.
Harper et al., "Branched-chain amino acid metabolism." Annu Rev Nutr, 1984, 4:409-54.
Willenborg et al., "Triggering and amplification of insulin secretion by dimethyl α-ketoglutarate, a membrane permeable α-ketoglutarate analogue." Eur J Pharmacol, 2009, 607(1-3):41-6.

(56) References Cited

OTHER PUBLICATIONS

Herzig et al., "Identification and functional expression of the mitochondrial pyruvate carrier." Science, 2012, 337(6090):93-6.
Kennedy et al., "Inhibition of carnitine palmitoyltransferase-1 in rat heart and liver by perhexiline and amiodarone." Biochem Pharmacol, 1996, 52(2):273-80.
Williams et al., "Novel targets for Huntington's disease in an mTOR-independent autophagy pathway." Nat Chem Biol, 2008, 4(5):295-305.
Pankiv, "p62/SQSTM1 binds directly to Atg8/LC3 to facilitate degradation of ubiquitinated protein aggregates by autophagy." J Biol Chem, 2007, 282(33):24131-45.
Masri et al., "Circadian acetylome reveals regulation of mitochondrial metabolic pathways." Proc Natl Acad Sci U S A, 2013, 110(9):3339-44.
Pehar et al., "SLC33A1/AT-1 protein regulates the induction of autophagy downstream of IRE1/XBP1 pathway." J Biol Chem, 2012, 287(35):29921-30.
Lin et al., "Functional dissection of lysine deacetylases reveals that HDAC1 and p300 regulate AMPK." Nature, 2012, 482(7384):251-5.
Eisenberg et al., "Induction of autophagy by spermidine promotes longevity." Nat Cell Biol, 2009, 11(11):1305-14.
Jang et al., "Nicotinamide-induced mitophagy: event mediated by high NAD+/NADH ratio and SIRT1 protein activation." J Biol Chem, 2012, 287(23):19304-14.
Canto et al., "AMPK regulates energy expenditure by modulating NAD+ metabolism and SIRT1 activity." Nature, 2009, 458(7241):1056-60.
Hou et al., "SIRT1 regulates hepatocyte lipid metabolism through activating AMP-activated protein kinase." J Biol Chem, 2008, 283(29):20015-26.
Lan et al., "SIRT1 modulation of the acetylation status, cytosolic localization, and activity of LKB1. Possible role in AMP-activated protein kinase activation." J Biol Chem, 2008, 283(41):27628-35.
Ruderman et al., "AMPK and SIRT1: a long-standing partnership?" Am J Physiol Endocrinol Metab, 2010, 298(4): E751-60.
Yang et al., "Regulation of transcription by AMP-activated protein kinase: phosphorylation of p300 blocks its interaction with nuclear receptors." J Biol Chem, 2001, 276(42):38341-4.
Pietrocola et al., "Spermidine induces autophagy by inhibiting the acetyltransferase EP300." Cell Death Differ, 2015, 22(3): 509-516.
Touzot et al., "Mechanistic target of rapamycin inhibitors in solid organ transplantation: from benchside to clinical use." Curr Opin Organ Transplant, 2012, 17(6):626-33.
Balasubramanyam et al., "Small molecule modulators of histone acetyltransferase p300." J Biol Chem, 2003, 278(21):19134-40.
Hawley et al., "The ancient drug salicylate directly activates AMP-activated protein kinase." Science, 2012, 336(6083):918-22.
Rothwell et al., "Effect of daily aspirin on risk of cancer metastasis: a study of incident cancers during randomised controlled trials." Lancet, 2012, 379(9826):1591-601.
Li et al., "Aspirin use after diagnosis but not prediagnosis improves established colorectal cancer survival: a meta-analysis." Gut, 2015, 64(9):1419-25.
Strong et al., "Nordihydroguaiaretic acid and aspirin increase lifespan of genetically heterogeneous male mice." Aging Cell, 2008, 7(5):641-50.
Fabrizio et al., "Genome-wide Screen in *Saccharomyces cerevisiae* Identifies Vacuolar Protein Sorting, Autophagy, Biosynthetic, and tRNA Methylation Genes Involved in Life Span Regulation." PLoS Genet, 2010, 6(7):e1001024.
International Search Report dated Aug. 14, 2015, in connection with corresponding international application No. PCT/EP2014/071219.
Hamon et al., "Interleukin-1beta secretion is impaired by inhibitors of the Atp binding cassette transporter, ABC1." Blood, 1997, 90(8):2911-5.
Divakaruni et al., "Thiazolidinediones are acute, specific inhibitors of the mitochondrial pyruvate carrier." Proc Natl Acad Sci U S A, 2013, 110(14):5422-7.

Wiemer et al., "The inhibition of pyruvate transport across the plasma membrane of the bloodstream form of Trypanosoma brucei and its metabolic implications." Biochem J, 1995, 312 ( Pt 2):479-84.
Dezube et al., "Tenidap inhibits replication of the human immunodeficiency virus-1 in cultured cells." J Acquir Immune Defic Syndr Hum Retrovirol, 1997, 14(1):13-7.
Skelly et al., "A distinct difference in the metabolic stimulus-response coupling pathways for regulating proinsulin biosynthesis and insulin secretion that lies at the level of a requirement for fatty acyl moieties." Biochem J, 1998, 331 (Pt 2): 553-561.
Schell et al., "The long and winding road to the mitochondrial pyruvate carrier." Cancer Metab, 2013, 1(1):6.
Hildyard et al., "Identification and characterisation of a new class of highly specific and potent inhibitors of the mitochondrial pyruvate carrier." Biochim Biophys Acta, 2005, 1707(2-3):221-30.
Hatzivassiliou et al., ATP "Citrate Lyase Inhibition Can Suppress Tumor Cell GrowthCancer Cell." Oct. 2005;8(4):311-21.
Mizushima et al., "Autophagy: renovation of cells and tissues." Cell, 2011, 147(4):728-41.
Kroemer et al., "Autophagy and the integrated stress response." Mol Cell, 2010, 40(2):280-93.
Ma et al., "Anticancer chemotherapy-induced intratumoral recruitment and differentiation of antigen-presenting cells." Immunity, 2013, 38(4):729-41.
Marino et al., "Autophagy for tissue homeostasis and neuroprotection." Curr Opin Cell Biol. 2011, 23(2):198-206.
Lopez-Otin et al., "The hallmarks of aging." Cell, 2013, 153(6):1194-217.
Rubisztein et al., "Autophagy and aging." Cell, 2011, 146(5):682-95.
Madeo et al., "Caloric restriction mimetics: towards a molecular definition." Nat Rev Drug Discov, 2014, 13(10):727-40.
Choi et al., "Autophagy in human health and disease." N Engl J Med, 2013, 368(7):651-62.
Levine et al., "Autophagy in the pathogenesis of disease." Cell, 2008, 132(1):27-42.
Marino et al., "Regulation of autophagy by cytosolic acetyl-coenzyme A." Mol Cell, 2014, 53(5):710-25.
Morselli et al., "Spermidine and resveratrol induce autophagy by distinct pathways converging on the acetylproteome." J Cell Biol, 2011, 192(4): 615-629.
Tasdemir et al., "Regulation of autophagy by cytoplasmic p53." Nat Cell Biol, 2008, 10(6):676-87.
Crighton et al., "DRAM, a p53-induced modulator of autophagy, is critical for apoptosis." Cell, 2006, 126(1):121-34.
Settembre et al., "TFEB links autophagy to lysosomal biogenesis." Science, 2011, 332(6036):1429-33.
Warr et al., "FOXO3A directs a protective autophagy program in haematopoietic stem cells." Nature, 2013, 494(7437):323-7.
Behrends et al., "Network organization of the human autophagy system." Nature. 2010, 466(7302):68-76.
Shi et al., "TRAF6 and A20 regulate lysine 63-linked ubiquitination of Beclin-1 to control TLR4-induced autophagy." Sci Signal, 2010, 3(123):ra42.
Rao et al., "A dual role for autophagy in a murine model of lung cancer." Nat Commun, 2014, 5:3056.
Banreti et al., "The emerging role of acetylation in the regulation of autophagy." Autophagy, 2013, 9(6): 819-829.
Lee et al., "A role for the NAD-dependent deacetylase Sirt1 in the regulation of autophagy." Proc Natl Acad Sci U S A, 2008, 105(9):3374-9.
Lee et al., "Regulation of autophagy by the p300 acetyltransferase." J Biol Chem, 2009, 284(10):6322-8.
Yi et al., "Function and molecular mechanism of acetylation in autophagy regulation." Science, 2012, 336(6080):474-7.
Brunet et al., "Stress-Dependent Regulation of FOXO Transcription Factors by the SIRT1 Deacetylase." Science, 2004, 303(5666):2011-5.
Ko et al., "Autophagy inhibition radiosensitizes in vitro, yet reduces radioresponses in vivo due to deficient immunogenic signalling." Cell Death Differ, 2014, 21(1): 92-99.

(56) References Cited

OTHER PUBLICATIONS

Guo et al., "Activated Ras requires autophagy to maintain oxidative metabolism and tumorigenesis." Genes Dev, 2011, 25(5):460-70.
Schwartz et al., "A combination of alpha lipoic acid and calcium hydroxycitrate is efficient against mouse cancer models: preliminary results." Oncol Rep. 2010;23(5):1407-1416.
Schwartz et al., "Tumor regression with a combination of drugs interfering with the tumor metabolism: efficacy of hydroxycitrate, lipoic acid and capsaicin." Invest New Drugs. 2013;31(2):256-264.
Abolhassani al., "Screening of well-established drugs targeting cancer metabolism: reproducibility of the efficacy of a highly effective drug combination in mice." Invest New Drugs. 2012;30(4):1331-1342.
Baronzio et al., "Early clinical and toxicological results of a combination of natural glycolysis inhibitors (METABLOC™) on cancer patients." Biomedical Research 2012; 23: SI 219-223.
Burmer et al., "Mutations in the KRAS2 oncogene during progressive stages of human colon carcinoma." Proc Natl Acad Sci U S A, 1989, 86(7): 2403-2407.
Almoguera et al., "Most human carcinomas of the exocrine pancreas contain mutant c-K-ras genes." Cell, 1988, 53(4):549-54.
Tam et al., "Distinct Epidermal Growth Factor Receptor and KRAS Mutation Patterns in Non-Small Cell Lung Cancer Patients with Different Tobacco Exposure and Clinicopathologic Features." Clin Cancer Res, 2006, 12(5):1647-53.
Ladoire et al., "Immunohistochemical detection of cytoplasmic LC3 puncta in human cancer specimens." Autophagy, 2012, 8(8):1175-84.
Marino et al., "Autophagy is essential for mouse sense of balance." J Clin Invest, 2010, 120(7):2331-44.
Choudhary et al., "Lysine acetylation targets protein complexes and co-regulates major cellular functions." Science, 2009, 325(5942):834-40.
Mizushima et al., "In vivo analysis of autophagy in response to nutrient starvation using transgenic mice expressing a fluorescent autophagosome marker." Mol Biol Cell, 2004, 15(3):1101-11.
Geeraert et al., "Starvation-induced hyperacetylation of tubulin is required for the stimulation of autophagy by nutrient deprivation." J Biol Chem, 2010, 285(31):24184-94.
Hamai et al., "New targets for acetylation in autophagy." Sci Signal, 2012, 5(231):pe29.
Lee et al., "HDAC6 controls autophagosome maturation essential for ubiquitin-selective quality-control autophagy." EMBO J, 2010, 29(5): 969-980.
Pietrocola et al., "Pro-autophagic polyphenols reduce the acetylation of cytoplasmic proteins." Cell Cycle, 2012, 11(20): 3851-3860.
Hassig et al., "Histone Deacetylase Activity Is Required for Full Transcriptional Repression by mSin3A." Cell, 1997, 89(3):341-7.
Zu XY et al. ATP citrate lyase inhibitors as novel cancer therapeutic agents. Recent Pat Anticancer Drug Discov. May 1, 2012;7(2):154-67.

* cited by examiner

METHODS AND PHARMACEUTICAL COMPOSITIONS FOR MODULATING AUTOPHAGY IN A SUBJECT IN NEED THEREOF

CROSS-REFERENCE TO RELATED APPLICATIONS

This application is a continuation application of U.S. Ser. No. 15/026,986 filed Apr. 3, 2016, which itself was a Rule 371 filing from International Application PCT/EP2014/071219 filed Oct. 3, 2013, and that application claimed priority to European Application 13306374.3 filed Oct. 3, 2013.

FIELD OF THE INVENTION

The present inventions relates to methods and pharmaceutical compositions for modulating (i.e. inducing or inhibiting) autophagy in a subject in need thereof.

BACKGROUND OF THE INVENTION

Macroautophagy ("autophagy") involves the highly regulated sequestration of cytoplasmic organelles or portions of the cytosol in double-membrane vesicles, called autophagosomes, which fuse with lysosomes resulting in the degradation of the inner autophagosomal membrane and luminal content (Mizushima and Komatsu, 2011). Autophagy plays an essential role in cellular adaptation to multiple types of stress, recycling of superfluous or damaged cellular material, quality control of organelles, removal of protein aggregates, and destruction of intracellular pathogens (Kroemer et al., 2010). Disabled or insufficient autophagy participates in the pathogenesis of multiple infectious diseases, autoimmune or autoinflammatory states, malignant transformation, neuro- or myodegenerative maladies, and aging (Fabrizio et al., 2010; Mariño et al., 2011). In most instances, autophagy aims at reestablishing the status quo ante, meaning that it plays a fundamental role in the homeostatic regulation of metabolism, the removal of noxious cellular components, such as protein aggregates or dysfunctional organelles, as well as in the renewal of the cellular cytoplasm, resulting in cellular repair and rejuvenation (López-Otín, 2013; Rubinsztein et al., 2011). Although autophagy plays a major role in antagonizing degenerative processes and unwarranted cell death, its excessive induction may result in maladaptive tissue remodeling (Cao et al., 2013; Choi et al., 2013; Levine and Kroemer, 2008; Zhu et al., 2007).

Autophagy can be induced by a plethora of cell-extrinsic and cell-intrinsic stressors, in a biphasic process. The rapid phase of autophagy induction, which occurs on a time scale of minutes to hours, does not require de novo synthesis of macromolecules and relies on post-transcriptional regulators (Morsclli et al., 2011; Tasdemir et al., 2008). In contrast, more protracted autophagic responses rely the execution of precise transcriptional programs (Crighton et al., 2006; Settembre et al., 2011; Warr et al., 2013). Protein post-transcriptional modifications play a major role in the rapid adaptation of the autophagic cascade. Thus, the autophagic pathway is regulated by multiple (de)phosphorylation steps, hence involving kinases and phosphatases that act on a diverse array of proteins and lipids. Multiple components of the 'core machinery' of autophagy are either kinases (such as the protein kinases ATG1 and mTOR or the lipid kinase Vps34) or kinase substrates (Behrends et al., 2010).

Another post-translational modification known that plays a major role in the regulation of autophagy is ubiquitylation. Thus, Bcclin 1, which is an obligate co-activator of Vps34, is ubiquitylated in the course of autophagy induction (Shi and Kehrl, 2010), and autophagic substrates are typically 'marked' by ubiquitylation for recognition by STQM1-like pattern recognition receptors, which target the autophagic cargo to autophagosomes (Husnjak and Dikic, 2012). Protein acetylation also has a major impact on autophagic regulation. Multiple components of the 'core machinery' of autophagy have been shown to undergo changes in their acetylation status (Banreti et al., 2013; Lee et al., 2008; Lee and Finkel, 2009; Morselli et al., 2011; Yi et al., 2012), and similarly core regulators of autophagy such as the transcription factors p53 and FOXP3 can be regulated by acetylation (Brunet et al., 2004; Contreras et al., 2013).

Multiple links between autophagy and metabolism exist. Autophagy can supply substrates to replenish TCA cycle intermediates through anaplerotic reactions to sustain mitochondrial function in stress and starvation (Guo et al., 2011). Metabolic perturbation, in particular amino acid, serum or glucose deprivation, can induce autophagy, and potent energy sensors including AMP-dependent protein kinase (AMPK), the mammalian target of rapamycin (mTOR) complex 1 (mTORC1), and the NADH-dependent dcacctylascs of the sirtuin family control autophagy (Kroemer et al., 2010). Thus, decreases in intracellular amino acids, ATP and NADH give rise to mTORC1 inhibition, AMPK stimulation and sirtuin1 activation, respectively, thereby stimulating the induction of autophagy via intersecting pathways (Kroemer et al., 2010).

SUMMARY OF THE INVENTION

The present invention provides novel methods for the modulation of autophagy and the treatment of autophagy-related diseases, including cancer, neurodegenerative diseases, liver diseases, muscle diseases and pancreatitis. In particular, the present invention is defined by the claims.

DETAILED DESCRIPTION OF THE INVENTION

Here, the present invention is based on the unexpected finding that acetyl CoA (AcCoA) is yet another metabolite that plays a cardinal role in the regulation of starvation-induced autophagy. Acetyl-coenzyme A (AcCoA) is a major integrator of the nutritional status at the crossroad of fat, sugar and protein catabolism. At variance with kinases, which operate over a large concentration range of the phospho donor ATP, the activity of acetyltransferases is influenced by the concentration of AcCoA, the donor of acetyl groups. Here the inventors show that nutrient starvation causes rapid depletion of AcCoA, preceding that of ATP or NADH. AcCoA depletion entailed the commensurate reduction in the overall acetylation of cytoplasmic proteins, as well as the induction of autophagy, a homeostatic process of self-digestion. Multiple distinct manipulations designed to increase or reduce cytosolic AcCoA led to the suppression or induction of autophagy, respectively, either in cultured human cells, mice or yeast. Moreover, maintenance of high AcCoA levels inhibited maladaptive autophagy in a model of cardiac pressure overload, while depletion of AcCoA reproduced the beneficial effects of starvation on cancer therapy. Altogether, the results indicate that cytosolic AcCoA levels function as a central metabolic regulator of autophagy, thus delineating pharmacological strategies that, by targeting AcCoA, may allow for the therapeutic manipulation of autophagy. Accordingly, the present invention provides novel methods for the modulation of autophagy and the treatment of autophagy-related diseases, including cancer, neurodegenerative diseases, liver diseases, muscle diseases and pancreatitis.

Methods of Inducing Autophagy:

In some embodiments, the invention relates to methods of inducing autophagy in a cell comprising contacting the cell with at least one AcCoA depleting agent.

In some embodiments, the invention relates to methods of inducing autophagy in a subject comprising administering the subject with an amount of at least one AcCoA depleting agent.

As used herein, the term "subject" means a human or non-human animal selected for treatment or therapy.

In some embodiments, and as described herein after, the subject suffers from a disease selected from the group consisting of cancer diseases, neurodegenerative diseases, cardiovascular diseases such as ischemia, infectious diseases, auto-immune disease and/or inflammatory diseases such as pancreatitis, proteinopathies, metabolic diseases such as obesity and insulin resistance.

As used herein the term "AcCoA" has its general meaning in the art and refers to acetyl-coenzyme A.

As used herein, the term "agent" refers to an entity capable of having a desired biological effect on a subject or cell. Examples of agents include small molecules {e.g., drugs), antibodies, peptides, proteins {e.g., cytokines, hormones, soluble receptors and nonspecific-proteins), oligonucleotides (e.g., peptide-coding DNA and RNA, double-stranded RNA and antisense RNA) and peptidomimetics.

As used herein the term "AcCoA depleting agent" refers to any agent that is able to directly or indirectly deplete the level of AcCoA in a cell, more particularly to deplete the cytosolic level of AcCoA in a cell. In particular, the AcCoA depleting agent is selected from the group consisting of inhibitors of inhibitors of the glycolytic or lipolytic pathways, inhibitors of the mitochondrial export of AcCoA, or inhibitors of cytosolic AcCoA synthase.

As used herein, the term "inhibitor" any compound or treatment that reduces or blocks the activity of the target protein (e.g. an enzyme). The term also includes inhibitors of the expression of the target protein. As used herein, the phrase "inhibiting the activity" of a gene product refers to a decrease in a particular activity associated with the gene product. Examples of inhibited activity include, but are not limited to, decreased translation of mRNA, decreased signal transduction by polypeptides or proteins and decreased catalysis by enzymes. Inhibition of activity can occur, for example, through a reduced amount of activity performed by individual gene products, through a decreased number of gene products performing the activity, or a through any combination thereof. If a gene product enhances a biological process {e.g. autophagy), "inhibiting the activity" of such a gene product will generally inhibit the process. Conversely, if a gene product functions as an inhibitor of a biological process, "inhibiting the activity" of such a gene product will generally enhance the process.

In some embodiments, the AcCoA depleting agent is an inhibitor of mitochondrial pyruvate carrier complex (MPC). An example of a pharmacological inhibitor includes alpha-cyanocinnamate derivative UK5099 (2-Cyano-3-(1-phenyl-1H-indol-3-yl)-2-propenoic acid).

In some embodiments, the AcCoA depleting agent is an inhibitor of mitochondrial carnitine palmitoytransferase-1 (CTP1). An example of a pharmacological inhibitor includes perhexiline (PHX). In some embodiments, the inhibitor is an inhibitor of CTP1c expression.

In some embodiment, the AcCoA depleting agent is an inhibitor of mitochondrial citrate carrier (CiC). An example of a pharmacological inhibitor includes benzenetricarboxylate (BTC).

In some embodiment, the AcCoA depleting agent is an inhibitor of ATP-citratre lyase (ACLY). An example of a pharmacological inhibitor includes hydroxycitrate. Other examples include this described in WO1993022304A1, U.S. Pat. No. 5,447,954, U.S. Pat. No. 6,414,002 US20030087935, and US20030069275. Other known inhibitors include (R,S)—S-(3,4-dicarboxy-3-hydroxy-3-methyl-butyl)-CoA, S-carboxymethyl-CoA and SB-204990 ((3R,5S)-rel-5-[6-(2,4-Dichlorophenyl)hexyl]tetrahydro-3-hydroxy-2-oxo-3-furanacetic acid) and BMS-303141 (3 5-Dichloro-2-hydroxy-N-(4-methoxy[1,1'-biphenyl]-3-yl)-benzenesulfonamide).

In some embodiments, the AcCoA depleting agent is an EP300 acetyltransferase inhibitor. As used herein the term EP300 refers to the "E1A binding protein p300" protein which functions as histone acetyltransferase that regulates transcription via chromatin remodeling and is important in the processes of cell proliferation and differentiation. Examples of EP300 acetyltransferase inhibitors include but are not limited to aspirin, salicylate and C646 which has the following formula:

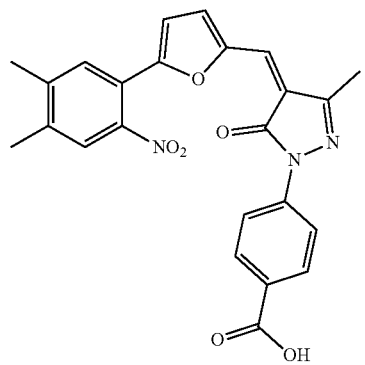

In some embodiments, the AcCoA depleting agent is an inhibitor of acyl-CoA synthetase short-chain family member 2 (ACCS2).

An "inhibitor of expression" refers to a natural or synthetic compound that has a biological effect to inhibit the expression of a gene.

In a preferred embodiment of the invention, said inhibitor of gene expression is a siRNA, an antisense oligonucleotide or a ribozyme.

Inhibitors of gene expression for use in the present invention may be based on antisense oligonucleotide constructs. Anti-sense oligonucleotides, including anti-sense RNA molecules and anti-sense DNA molecules, would act to directly block the translation of the targeted mRNA by binding thereto and thus preventing protein translation or increasing mRNA degradation, thus decreasing the level of the targeted protein, and thus activity, in a cell. For example, antisense oligonucleotides of at least about 15 bases and complementary to unique regions of the mRNA transcript sequence encoding the target protein can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as inhibitors of gene expression for use in the present invention. Gene expression can be reduced by contacting the tumor, subject or cell with a small double stranded RNA (dsRNA), or a vector or construct causing the production of a small double stranded RNA, such that gene expression is specifically inhibited (i.e. RNA interference or RNAi). Methods for selecting an appropriate dsRNA or dsRNA-encoding vector are well known in the art for genes whose sequence is known (e.g. see Tuschi, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

Ribozymes can also function as inhibitors of gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of the targeted mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors of gene expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in KRIEGLER (A Laboratory Manual," W.H. Freeman C.O., New York, 1990) and in MURRY ("Methods in Molecular Biology," vol. 7, Humana Press, Inc., Cliffton, N.J., 1991).

Preferred viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hematopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g., SANBROOK et al., "Molecular Cloning: A Laboratory Manual," Second Edition, Cold Spring Harbor Laboratory Press, 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBluescript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

Methods of Inhibiting Autophagy:

In some embodiments, the invention relates to methods of inhibiting autophagy in a cell comprising contacting the cell with an amount of AcCoA and/or at least one AcCoA replenishing agent.

In some embodiments, the invention relates to methods of inhibiting autophagy in a subject comprising administering the subject with an amount of AcCoA and or at least one AcCoA replenishing agent.

In some embodiments, the subject suffers from a disease selected from the group consisting of cardiovascular diseases such as surgical thoracic constriction (TAC), infectious diseases such as bacterial infections, cancer such as cancer with an advanced stage (stage II or IV), pulmonary diseases such as chronic obstructive pulmonary disease (COPD), hepatic diseases such as liver fibrosis, lysosomal impairment diseases, such as Danon disease, X-linked myopathy with excessive autophagy (XMEA), Glycogen Storage Type II (GSDII), Pompe disease, muscular diseases such as muscular atrophy.

As used herein the term "AcCoA replenishing agent" refers to any agent that is able to maintain or increase the level of AcCoA in a cell. Examples of AcCoA-replenishing agent include but are not limited to dicholoroacetate (DCA), lipoic acid (LA), ketoisocaproic acid (KIC), butyrate or dimethy-α-ketoglutarate (DMKG).

Examples of Applications for Using the Methods of the Invention

The methods of the invention may find various applications such as described herein after.

Autophagy and Cancer:

It has been established that autophagy plays a dual role according to cancer stage. There is a consensus in indicating that autophagy represents a tumour suppressor mechanism in the tumour initiation, most likely due to its ability to remove damaged organelles (especially mitochondria) and to control the levels of the oncogenic protein p62, which in turn may represent a potential source of ROS and genotoxic stress. Thus, AcCoA depleting agents may represent a valid strategy for the oncoprevention (i.e. prevention of cancer).

On the contrary, autophagy seems to be indispensable for tumour progression, providing the tumours with building blocks and energy for its increased metabolic requirements. Therapies based on well-known autophagy inhibitors (3-Methyladenine, Chloroquine, BafilomycinA1) have already started but are limited by their side effects. The modulation of the tumours' metabolic environment by the administration of AcCoA replenishing agents (KIC, DCA, DMKG) alone or in combination with chemotherapeutic drugs may lead to a suppression of basal and starvation-induced autophagy, thus sensitizing tumour cells to the death Although the underlying mechanism has not been characterized yet, it has been shown that pre-chemotherapy starvation (the most potent autophagy-inducing physiological stimulus able to systemically induce autophagy) significantly increased treatment efficiency and limits the tumour growth. Furthermore, it has been demonstrated that tumours with PI3K over-activation are resistant to dietary restriction, suggesting an important role for autophagy in the chemiosensitization process. This invention might lead to a less aggressive and equivalently effective treatment based on the punctual administration of an AcCoA depleting agent.

In particular, the present invention relates to a method for treating a cancer in a subject in need thereof comprising administering the subject with a therapeutically effective amount of AcCoA depleting agent and a therapeutically effective amount of a chemotherapeutic agent wherein the AcCoA depleting agent is administered prior to the chemotherapeutic agent. In some embodiments, the AcCoA depleting agent is administered 12; 13; 14; 15; 16; 17; 18; 19; 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; 50; 51; 52; 53; 54; 55; 56 h before the administration of the chemotherapeutic agent.

As used herein, the term "cancer" has its general meaning in the art and includes, but is not limited to, solid tumors and blood borne tumors. The term cancer includes diseases of the skin, tissues, organs, bone, cartilage, blood and vessels. The term "cancer" further encompasses both primary and metastatic cancers. Examples of cancers that may treated by methods and compositions of the invention include, but are not limited to, cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma; malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis *coli*; solid carcinoma; carcinoid tumor, malignant; branchioloalveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous; adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; Sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; syno vial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In some embodiments, the cancer is a KRAS mutated cancer. As used herein, "KRAS" refers to v-Ki-ras2 Kirsten rat sarcoma viral oncogene homo log. KRAS is also known in the art as NS3, KRAS1, KRAS2, RASK2, KI-RAS, C-K-RAS, K-RAS2A, K-RAS2B, K-RAS4A and K-RAS4B. This gene, a Kirsten ras oncogene homolog from the mammalian ras gene family, encodes a protein that is a member of the small GTPase superfamily. A single amino acid substitution can be responsible for an activating mutation. The transforming protein that results can be implicated in various malignancies, including lung cancer, colon cancer and pancreas cancer. KRAS mutations are well known in the art and are frequently found in neoplasms include those at exon 1 (codons 12 and 13) and exon 2 (codon 61) (e.g., the 34A, 34C, 34T, 35A, 35C, 35T or 38A mutations). Other examples of KRAS mutations include, but are not limited to, G12C, G12D, G13D, G12R, G12S, and G12V. Somatic KRAS mutations are found at high rates in leukemias, colorectal cancer (Burmer et al. Proc. Natl. Acad. Sci. 1989 86: 2403-7), pancreatic cancer (Almoguera et al. Cell 1988 53: 549-54) and lung cancer (Tam et al. Clin. Cancer Res. 2006 12: 1647-53). Methods for identifying KRAS mutations are well known in the art and are commercially available (e.g. In Therascreen (Qiagen) assay, Taqman® Mutation Detection Assays powered by castPCR™ technology (Life Technologies)).

In some embodiments, the cancer is an autophagy competent cancer. As used herein the term "autophagy competent cancer" denotes a cancer wherein autophagy could occur. In some embodiments, an ATG5 or ATG7 deficiency is not detected. In the context of the invention, the term "ATG5 or ATG7 deficiency" denotes that the timour cells of the subject or a part thereof have an ATG5 or ATG7 dysfunction, a low or a null expression of ATG5 or ATG7 gene. Said deficiency may typically result from a mutation in ATG5 or ATG7 gene so that the pre-ARNm is degraded through the NMD (non sense mediated decay) system. Said deficiency may also typically result from a mutation so that the protein is misfolded and degraded through the proteasome. Said deficiency may also result from a loss of function mutation leading to a dysfunction of the protein. Said deficiency may also result from an epigenetic control of gene expression (e.g. methylation) so that the gene is less expressed in the cells of the subject. Said deficiency may also result from a repression of the ATG5 or ATG7 gene induce by a particular signalling pathway. Said deficiency may also result from a mutation in a nucleotide sequence that control the expression of ATG5 or ATG7 gene.

In some embodiments, the AcCoA depleting agents of the present invention are particularly suitable for reducing Treg infiltration into the tumor.

In some embodiments, the invention relates to a kit-of-parts comprising at least one AcCoA depleting agent and at least one chemotherapeutic agent for use in the treatment of cancer.

Chemotherapeutic include, but are not limited to alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII; dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmo fur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demccolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-1 1); topoisomerase inhibitor RFS 2000; difluoromethylomithine (DMFO); retinoids such as retinoic acid; capecitabine; and pharmaceutically acceptable salts, acids or derivatives of any of the above.

Autophagy and Infectious Diseases

Autophagic process actively participates in a multi-pronged defence against microorganisms, contributing to their elimination either via the selective delivery of microorganisms to degradative lysosomes (a process referred to as xenophagy) or via the delivery of microbial nucleic acids to endolysosomal compartment (with subsequent activation of innate and adaptive immunity).

Clinically relevant pathogens are degraded in vitro by xenophagy; among these, there are bacteria such as group A *Streptococcus pyogenes, Mycobacterium tuberculosis, Shigella flexneri, Salmonella enterica, Listeria monocytogenes*; viruses such as herpes simplex virus type 1 (HSV 1) and parasites such as *Toxoplasma gondii*. Moreover in vivo evidences showed that autophagy genes have a protective role against numerous pathogens, including *L. monocytogenes, M. tuberculosis, S. enterica, T. gondii*, HSV 1. It has been recently shown that the infection mediated by pathogens like *Shigella* and *Salmonella* triggers an aminoacids starvation response eventually leading to the elimination of these pathogens via autophagy. Here use of AcCoA depleting agents for triggering a pro-autophagic and anti microbial response against bacterial and virus infection may be suitable.

On the other side, some pathogens can exploit the autophagy machinery for spreading from cell to cell (i.e. *Brucella abortus*) or for enhancing viral replication (i.e. HBV); in this case, the inhibition of basal autophagy through AcCoA replenishing agents may suppress basal autophagy limiting the infective process.

Autophagy and Neurodegenerative Diseases:

Neurodegenerative diseases (i.e Alzheimer disease, Parkinson disease, Huntington disease) are a series of different age-dependent or genetic-dependent pathologies, characterized by progressive neuronal death as consequence of accumulation of aggregates of misfolded proteins, damaged organelles, impaired function of cellular clearence mechanisms. Being autophagy a physiological mechanism dedicated to the degradation of potentially harmful and aggregation-prone long-lived proteins, as well as of the recycle of damaged organelles, it is considered as a protective factor against neuronal cell death.

In the context of this invention, the treatment of patients with AcCoA depleting agents may results in an improvement of the cellular clearance functions and in an amelioration of the symptomatology of different diseases.

For example, Huntington disease is a pathology characterized by the progressive expansion of poly-glutamine tail of the protein huntingtin, resulting in its intra-neuronal aggregation. Huntingtin has been demonstrated to be a specific target of the autophagic pathway, and the increase in basal autophagy by administration of one of the AcCoa depleting agents can reduce the rate of neuronal death.

In two forms of familiar Parkinson disease, recessive mutations in two genes encoding for PINK1 and PARK2, involved in mitophagy, partially account for the pathogenesis of this disease and may render the patients suitable for treatment with AcCoA depleting agents.

In the same way, autophagy induction may contribute to the removal of alpha-synuclein aggregates (Lewi bodies), responsible for the pathogenesis of sporadic forms of Parkinson disease, most likely due to a saturation of the autophagic system.

As used herein, the phrases "neurodegenerative disorder" and "neurodegenerative disease" refers to a wide range of diseases and/or disorders of the central and peripheral nervous system. Examples of neurodegenerative diseases include but are not limited to Adrenal Leukodystrophy, alcoholism, Alexander's disease, Alper's disease, Alzheimer's disease, Amyotrophic lateral sclerosis, ataxia telangiectasia, Batten disease, bovine spongiform encephalopathy, Canavan disease, cerebral palsy, cockayne syndrome, corticobasal degeneration, Creutzfeldt-Jakob disease, familial fatal insomnia, frontotemporal lobar degeneration, Huntington's disease, HIV-associated dementia, Kennedy's disease, Krabbe's disease, Lewy body dementia, neuroborreliosis, Machado-Joseph disease, multiple system atrophy, multiple sclerosis, narcolepsy, Niemann Pick disease, Parkinson's disease, Pelizaeus-Merzbacher disease, Pick's disease, primary lateral sclerosis, prion diseases, progressive supranuclear palsy, Refsum's disease, Sandhoff disease, Schilder's disease, subacute combined degeneration of spinal cord secondary to pernicious anaemia, Spielmeyer-Vogt-Sjogren-Batten disease, spinocerebellar ataxia, spinal muscular atrophy, Steele-Richardson-Olszewski disease, Tabes dorsalis, toxic encephalopathy and combinations of these diseases.

Autophagy and Cardiovascular Diseases:

It is accepted that basal autophagy is necessary for the survival and the function of cardiomyocytes. However, a consensus is emerging about the notion that autophagy can either ameliorate the symptomatology or contribute to the progression of disease depending on the context and amplitude of induction. In this context, the treatment with AcCoa depleting (HC,UK-5099,BTC,PHX) and/or replenishing agents (KIC,DCA,DMKG), acting in a short-term range of time, can finely modulate autophagic process thus allowing an adaptation to differential conditions.

Cardiac pressure overload induces autophagy activation, being this autophagic response detrimental. Hence, we propose the administration of AcCoA replenishing agents for the reduction of the after-load stress.

In conditions of mild ischemic stress, a situation mimicking nutrient starvation, autophagy induction (in the context of this invention related to the administration of AcCoa depleting agents) is beneficial. On the other side, ischemia-reperfusion-induced autophagy is considered detrimental for the function and the survival of cardiomyocytes. In the context of ischemia-reperfusion, the administration of AcCoA replenishing agents may result determinant for cardiomyocytes survival.

Autophagy and Pulmonary Diseases:

An increased autophagy was associated with the pathogenesis of chronic obstructive pulmonary disease (COPD) following to long-term exposure to cigarettes smokes, thus rendering patients affected by this pathology suitable for the administration of an AcCoA replenishing agents (i.e. KIC, DCA, DMKG).

Mutations in the protein al-antitrypsin causes pulmonary emphysema, a disease characterized by the accumulation of the aggregated form of the mutant proteins. As for others proteinopathy, autophagy induction by the administration of AcCoA depleting agents (e.g. HC, UK-5099) might ameliorate the symptoms.

A recent pre-clinical study has found as a consequence of a dysfunctional aggrephagy the pathogenicity of cystic fibrosis, due to an impaired clearance of aggregates of the mutant CTFR. Induction of autophagy mediated by administration of an AcCoA depleting agent may represent a suitable strategy.

Autophagy and Muscular Diseases

Skeletal muscle is an organ whose homeostasis is achieved through the cooperation of multiple signalling pathways, most of them controlling protein turnover and removal of damaged organelles. Autophagy, mainly through the degradation of long-lived proteins is one of the major determinants for muscular function.

Atrophy (and atrophy related pathologies, such as glycogen storage disease type II) is a pathology characterized by hyperactivation of the proteolytic and autophagic pathways, eventually leading to a excessive loss of contractile proteins and organelles and to a progressive dysfunction of the muscular performance. Here this invention relates to the administration of an AcCoA replenishing agents for the limitation of the autophagic intensity. More particularly, the Leucine metabolites KIC would represent a treatment organ-specific, given the abundance of this metabolite in the skeletal muscles.

Autophagy and Hepatic Diseases:

The potential impact of autophagy in vivo was discovered from liver studies and this underlines the important role played by autophagy in the physiology of this organ. NAFLD represents one of the most recurrent and severe pathologies, especially among obese and diabetic patients, yet a specific therapy is far from being available. NAFLD is defined as the accumulation of fat in the liver, but not as secondary consequence of alcohol consumption. The pro-autophagic potential of AcCoA depleting agents can be used as therapy for NAFLD for different causes: selective degradation of TG droplets (lipophagy), suppression of lipogenetic pathways (i.e. inhibition of Citrate export from the mitochondria by BTC). Conversely, autophagy inducer Perhexiline can play an adaptive and protective role in ALD, conferring to hepatocyte protection after ethanol intoxication and inhibiting adipocytes differentiation.

Liver fibrosis, described as a condition where extracellular matrix progressively replaces the hepatic parenchyma, represents the final stage of chronic liver disease; the deposition of scar tissue has been discovered to be carried out by quiescent hepatic stellate cells (HSC) activated to myofibroblasts. Besides inflammatory stimuli, autophagy is thought to play a role in the HSC differentiation by favouring the loss of lipid droplets in the HSC cytoplasms. Targeting autophagy by AcCoA replenishing agents can be an alternative therapy for the development of the cirrhotic phenotype.

Autophagy and Autoimmune and/or Inflammatory Diseases:

Pancreatitis is an inflammatory disease of the exocrine pancreas, culminating in a massive necrotic cell death of acinar cells. Although the mechanisms promoting this pathology are still unclear, there is a consensus on the notion that autophagy is impaired in this pathological process. Acinar cells are characterized by large autophagosomes unable to become autophagolysosomes, mainly due to the depletion of lysosomal proteins (i.e. LAMP2). Furthermore, it has been recently shown that loss of Ikka inhibits autophagy flux and promotes the formation of p62-positive protein aggregates, thus contributing to the initiation of the disease. In addition, during the acute phase of the disease, a selective autophagy process called 'zymophagy' prevents acinar cells death through degradation of harmful activated zymogen granules. AcCoA depleting agents such as the hydroxycitric acid can be tested for their capacity to trigger zimophagy. Moreover, these agents, alone or in combination with a lysosomal-targeted therapy, can be suitable for ameliorating the symptomatology of the disease by restoring a normal autophagic flux.

"Autoimmune and/or inflammatory diseases" in the context of the present invention, relates to diseases arising from an overactive immune response of the body against substances and tissues normally present in the body. In other words, the body actually attacks its own cells or components. The immune system mistakes some part of the body as a pathogen and attacks it. This may be restricted to certain organs (e.g. in thyroiditis) or involve a particular tissue in different places (e.g. Goodpasture's disease which may affect the basement membrane in both the lung and the kidney). The treatment of autoimmune and/or inflammatory diseases is typically with immunosuppression medication which decreases the immune response. Exemple of autoimmune and/or inflammatory disease include but are not limited to sarcoidosis, Ankylosing Spondylitis, Crohns Disease (one of two types of idiopathic inflammatory bowel disease "IBD"), Dermatomyositis, Diabetes mellitus type 1, Goodpasture's syndrome, Graves' disease, Guillain-Barré syndrome (GBS), Hashimoto's disease, Hidradenitis suppurativa, Idiopathic thrombocytopenic purpura, systemic Lupus erythematosus, Mixed Connective Tissue Disease, Multiple Sclerosis Myasthenia gravis, Myositis, Narcolepsy, Pancreatitis, Pemphigus vulgaris, Pernicious anaemia, Psoriasis, Psoriatic Arthritis, Polymyositis, Primary biliary cirrhosis, Relapsing polychondritis, Rheumatoid arthritis, Systemic sclerosis, Temporal arteritis (also known as "giant cell arteritis"), Ulcerative Colitis (one of two types of idiopathic inflammatory bowel disease "IBD"), Vasculitis, Wegener's granulomatosis.

Autophagy and Proteinopathies:

Inducing autophagy by using AcCoA depleting agents may be particularly suitable for the treatment of proteionpathies. Examples of proteinopathies include, but are not limited to Alzheimer's disease, cerebral β-amyloid angiopathy, retinal ganglion cell degeneration, prion diseases (e.g. bovine spongiform encephalopathy, kuru, Creutzfeldt-Jakob disease, variant Creutzfeldt-Jakob disease, Gerstmann-Straussler-Scheinker syndrome, fatal familial insomnia) tauopathies (e.g. frontotemporal dementia, Alzheimer's disease, progressive supranuclear palsy, corticobasal degeration, frontotemporal lobar degeneration), frontemporal lobar degeneration, amyotrophic lateral sclerosis, Huntington's disease, familial British dementia, Familial Danish dementia, hereditary cerebral hemorrhage with amyloidosis (Iclandic), CADASIL, Alexander disease, Seipinopathies, familial amyloidotic neuropathy, senile systemic amyloidosis, serpinopathies, AL amyloidosis, AA amyloidosis, type II diabetes, aortic medial amyloidosis, ApoAI amyloidosis, ApoII amyloidosis, ApoAIV amyloidosis, familial amyloidosis of the Finish type, lysozyme amyloidosis, fibrinogen amyloidosis, dialysis amyloidosis, inclusion body myositis/myopathy, cataracts, medullary thyroid carcinoma, cardiac atrial amyloidosis, pituitary prolactinoma, hereditary lattice corneal dystrophy, cutaneous lichen amyloidosis, corneal lactoferrin amyloidosis, corneal lactoferrin amyloidosis, pulmonary alveolar proteinosis, odontogenic tumor amylois, seminal vesical amyloid, cystic fibrosis, sickle cell disease and critical illness myopathy.

Pharmaceutical Compositions:

The agents of the present invention may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Galenic adaptations may be done for specific delivery in the small intestine or colon.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising agents of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The agent of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifusoluble agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The agent of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to he agents of the invention formulated for parenteral administration, such as intravenous or intramuscular injection, other pharmaceutically acceptable forms include, e.g. tablets or other solids for oral administration; liposomal formulations; time release capsules; and any other form currently used.

Methods of Screening:

A further object of the invention relates to a method for screening a plurality of test substances useful for inducing autophagy in a cell comprising the steps of (a) testing each of the test substances for its ability to deplete AcCoA in the cell and b) positively selecting the test substances capable of depleting AcCoA in the cell.

In some embodiments, the screening method of the invention comprises the steps of (a) testing each of the test substances for its ability to inhibit the activity or expression of a autophagy-related gene product selected from the group consisting of mitochondrial pyruvate carrier complex, mitochondrial carnitine palmitoytransferase-1, mitochondrial citrate carrier (CiC), ATP-citratre lyase (ACLY), EP300 acetyl-transferase and acyl-CoA synthetase short-chain family member 2 (ACCS2) and b) positively selecting the test substances capable of inhibiting the autophagy-related gene product In some embodiments, test substances useful in the screening methods of the present invention may be obtained from any available source, including systematic libraries of natural and/or synthetic compounds.

In some embodiments, any assay well known in the art may be performed for determining whether the test substance is able to deplete AcCoA in a cell. For example, assays for screening test substances which are substrates of the autophagy-related gene product are performed. Other examples include assays for screening test substances which binds to the autophagy-related gene product. Determining the ability of the test compound to directly bind to an autophagy-related gene product can be accomplished, for example, by coupling the compound with a radioisotope or enzymatic label such that binding of the substance to the autophagy-related gene product can be determined by detecting the labeled compound in a complex. For example, compounds can be labeled with 1251, 35S, 14C, or 3H, either directly or indirectly, and the radioisotope detected by direct counting of radioemission or by scintillation counting. Alternatively, assay components can be enzymatically labeled with, for example, horseradish peroxidase, alkaline phosphatase, or luciferase, and the enzymatic label detected by determination of conversion of an appropriate substrate to product. Test substances may also be identified, for example, using assays that identify substances which modulate (e.g., affect either positively or negatively) interactions between an autophagy-related gene product and its substrates and/or binding partners. Such substances can include, but are not limited to, molecules such as antibodies, peptides, hormones, oligonucleotides, nucleic acids, and analogs thereof. Such substances may also be obtained from any available source, including systematic libraries of natural and/or synthetic substances. The basic principle of the assay systems used to identify substances that modulate the interaction between the autophagy-related gene product and its binding partner involves preparing a reaction mixture containing the autophagy-related gene product and its binding partner under conditions and for a time sufficient to allow the two products to interact and bind, thus forming a complex. In order to test a test substance for inhibitory activity, the reaction mixture is prepared in the presence and absence of the test substance. The test substance can be initially included in the reaction mixture, or can be added at a time subsequent to the addition of the autophagy-related gene product and its binding partner. Control reaction mixtures are incubated without the test substance or with a placebo. The formation of any complexes between the autophagy-related gene product and its binding partner is then detected. The formation of a complex in the control reaction, but less or no such formation in the reaction mixture containing the test substance, indicates that the substance interferes with the interaction of the autophagy-related gene product and its binding partner. Conversely, the formation of more complexes in the presence of the substance than in the control reaction indicates that the substance may enhance interaction of the autophagy-related gene product and its binding partner. Inhibitors of autophagy-related gene product expression may also be identified, for example, using methods wherein a cell is contacted with a test substance and the expression of mRNA or protein, corresponding to an autophagy-related gene in the cell, is determined. The level of expression of mRNA or protein in the presence of the candidate substance is compared to the level of expression of mRNA or protein in the absence of the candidate substance. The candidate substance can then be identified as a modulator of autophagy-related gene product expression based on this comparison. For example, when expression of autophagy-related gene product is lower in the presence of the candidate substance than in its absence, the candidate substance is identified as an inhibitor of the autophagy-related gene product expression.

The invention will be further illustrated by the following figures and examples. However, these examples and figures should not be interpreted in any way as limiting the scope of the present invention.

FIGURES

FIG. 1: Nutrient starvation leads to a reduction of both AcCoA levels and cytoplasmic protein acetylation. A-B. Targeted analyses confirmed a reduction of total AcCoA (A) or cytosolic AcCoA (B) in human U2Os cell line and MEFs after 4 h of nutrient starvation. C. Targeted analyses also confirmed a reduction of AcCoA in vivo. D. Representative immunoblots of total cell lysates showing a reduction of protein acetylation and an increase of tubulin acetylation after 4 h of nutrient starvation. E. Representative pictures of immunofluorescence analyses against cytoplasmic acetylated lysine (left panels) or acetylated tubulin (right panels), after 4 h of nutrient starvation. Scale bar, 10 µm. F. Quantification of data depicted in G. at different time points during nutrient starvation.

Figure 2:
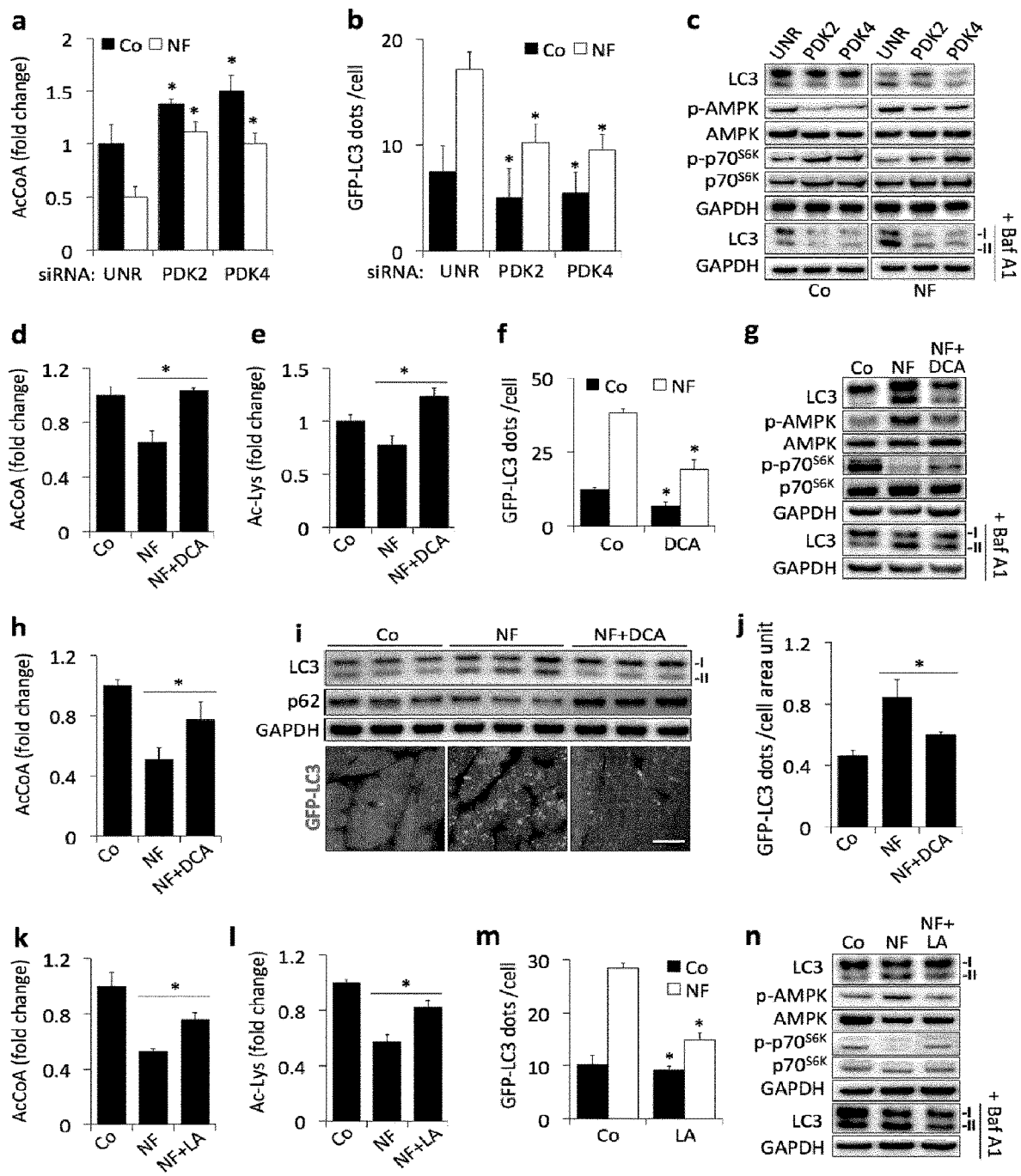

FIG. 2. Starvation-induced autophagy is inhibited by increased AcCoA production. A-C. PDK2 or PDK4 knockdown in U2OS cells led to an increase in AcCoA levels (A). In addition, either PDK2 or PDK4 knockdown was sufficient to inhibit starvation-induced autophagy, as measured by GFP-LC3 puncta formation (B) or by LC3 lipidation (C). This inhibition of starvation-induced autophagy was accompanied by a reduction in AMPK phosphorylation levels (C). A-G. Inhibition of PDKs by dichloroacetate (DCA) resulted in an increase in both AcCoA levels (D) and cytoplasmic protein acetylation (E), together with the inhibition of starvation-induced autophagy as measured by GFP-LC3 puncta formation (F) and LC3 lipidation, also associated with a reduction in AMPK phosphorylation and an increase in mTOR activity (G). H-J. PDKs inhibition by intraperitoneal injection of DCA resulted in increased AcCoA levels after 24 h-starvation (NF) in mice tissues, as compared with vehicle-treated mice (H). I. DCA treatment inhibited starvation-induced autophagy in vivo, as measured by LC3 lipidation (upper panel) or by fluorescence microscope analyses of hearts from GFP-LC3 transgenic mice (lower panel), quantified in (J). K-N. Lipoic acid (LA) inhibits starvation-induced autophagy and restores AcCoA depletion and cytoplasmic proteins acetylation. Supplementation of lipoic acid, an activator of the pyruvate-dehydrogenase complex (PDH) increased both cellular AcCoA levels (K) and cytoplasmic protein acetylation (L) in nutrient-depleted cells. Treatment with lipoic acid also abolished starvation-induced autophagy as measured by GFP-LC3 puncta (M) and LC3 lipidation (N). Scale bar, 10 µm. Unless otherwise depicted, asterisks indicate significance ($*p<0.05$, unpaired Student's t test) as compared to the corresponding condition in untreated controls (or UNR siRNA-transfected cells).

Figure 3:
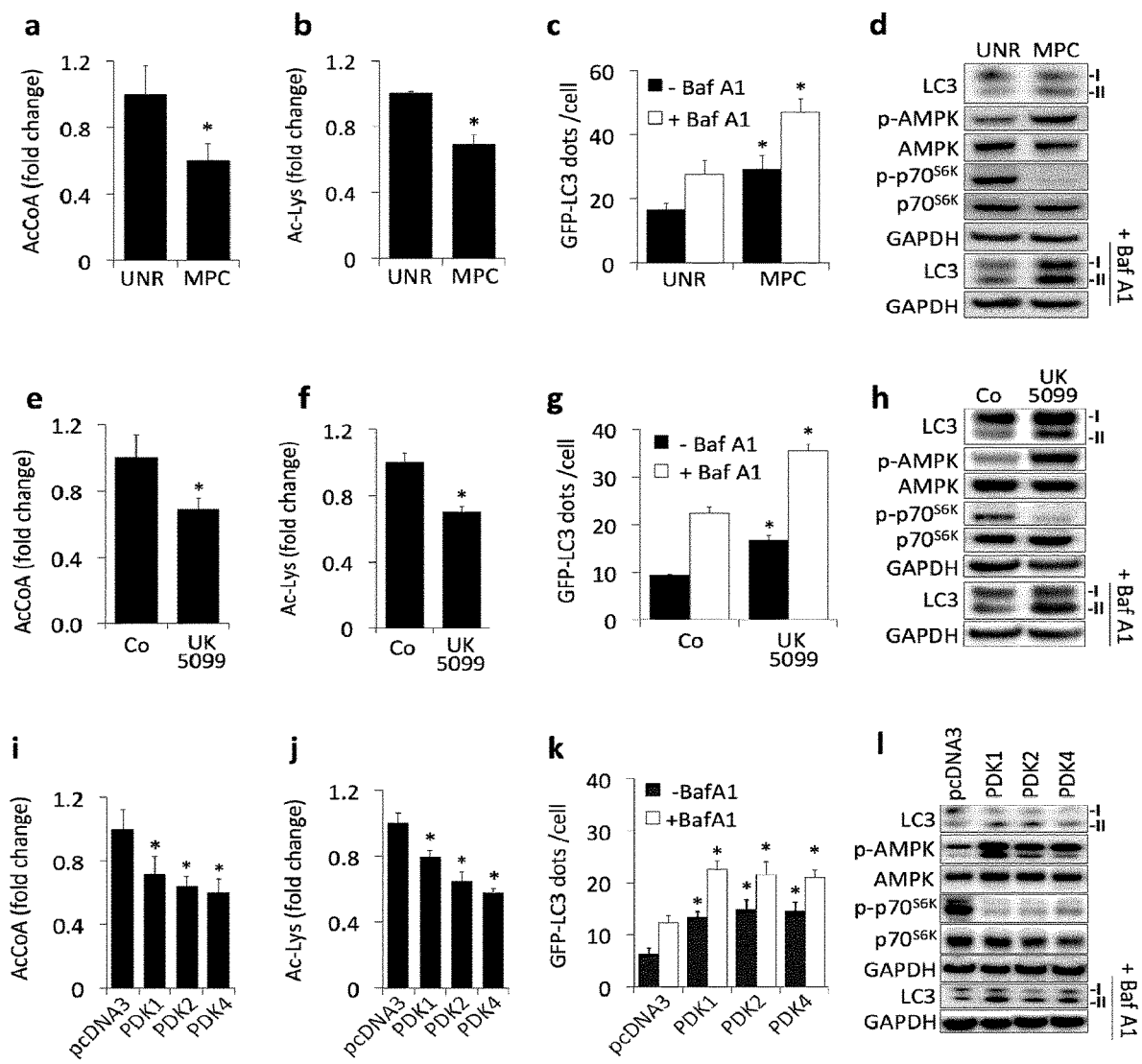

FIG. 3. AcCoA reduction by inhibiting pyruvate decarboxylation leads to increased autophagic flux. A-H. Inhibition of pyruvate transport from cytoplasm to mitochondria by mitochondrial pyruvate carrier (MPC) knockdown or by the pyruvate carrier inhibitor UK5099 reduced both AcCoA levels (A, E) and cytoplasmic protein acetylation (B, F), while it increased autophagic flux as measured by GFP-LC3 puncta formation (C, G) and LC3 lipidation (D, H). I-L. PDH inhibition after PDK1, -2 and -4 overexpression in U2Os cells lead to a decrease in AcCoA levels (I), and in the acetylation of cytoplasmic proteins (J), as well as to an increase in autophagic flux (K), lipidation of LC3, an increase in AMPK phosphorylation and a decrease in mTOR activity, as measured by p70s6k phosphorylation levels (L). Asterisks indicate significance ($*p<0.05$, unpaired Student's t test) as compared to the corresponding condition in untreated controls (or as compared to pcDNA3 transfected cells).

Figure 4:
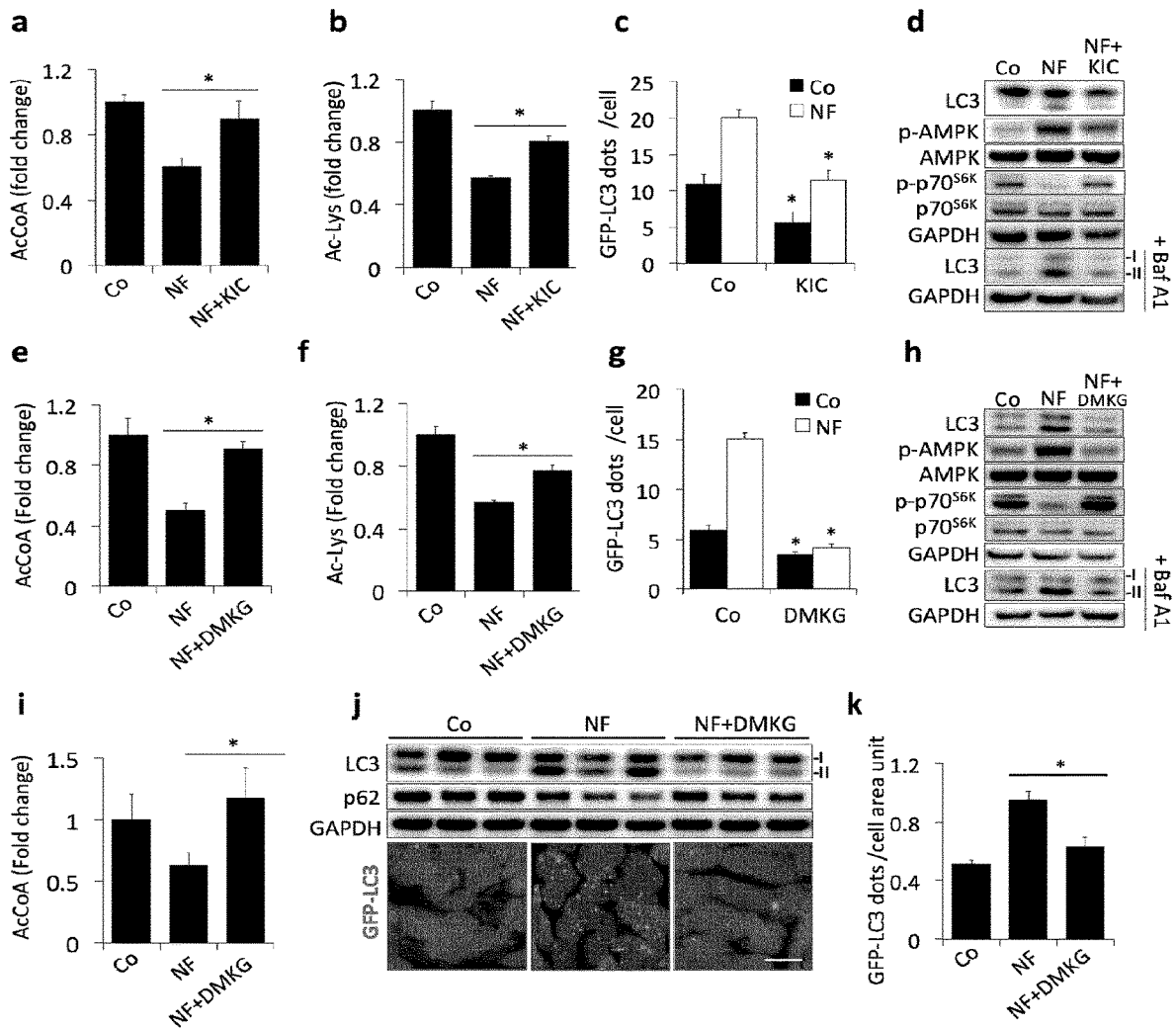

FIG. 4. Direct manipulation of AcCoA levels abolishes autophagy induction by nutrient and serum deprivation. A-D. Supplementation of ketoisocaproic acid (KIC) resulted in an increase in AcCoA levels (A) and cytoplasmic protein acetylation (B), together with an inhibition of starvation induced autophagy (C), inhibition of AMPK phosphorylation and reversion of mTORC1 dephosphorylation (D). E-H. Supplementation of dimethy-α-ketoglutarate (DMKG), a cell-permeable α-ketoglutarate ester, increased cellular AcCoA levels (E) and cytoplasmic protein acetylation (F) in nutrient-depleted cells. DMKG treatment also abolished starvation-induced autophagy as indicated by the formation of GFP-LC3 puncta (G) and LC3 lipidation (H). I-K. Effects of DMKG on starvation-induced autophagy. Intraperitoneal injection of DMKG resulted in increased cardiac AcCoA levels (I) after 24 h-starvation (NF), as compared with vehicle-treated mice. DMKG treatment inhibited starvation-induced autophagy in vivo, as measured by LC3 lipidation (upper panel in J) or by fluorescence microscope analysis of GFP-LC3 transgenic mice (lower panel in J) in heart tissue, quantified in (K). Scale bar, 10 µm. Unless otherwise depicted, asterisks indicate significant ($*p<0.05$, unpaired Student's t test) as compared to the corresponding control conditions.

Figure 5:
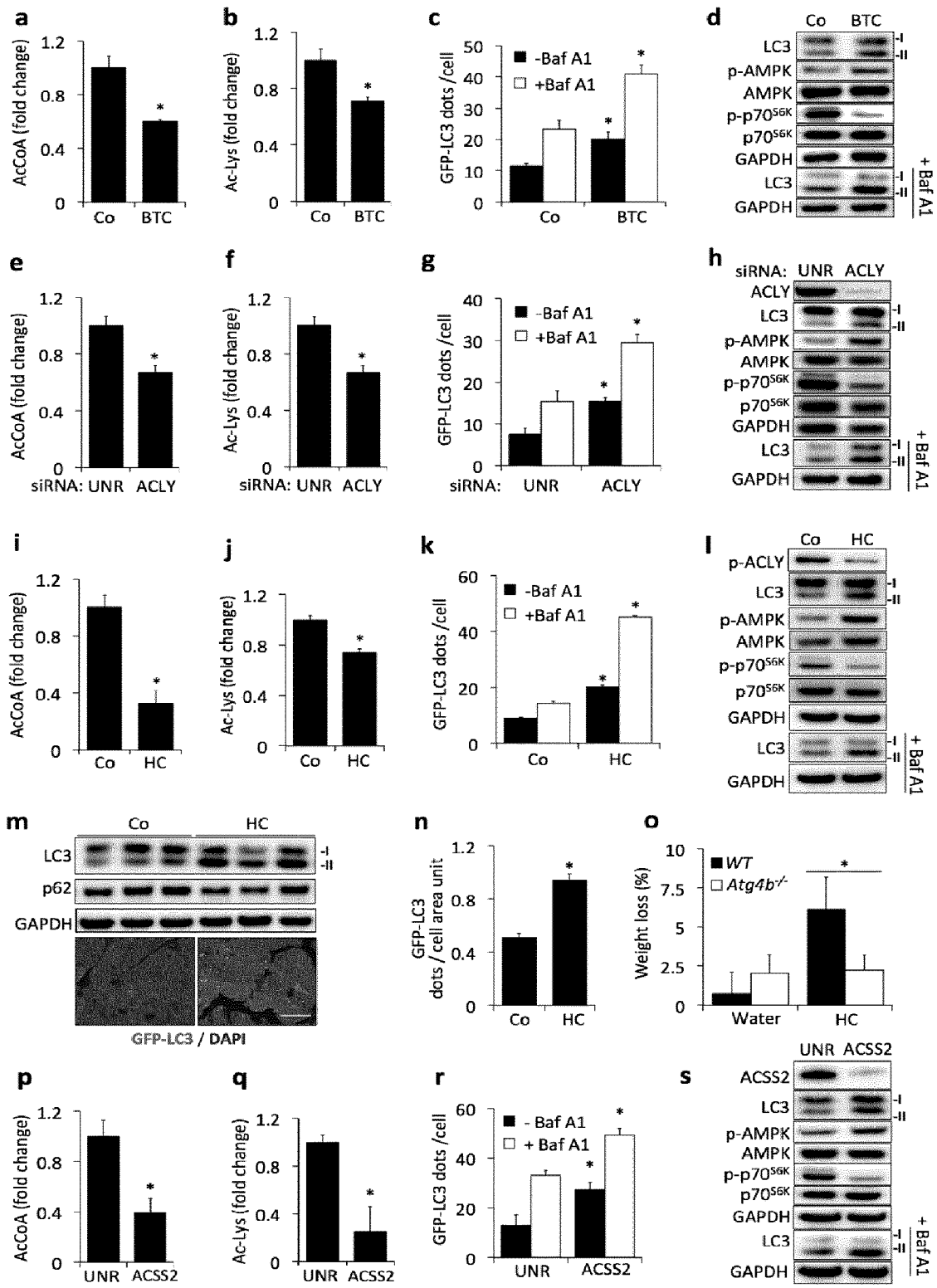

FIG. 5. Cytoplasmic AcCoA reduction increases autophagic flux. A-D. Inhibition of citrate transport from mitochondria to cytoplasm by benzenetricarboxylate (BTC) reduced both AcCoA levels (A) and cytoplasmic protein acetylation (B), while it increased autophagic flux as measured by GFP-LC3 puncta formation (C) and LC3 lipidation (D). E-L. Inhibition of ATP citrate lyase by ACLY knockdown or by its competitive inhibitor, hydroxycitrate (HC), reduced both AcCoA levels (E, I) and cytoplasmic protein acetylation (F, J), while it increased autophagic flux (G,H, K,L). M-N. Intraperitoneal injection of HC induced an increase in autophagic flux in vivo, as measured by immunoblot analysis of LC3 lipidation and p62 cellular levels (upper panel in M), or by fluorescence microscope analysis of GFP-LC3 transgenic mice (bottom panels in M) in heart tissue, quantified in (N). O, Effects of one week of HC treatment (900 mg/kg per day, orally) with food ad libitum on the body weight of WT and Atg4b$^{-/-}$ mice. Averages and standard deviations of weight loss are depicted. Knockdown of cytoplasmic AcCoA synthetase (ACSS2) reduced both AcCoA levels (P) and cytoplasmic proteins acetylation (Q), while it increased autophagic flux (R, S). Scale bar, 10 µm. Asterisks indicate significance ($*p<0.05$, unpaired Student's t test) as compared to the corresponding condition in controls (or UNR siRNA-transfected cells).

Figure 6:
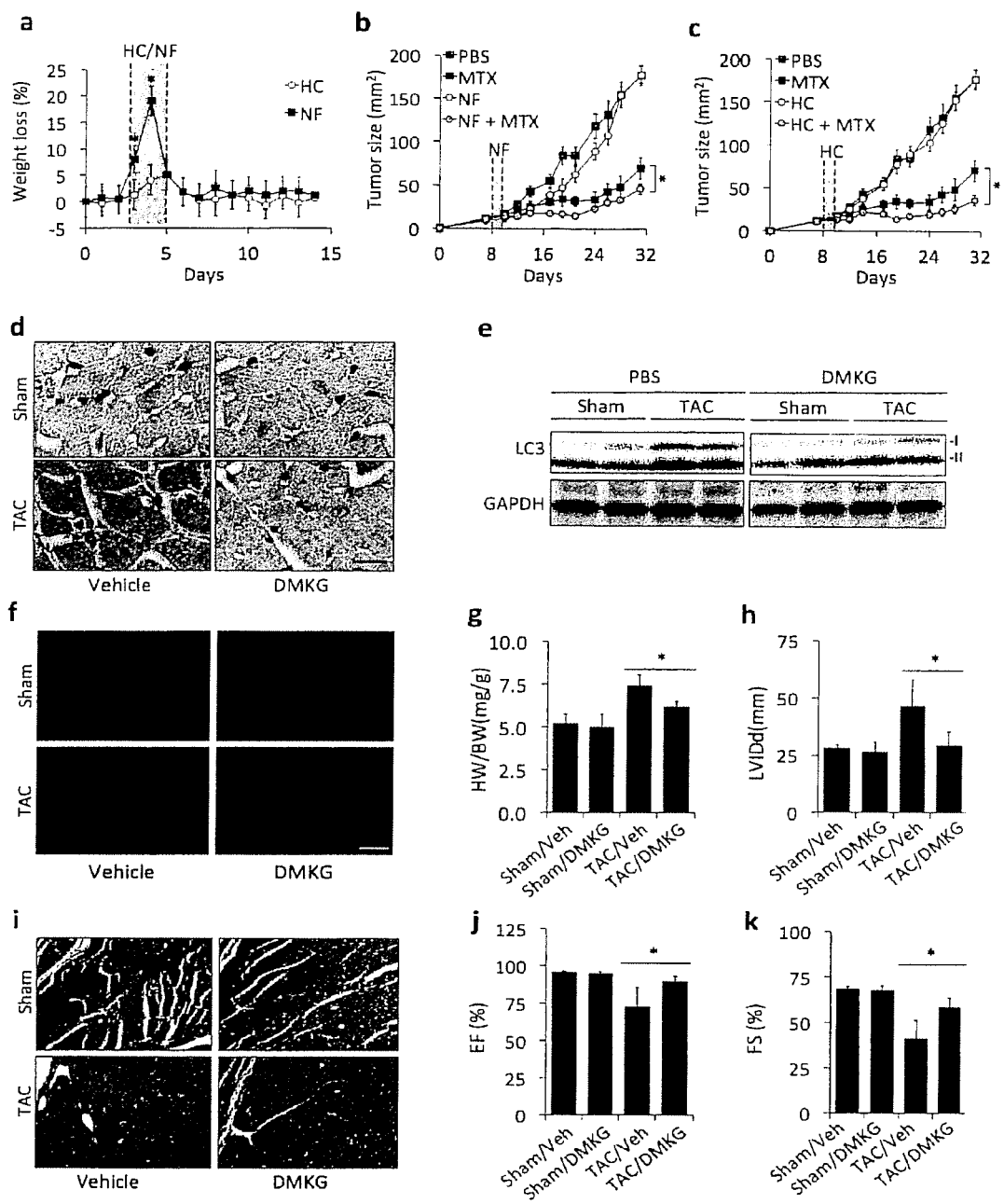
Figure 6:
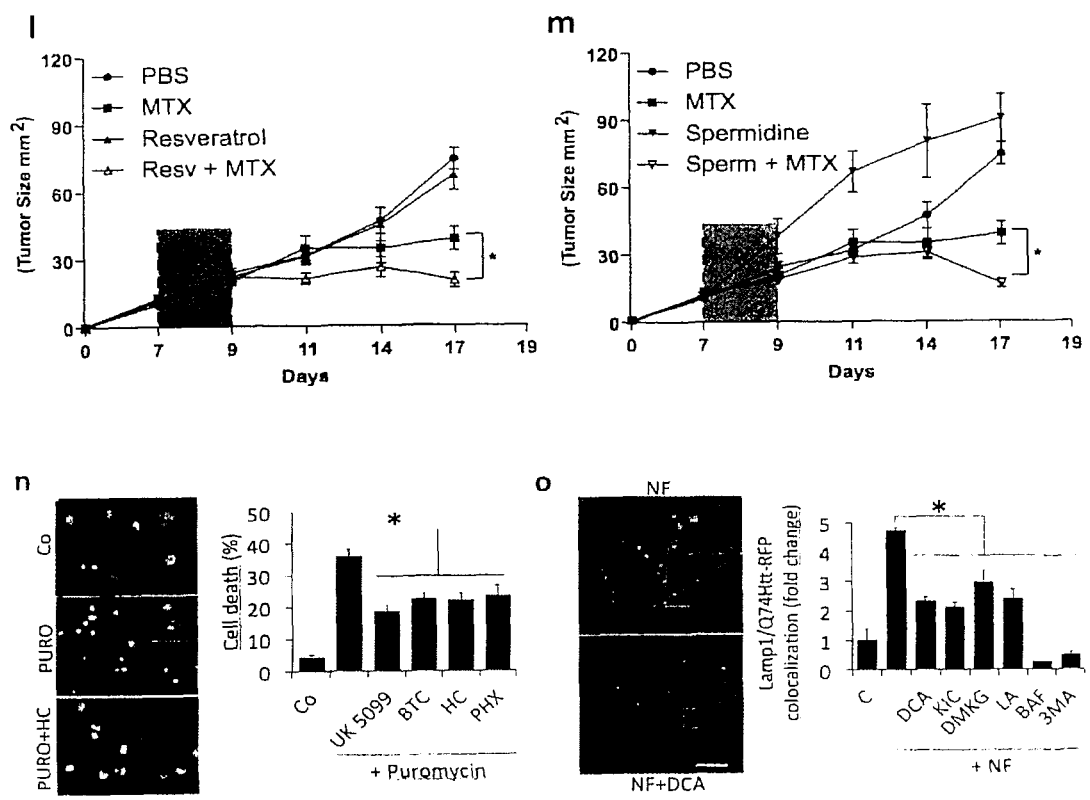

FIG. 6. Modulation of AcCoA levels for acute therapeutic effects in mice and in a model of neurodegenerative disease. A-C, HC administration mimics the effects of 48 h fasting in delaying subcutaneous MCA205 tumor growth when combined with the chemotherapeutic agent mitoxanthrone (MTX). A. Effect of 48 h fasting and HC administration in body weight. B,C. Effects of 48 h fasting (B) or two-day oral HC treatment (C) in tumor growth alone or in combination with a single i.p. dose of MTX. Both graphs correspond to the same experiment, but have been split to facilitate comprehension. Asterisks indicate significance ($*p<0.05$, unpaired Student's t test) as compared to untreated controls. D-K. Effects of DMKG treatment onpressure overload-induced maladaptive autophagy in the heart. Daily intraperitoneal injections of DMKG at a dose of 300 mg/kg of body weight decreased cardiac autophagy induced by thoracic aortic constriction (TAC), as measured by IHC (D) or immunoblotting (E). DMKG administration also suppressed TAC-induced pathological remodeling, including cardiomyocyte hypertrophy as measured by wheat germ agglutinin in transverse sections of the left ventricle (F), ventricular hypertrophy, expressed as the heart weight/body weight ratio (G), ventricular dilatation measured as the internal diameter (H), cardiac muscle fibrosis measured by trichrome staining (I), and reduction in contractile performance quantified as ejection fraction (J) or fractional shortening (K). Scale bars, 15 µm in (D), 40 µm in (F) and 100 µm in (I). µm, L-M Spermidine and Resveratrol (caloric restriction mimetics) administration mimics the effects of 48 h fasting in delaying subcutaneous MCA205 tumor growth when combined with the chemotherapeutic agent mitoxanthrone (MTX). (N) AcCoA lowering agents rescue cell death mediated by Huntingtin Q74 aggregation. Q74-Htt expressing U2Os cells were incubated for 12 h in the presence of 300 ng/μL of puromycin to potentiate Htt aggregation. Cells were then fixed and cell death was estimated by analyzing nuclear morphology. Left, representative pictures, right, statistical analysis. (O)AcCoA replenishing agents reduce starvation-induced Htt-LAMP1 co-localization. Left, representative pictures, right, statistical analysis. Scale bar, 50 μm.

Figure 7:
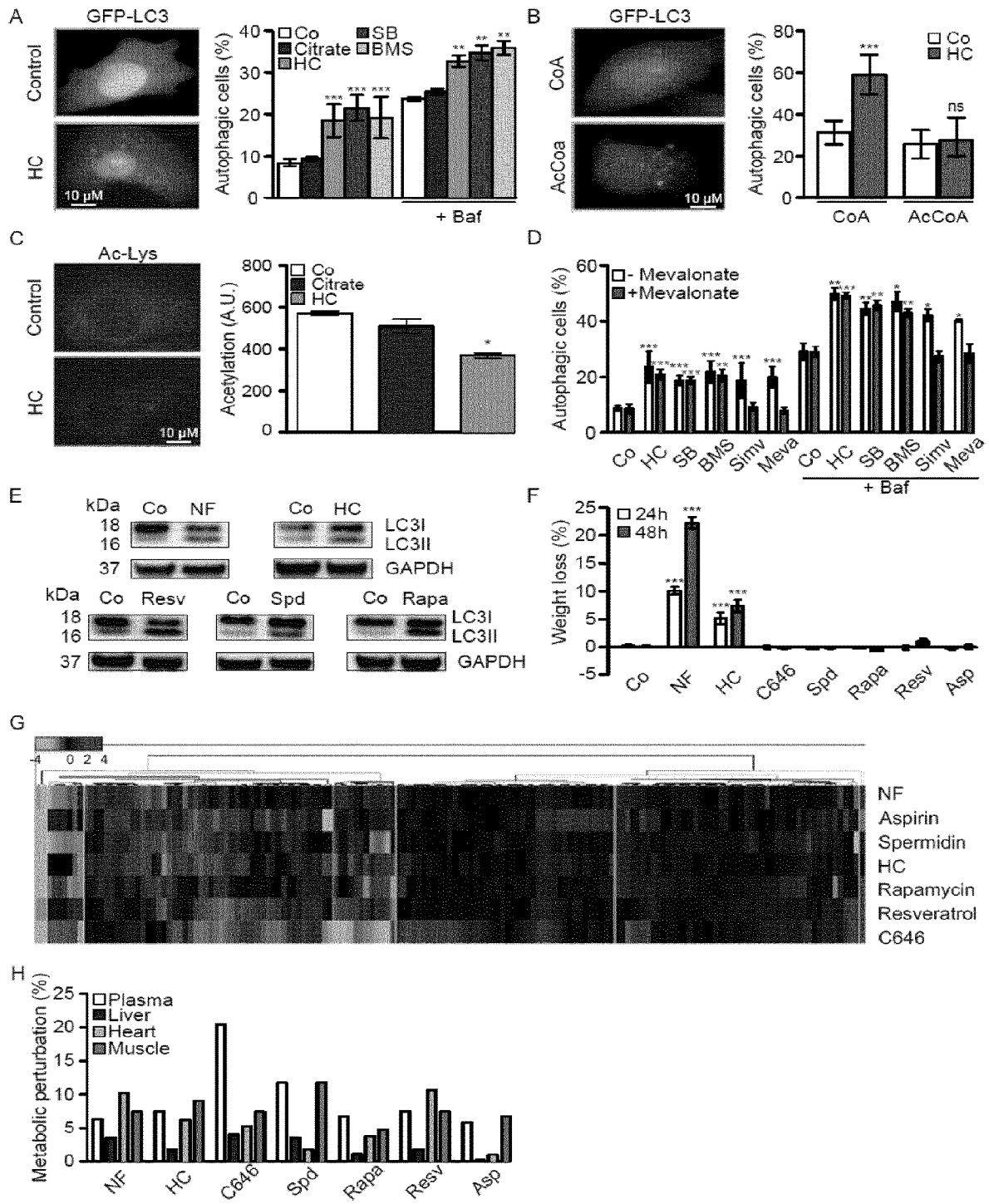

FIG. 7: Autophagy induction and metabolic effects of hydroxycitrate and other caloric restriction mimetics. A. Stimulation of U2OS cells stably expressing GFP-LC3 with competitive ACLY inhibitor HC (Hydroxycitrate) and non-competitive inhibitors SB204990 and BMS303141, but not with its natural substrate citrate, induce autophagic flux as measured by GFP-LC3 puncta formation in presence and absence of Bafilomycin A1. Representative pictures and quantification in A. Scale Bar 10 μm. Results are shown as means±SEM from three different experiments. *p<0.001 p<0.01 (unpaired Student's t test) compared to control conditions. B. Effects of Acetyl CoA microinjection on HC-induced autophagy. (B) Representative pictures of Acetyl-CoA injected HC-treated cells. U2OS cells were injected into the cytoplasm with 10 mM Acetyl Coa. Acetyl CoA, but not CoA injection inhibits Hydroxycitrate-induced autophagy. Scale Bar 10 μM. Results are depicted as means±SD ** p<0.01 (unpaired Student's t test) compared to control conditions C. Impact of ACLY inhibitors stimulation on Cytoplasmic Protein Acetylation. 6 hours incubation of U2OS cells in presence of Hydroxycitrate ACLY reduces cytoplasmic. Representative pictures and quantification in C. Scale bar 10 μM. Results are illustrated as means±SEM * p<0.05 (unpaired Student's t test) compared to control conditions. D. HC-induced autophagy does not rely on cholesterol biosynthesis inhibition. U2OS GFP-LC3 cells were treated for 12 hours with ACLY inhibitors or HMG-COA (Hydroxymethylglutaryl CoA) Reductase inhibitors Simvastatin and Mevastatin, in presence or absence of HMG-GOA metabolic product Mevalonate. Mevalonate administration reverts statins-induced, but not ACLY inhibition mediated-, autophagy, as quantified in D. Results are shown as ±SEM from three different experiments. * p<0.001  p<0.01 * p<0.05 (unpaired Student's t test) compared to control conditions E. Effects of CRMs (Caloric Restriction Mimetics) administration on autophagy induction in mice muscle. Intraperitoneal injection of CRMs Hydroxycitrate, Resveratrol, Spermidine, c646, as well as that of autophagy inducer Rapamycin elicits autophagy in mice muscle after 6 hours, mimicking 48 hours fasting-induced autophagy, as measured by LC3 lipidation (representative blots in E). F. 48 hours starvation provokes a drastic weight reduction which is not shared by others CRMs. Results are shown as means±SD on n=5 mice per group G. Clustering of metabolites, the concentration of which significantly differed in mice plasma after 48 hours starvation compared with two injections of CRMs. Values are expressed as fold change compared to untreated controls. J. Percentage of metabolic alterations of CRMs compared with 48 hours fasting. Panel J depicts the percentage of significantly changed metabolites upon CRMs treatment compared to 48 hours starvation, indicating the divergence of metabolic changes.

Figure 8:
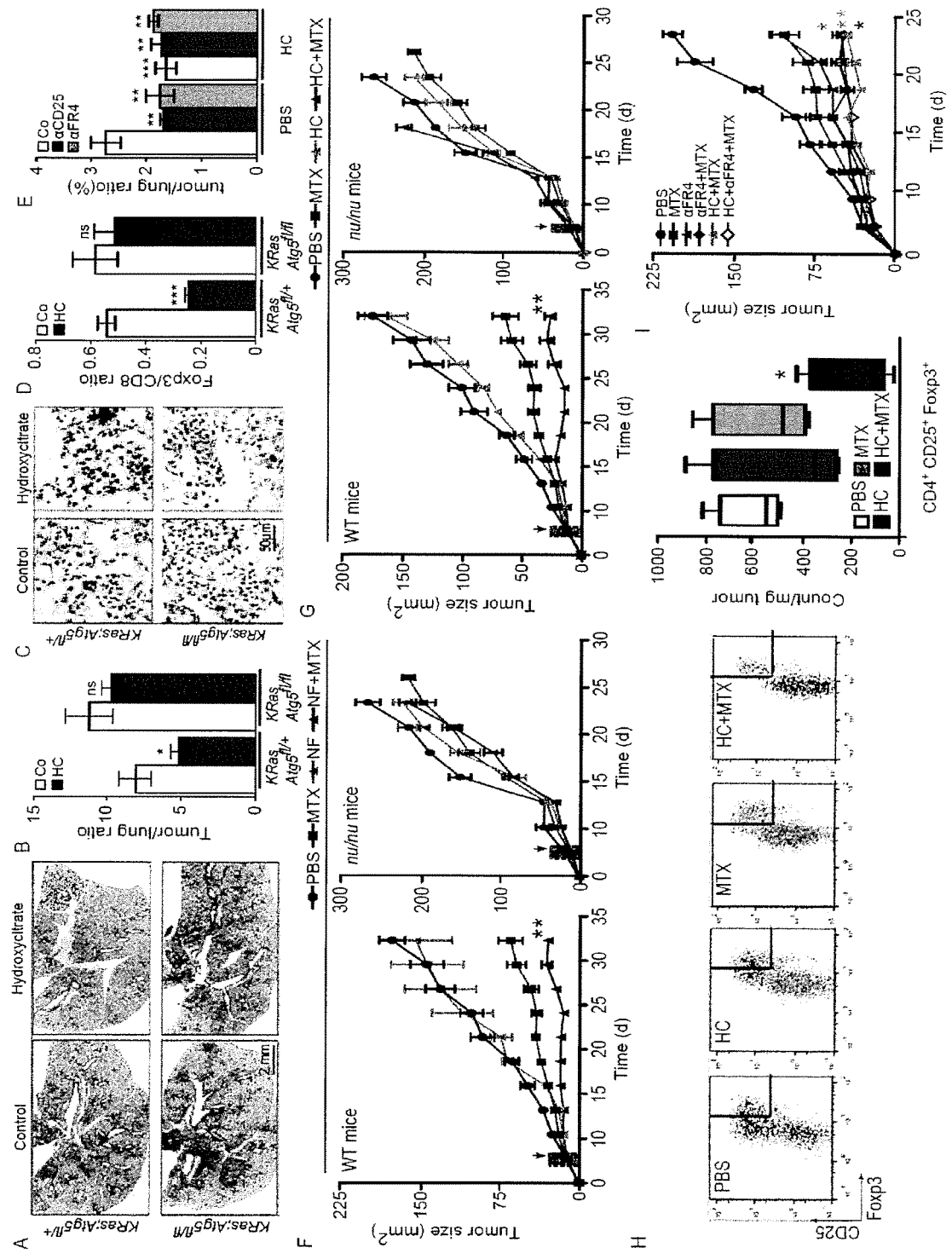

FIG. 8. Hydroxycitrate improves antitumor immunity in an autophagy-dependent manner specifically reducing FoxP3+ Regulatory T cells in tumor infiltrate. (A,B) HC reduces tumor size and lesions in Kras-induced lung cancer in KRas;Atg5fl/+ mice but not in KRas;Atg5$^{fl/fl}$ littermates. A. Hematoxilin and Eosin staining of representative histological sections after AdCre inhalation and after 5 weeks HC administration in drinking water. Quantifications are shown in B. Scale bar 2 mm. B. Quantifications of data depicted in A. Results are expressed as means±SEM from three different experiments * p<0.05 (unpaired Student's t test) compared to control conditions (C,D) HC reduces CD3+ FOXP3 Regulatory T cells in tumor bed from KRas;Atg5fl/+ mice but not in KRas;Atg5$^{fl/fl}$ littermates. C. Representative histological section of CD3 FOXP3 stained T cells after xx weeks HC administration, quantified in D. Scale bar 50 μm. D. Quantifications of images shown in C. Results are depicted as means±SEM from three independent experiments * p<0.001 compared to control condition E. Antineoplastic effects of HC specifically rely on FOXP3+ Tregs reduction in tumor bed. Epistatic analysis showing that depletion of Tregs by administration of antibody against FR4 and CD25 surface markers reproduces the antitumor effect of HC. Results are illustrated as means±SEM from three different experiments. * p<0.001  p<0.01 compared to PBS group F. Tumor growth curves of mice undergone 48 fasting and anthracyclin based chemotherapy. Fasting enhances efficacy of MTX (Mitoxanthrone) in transplantable tumor model in wild type but not in nude athymic mice. 48 hours fasting followed by injection of the anthracycline MTX significantly reduces tumor growth of MCA205 cells if compared with chemotherapy alone. The positive combinatorial effect is lost in mice devoid of immune system. Results are depicted as means±SEM from at leat three different experiment with n=8 mice per experimental group.  p<0.01 (unpaired Student's t test) compared to MTX group G. Tumor growth curves of mice intraperitoneally administered with HC and anthracyclin based chemotherapy. The CRM HC improves the efficacy of chemotherapy and significantly reduces tumor growth of MCA205 cells in wild type, but not in nu/nu mice. HC positively mimics nutrient starvation and boosts chemotherapy efficacy if compared to MTX alone when mice are immunocompetent. Results are depicted as means±SEM from at least three different experiment with n=8 mice per experimental group. ** p<0.01 (unpaired Student's T test) compared to MTX group H. The combinatorial treatment of HC and MTX reduces Treg infiltration in tumor bed. Representative FACS profile and quantification of CD4$^+$CD25$^+$ Foxp3$^+$ cells per mg of tumors. Combinatorial treatment specifically depletes Foxp3$^+$ Tregs from tumor bed. Results are depicted as means±SD from experiments with n=5 mice. * p<0.05 (unpaired Student's t test) compared with MTX group. I. Treg depletion and HC administration similarly improve the effect of MTX in reducing tumor growth. Tumor growth curve of mice treated with HC+ MTX combination and MTX+FR4-mediated Tregs depletion. Results are depicted as means±SEM from experiments with n=8 mice per experimental group. *p<0.05; ** p<0.01 (unpaired Student's T test) compared to MTX group.

Figure 9:
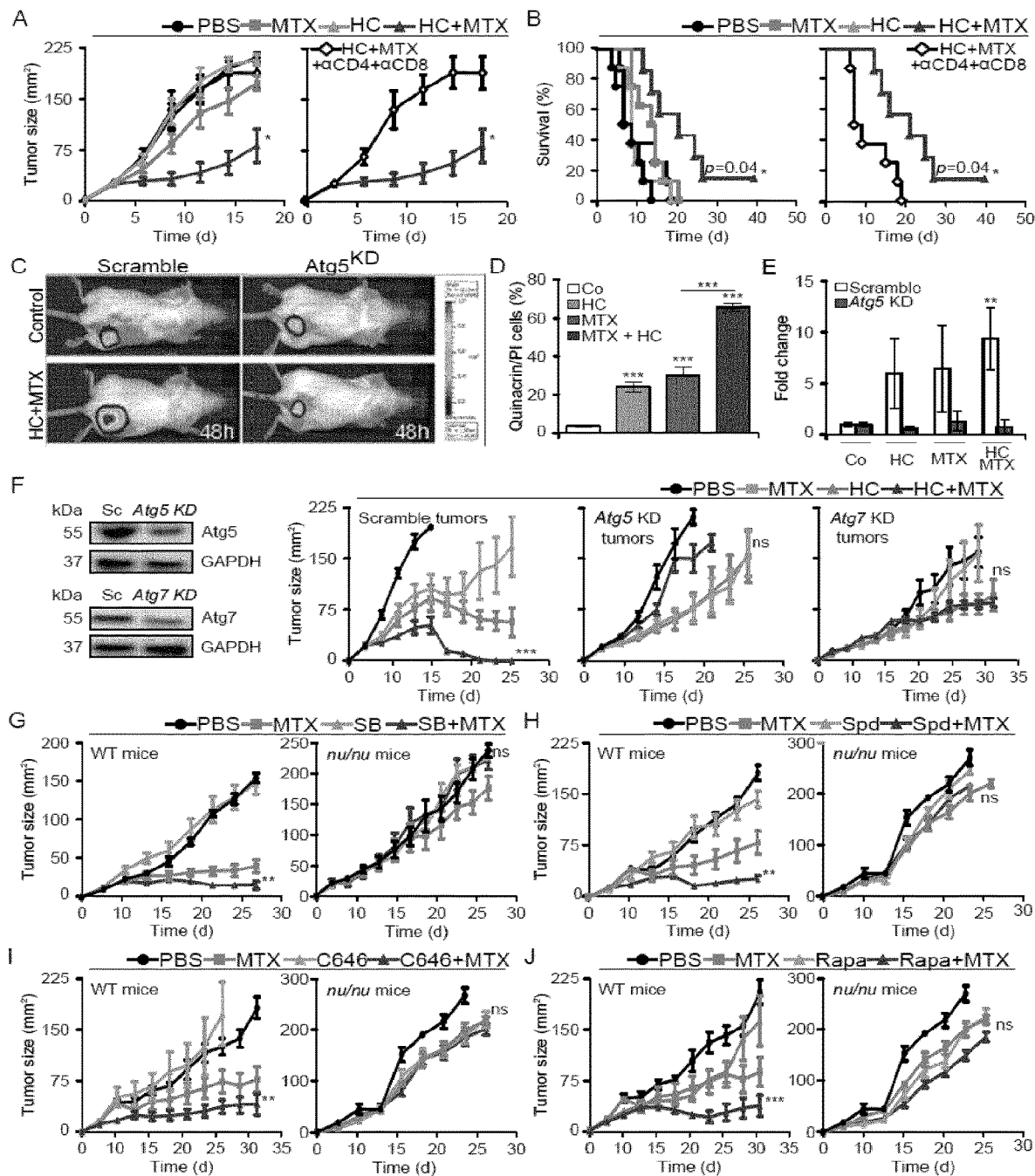

FIG. 9. HC plus MTX combined chemotherapy enhances the autophagy-dependent release of ATP in vivo and in vitro and can be efficiently replaced by distinct CRMs. (A,B) A. HC plus MTX combinatorial treatment reduces tumor growth and increases survival in chemical-induced model of mammary tumor in mice capable to mount a T-cell dependent immune response. A. Tumor growth curve of MPA/DMBA induced mammary cancer. HC+MTX significantly diminish tumor growth in MPA/DMBA induced mammary tumors thus ameliorating the effects of monotherapy. Beneficial effect of combinatorial treatment is lost upon antibody specific depletion of CD and CD8 T cells B. Kaplan-Meier curve showing the significantly increased survival of mice treated with HC+MTX. The augmented survival is lost in mice devoid of CD4/CD8 T lymphocytes. * p=0.04 (Log-Rank test) compared with PBS and CD4/CD8 depleted groups (C,E) HC+MTX combination boosts the autophagy-dependent release of ATP in vivo and in vitro therefore eliciting an antitumor immune response. C. Measurement of extracellular ATP release after HC+MTX treatment in autophagy competent and deficient tumors. PMELuc-engineered CT26 derived tumors expressing Scamble or ATG5 shRNA were treated with PBS, HC, MTX and MTX+HC. ATP release was monitored 48 hours post chemotherapy. Combinatorial treatment significantly enhances ATP release compared to basal condition in autophagy competent tumors (quantified in E) D. Measurement of extracellular ATP release in vitro. Quinacrine/PI double staining of MCA205 cells reveals showed a marked increase in ATP release of HC+MTX group compared to MTX alone. Results are depicted as means±SEM from there different experiments *** $p<0.001$ (unpaired Student's t test) compared to PBS group and to MTX group. E. Quantification of data depicted in C. Results are represented as Photons flux ratio Fold Change±SEM from there different experiments * $p<0.05$ (unpaired Student's t test) compared to PBS group F. HC+MTX-mediated tumor growth control is lost in tumors derived from autophagy deficient cells (immunoblot in the left panel). Tumor growth curves of tumors derived from MCA205 cells transfected with Scramble, Atg5 and Atg7 shRNA. Deficient autophagy in the tumor abolishes the beneficial effect of combinatorial treatment. Results are illustrated by means±SEM from three different experiments with n=5 mice per experimental group * $p<0.001$ (unpaired Student's t test) compared to MTX group (G-J). Different CRMs are able to trigger an immune-dependent anticancer response and can enhance chemotherapy efficacy. Tumor growth curve of MCA205 derived tumors in WT and immunedeficient mice treated with the ACLY inhibitors SB204990 (G), the polyamine Spermidine (H), the EP300 inhibitors c646 (I) and canonical autophagy inducer Rapamycin (J), alone or combined with MTX. Results are depicted as means±SEM from three different experiments with n=5 mice per experimental group. * $p<0.001$ ** $p<0.01$ (unpaired Student's t test) compared to MTX group.

Figure 10:
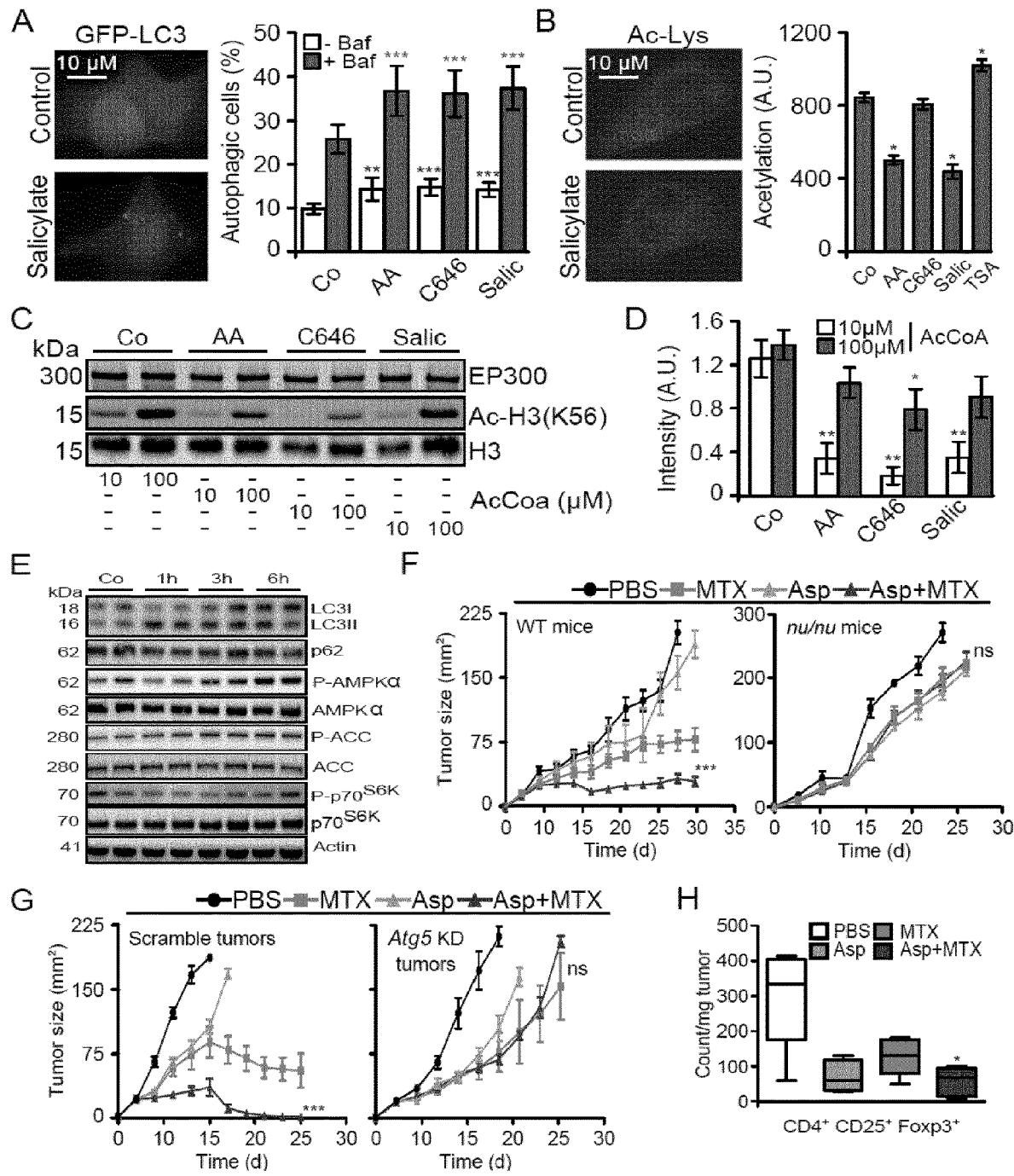

FIG. 10. Acetylsalycilic acid is bona fine a newly identified CRMs which is able to induce autophagy and to trigger autophagy-dependent anti-tumor immunity. (A-E) The active metabolite Salycilate induces autophagic flux in vivo and in vitro and rapidly induces deacetylation of cytoplasmic protein in vitro, thus behaving as CRM (A). Administration of 1 mM Salycilate to U2OS GFP-LC3 cells for 6 hours induces autophagy, as measured by LC3 puncta formation. Structural analog Anacardic acid and EP300 inhibitor c646 were used as positive controls. Representative images of Salycilate stimulated cells and corresponding quantification. Results are shown as means±SEM from three different experiments.* $p<0.001$  $p<0.01$ (unpaired Student's t test) compared to control condition B. Stimulation of U2OS cells for 6 hours with 1 mM Salycilate reduces cytoplasmic protein acetylation, as measured by anti-Acetyl Lysine staining by immunofluorescence. Broad range Acetyltransferase inhibitor Anacardic Acid, but not the EP300 specific inhibitor c646, was used as positive control for reduced protein acetylation, whereas the large spectrum deacetylase inhibitors Trichostatin A was adopted as control of enhanced protein acetylation. Representative images and corresponding quantification are showed in B. Results are shown as means±SEM from three different experiment * $p<0.05$ (unpaired Student's t test) compared to control condition (C-D) Salycilate inhibits Acetyltransferase activity of EP300 in a cell free system in vitro assay by competing with acetyl CoA. C. Representative Immunoblotting from there independent experiments depicting the Acetylation of EP300 specific substrate histone H3 on Lysine 56 upon stimulation with 1 mM Salycilate, in presence of 10 and 100 µM Acetyl CoA. 50 µm Anacardic acid and 3 µM c646 were used as positive control for EP300 activity inhibition. D. Quantification of C. E. The prodrug Acetylsalicylic Acid induces autophagy in mice tissues. Representative Immunoblotting from three different independent experiments depicting autophagy induction in mice heart 1 hour, 3 hours and 6 hours after intraperitoneal injection of 10 mg/kg of Acetylsalycilic Acid. Aspirin induces autophagy as measured by LC3I to II lipidation and p62 degradation. Acetylsalycilate increased AMPK phosphorylation (Thr142) and the consequent AMPK-dependent inhibitory phosphorylation of ACC (Ser79) AcetylCoA Carboxylase and reduces the phosphorylation of mTOR substrate p70S6 kinase (Thr389). (F-I). Aspirin improves anticancer immunity in immunocompetent mice in an autophagy dependent manner. F. Aspirin injection ameliorates the cancer killing effect of chemotherapy in wild type but not in nude mice. F. Tumor growth curve of MCA205 derived tumor treated with Aspirin and MTX alone or in combination. G. Tumor growth control mediated by Aspirin+MTX combinatorial treatment relies on autophagy induction in the tumor. Tumor growth curves from MCA205 scrambled or expressing shRNA construct targeting autophagy essential gene ATG5. *** $p<0.001$ (unpaired Student's t test) compared with MTX alone. H. Aspirin+MTX combined treatment favors FOXP3+ Treg depletion in tumor bed thus improving immune surveillance. Box plot showing CD4+CD25+ FOXP3+ Tregs count per mg of tumor. Box plot depicting means. Results are depicted as means±SD from experiments with n=5 mice per experimental group * $p<0.05$ (unpaired Student's t test) compared with MTX group.

EXAMPLE 1

Chemicals, Cell Lines and Culture Conditions.

Unless otherwise specified, chemicals were purchased from Sigma-Aldrich (St. Louis, USA), culture media and supplements for cell culture from Gibco-Invitrogen (Carlsbad, USA) and plastic ware from Corning (Corning, USA). Human colon carcinoma HCT 116 cells were cultured in McCoy's 5A medium containing 10% fetal bovine serum, 100 mg/L sodium pyruvate, 10 mM HEPES buffer, 100 units/mL penicillin G sodium and 100 µg/mL streptomycin sulfate (37° C., 5% $CO_2$). Human osteosarcoma U2Os cells, their GFP-LC3-expressing derivatives, human neuroblastoma H4 GFP-LC3 (gift from Prof J. Yuan) cells and human GFP-LC3-expressing HeLa cells were cultured in DMEM medium containing 10% fetal bovine serum, 100 mg/L sodium pyruvate, 10 mM HEPES buffer, 100 units/mL penicillin G sodium and 100 µg/mL streptomycin sulfate (37° C., 5% $CO_2$). Mouse embryo fibroblasts (MEFs) were cultured in the same DMEM with additional supplementation of non-essential amino-acids and β-mercaptoethanol. Cells were seeded in 6-, 12-well plates or in 10-, 15 cm dishes and grown for 24 h before treatment with 10 µM rapamycin (Tocris Bioscience, Bristol, UK), 5 mM dimethyl α-ketoglutarate (Sigma Aldrich), 20 mM hydroxycitrate (Sigma Aldrich), 5 mM α-ketoisocaproate (Sigma Aldrich), 50 mM L-leucine (Sigma Aldrich), 20 mM sodium dichloroacetate (Sigma Aldrich), 5 mM 1,2,3-benzenetricarboxylic acid hydrate (Sigma Aldrich), 10 µM perhexiline maleate salt (Sigma Aldrich), 5 mM (±)-α-lipoic acid (Sigma Aldrich), 100 nM bafilomycin A1 (BafA1, Tocris) and UK5099 (Sigma Aldrich), 100 µM curcumin, 3-methyl-butyrolactone an garcinol, 50 µM anacardic acid and 10 µM timosaponin A-III, PI-103, moperamide, amiodarone, nimodipine, nitrendipine, niguldipine, rotenone, rifluoperazine, sorafenib tosylate, niclosamide, rottlerin, caffeine, metformin, clonidine, rilmenidine, 2',5'-dideoxyadenosine, suramin, pimozide, STF-62247, spermidine, FK-866, tamoxifen citrate, glucosamine, HA 14-1, licochalcone A, vurcumin, Akt Inhibitor X, rockout, 2-deoxyglucose, etoposide, C2-dihydroceramide and temozolomide (all from Enzo life-sciences, Villeurbanne, France) or 3 µg/mL puromycin (Sigma Aldrich). For serum and nutrient deprivation, cells were cultured in serum-free Hank's balanced salt solution (HBSS).

Plasmids, Transfection and RNA Interference in Human Cell Cultures.

Plasmids encoding pyruvate dehydrogenase kinase (PDKs) cDNAs were obtained from Addgene (Cambridge, USA). Transient plasmid transfections were performed with the Attractene® reagent (Qiagen, Hilden, Germany), and, unless otherwise indicated, cells were analyzed 24 h after transfection. siRNAs were reverse-transfected with the help of the RNAi Max™ transfection reagent (Invitrogen, Eugene, USA).

Microinjection Experiments.

For microinjection, U2Os cells were cultured overnight on glass coverslips before injection. The setup for the injection itself was as follows: 10 mM CoA or AcCoA were injected in PBS for 0.2 s under a pressure of 150 hPa, using a Microinjector equipment (Eppendorf, Hamburg, Germany). Then cells were culture for 3 h in the presence of 100 nM bafilomycin A1 (BafA1) and fixed for fluorescence microscopy, as described below.

Immunofluorescence.

Cells were fixed with 4% PFA for 15 min at room temperature, and permeabilized with 0.1% Triton X-100 for 10 min, except for staining of cytoplasmic acetyl-lysine-containing proteins, in which any permeabilization step further than PFA fixation was avoided. Non-specific binding sites were blocked with 5% bovine serum in PBS, followed by staining with primary antibodies overnight at 4° C. Development was carried out with appropriate AlexaFluor™ conjugates (Molecular Probes-Invitrogen). In the case of cytoplasmic acetyl-lysine staining, an additional step of blocking using anti-acetylated-tubulin antibody (1:200) was applied. Ten µM Hoechst 33342 (Molecular Probes-Invitrogen) was employed for nuclear counterstaining. Fluorescence and confocal fluorescence microscopy assessments were performed on an IRE2 microscope (Leica Microsystems) equipped with a DC300F camera and with an LSM 510 microscope (Carl Zeiss, Jena, Germany), respectively.

Immunohistochemical Staining.

Immuno-histochemical staining of heart tissue sections was performed using the Novolink Kit (Menarini Diagnostics, RE7140-K), as previously described (Ladoire et al., 2012). Briefly, 4 mm-thick formalin-fixed, paraffin-embedded tissue sections were deparaffinized with 3 successive passages through xylene, and rehydrated through decreasing concentrations (100%, 95%, 80%, 70% and 50%) of ethanol. Antigen retrieval was performed by heating slides for 30 min in pH 6.0 citrate buffer at 95° C. Slides were then allowed to cool at room temperature for 45 min, mounted on Shandon Sequenza coverplates (Thermo Fisher Scientific, 72-199-50) in distilled water, and then washed twice for 5 min with 0.1% Tween 20 (v/v in PBS). Thereafter, sections were incubated for 5 min with the Peroxidase Block reagent, and subsequently washed twice for 5 min with 0.1% Tween 20 (v/v in PBS). Following incubation for 5 min at room temperature with the Protein Block reagent, tissue sections were washed twice for 5 min with 0.1% Tween 20 (v/v in PBS), and then incubated overnight at 4° C. with a primary antibody specific for LC3B (clone 5F10, from Nanotools, 0231-100), or with an isotype-matched IgG1 (R&D Systems, MAB002), both dissolved in 1% bovine serum albumin (w/v in TBS) at the final concentration of 25 mg/mL. The 5F10 antibody recognizes both the soluble (LC3-I) and the membrane-bound form (LC3-II) of LC3B. After two washes in 0.1% Tween 20 (v/v in PBS), sections were incubated for 30 min with the Post Primary Block reagent, washed again as before and incubated for 30 min with the horseradish peroxidase-coupled Polymer secondary antibodies. Upon two additional washes, secondary antibodies were revealed with the liquid DAB Substrate Chromogen system (10 min incubation). Finally, slides were washed in distilled water, and counterstained with hematoxylin.

Fluorescence Microscopy.

Confocal fluorescence images were captured using a Leica TCS SP2 confocal fluorescence microscope (Leica Microsystems GmbH, Wetzlar, Germany). For experiments with human cell lines, a Leica APO 63× NA 1.3 immersion objective was used, whereas for the analysis of GFP-LC3 mice tissue sections, a Leica APO 40× NA 1.15 immersion objective was employed. Zeiss Immersol® immersion oil was used for all microscopic analyses. All the acquisitions were done at room temperature with fixed cells/tissue slides. Images were acquired with a Leica DFC 350 Fx camera (version 1.8.0) using Leica LAS AF software and processed with Adobe Photoshop (version CS2) software. Specifically, picture processing involved cropping of representative areas and linear adjustments of contrast and brightness and was performed using Adobe Photoshop (with equal adjustment parameters for all pictures); no explicit gamma correction was used. Non-confocal microscopy of yeast strains carrying the EGFP-tagged Atg8 protein was performed with a Zeiss Axioskop microscope using a Zeiss Plan-Neofluar objective lens with 63× magnification and 1.25 numerical aperture in oil at room temperature. Images were taken with a Diagnostic Instruments camera (Model: SPOT 9.0 Monochrome-6), acquired using the Metamorph software (version 6.2r4, Universal Imaging Corp.) and processed with IrfanView (version 3.97) and Adobe Photoshop (version CS2) software. Specifically, picture processing involved coloring and cropping of representative areas and was performed with InfanView.

Automated Microscopy.

U2OS, HeLa or H4 cells stably expressing GFP-LC3 were seeded in 96-well imaging plates (BD Falcon, Sparks, USA) 24 h before stimulation. Cells were treated with the indicated agents for 4 h. Subsequently, cells were fixed with 4% PFA and counterstained with 10 µM Hoechst 33342. Images were acquired using a BD pathway 855 automated microscope (BD Imaging Systems, San Jose, USA) equipped with a 40× objective (Olympus, Center Valley, USA) coupled to a robotized Twister II plate handler (Caliper Life Sciences, Hopkinton, USA). Images were analyzed for the presence of GFP-LC3 puncta in the cytoplasm by means of the BD Attovision software (BD Imaging Systems). Cell surfaces were segmented and divided into cytoplasmic and nuclear regions according to manufacturer standard proceedings. RB 2×2 and Marr-Hildreth algorithms were used to recognize cytoplasmic GFP-LC3 positive dots. Statistical analyses were implemented on the R software (http://www.r-project.org/). For quantitative analyses of protein acetylation, cell surfaces were segmented into cytoplasm and nuclei regions, and staining intensity of each individual cell was measured for statistical analysis.

Immunoblotting.

For immunoblotting, 25 µg of proteins were then separated on 4-12% Bis-Tris acrylamide (Invitrogen) or 12% Tris-Glycine SDS-PAGE precast gels (Biorad, Hercules, USA) and electrotransferred to Immobilon™ membranes (Millipore Corporation, Billerica, USA). Membranes were then sliced in different parts according to the molecular weight of the protein of interest to allow simultaneous detection of different antigens within the same experiment. Unspecific binding sites were saturated by incubating membranes for 1 h in 0.05% Tween 20 (v:v in TBS) supplemented with 5% non-fat powdered milk (w:v in TBS), followed by the overnight incubation with primary antibodies specific for acetylated-lysine, LC3, phospho-AMPK (Thr172), AMPK, phospho-ribosomal protein S6 kinase (Thr421/Ser424), ribosomal protein S6 kinase, or STQM/p62 (Santa Cruz Biotechnology). Development was performed with appropriate horseradish peroxidase (HRP)-labeled secondary antibodies (Southern Biotech, Birmingham, USA) plus the SuperSignal West Pico chemoluminescent substrate (Thermo Scientific-Pierce). An anti-glyceraldehyde-3-phosphate dehydrogenase antibody (Chemicon International, Temecula, USA) was used to control equal loading of lanes.

Cell Fractionation.

Cells were trypsinized, pelleted at 1000 rpm for 4 min, washed with PBS and pelleted again at 1000 rpm for 4 min. Cells were then resuspended in 5 ml of ice-cold hyposmotic buffer and keep on ice for 5 min. Cells were broken to release nuclei using a pre-chilled Dounce homogenizer (20 strokes with a tight pestle) and then were then centrifuged at 228 g.

Mouse Experiments and Tissue Processing.

C57BL/6 mice (Charles River Laboratory, Lentilly, France) were bred and maintained according to both the FELASA and the Animal Experimental Ethics Committee Guidelines (Val de Marne, France). Mice were housed in a temperature-controlled environment with 12 h light/dark cycles and received food and water ad libitum. For HC-related experiments, mice were injected intraperitoneally with a single 100 mg/kg dose and 6 h later were sacrificed and tissues were immediately frozen in liquid nitrogen. For DCA- and DMKG-related experiments, mice were subjected to 24 h starvation and injected intraperitoneally each 8 h with a 100 mg/kg of either DCA or DMKG solution prepared in PBS. After 24 h of starvation, mice were sacrificed and tissues were immediately frozen in liquid nitrogen after extraction and homogenized two cycles for 20 s at 5,500 rpm using Precellys 24 tissue homogenator (Bertin Technologies, Montigny-le-Bretonneux, France) in a 20 mM Tris buffer (pH 7.4) containing 150 mM NaCl, 1% Triton X-100, 10 mM EDTA and Complete® protease inhibitor cocktail (Roche Applied Science). Tissue extracts were then centrifuged at 12,000 g at 4° C. and supernatants were collected. Protein concentration in the supernatants was evaluated by the bicinchoninic acid technique (BCA protein assay kit, Pierce Biotechnology, Rockford, Ill.). For hydroxycitrate-related weight-loss experiments, autophagy-deficient Atg4b$^{-/-}$ mice were used. Atg4b$^{-/-}$ mice have been previously described (Mariño et al., 2010). For HC-, spermidine-, and resveratrol-related experiments (tumour growth) mice were intraperitoneally injected with respectively 100 mg/kg, 50 mg/kg and 100 mg/kg doses at day 8 and day 9. At day 9, mice were intraperitoneally injected with 2 mg/kg single dose of Mitoxanthrone. For starvation related experiment (tumour growth) mice were treated as previously described (Fabrizio et. al., 2010).

In Vivo Model of Pressure Overload.

Male WT mice (8-10 wk old) were subjected to pressure overload by surgical thoracic aortic constriction (TAC) or sham surgery as described. Animals were injected IP with either vehicle (PBS) or DMOX (300 mg/kg) on the morning of the surgery and daily thereafter. Two-dimensional echocardiography was performed prior to surgery and 1 week post-surgery in non-sedated mice to quantify functional parameters using a Vevo 2100 high-resolution imaging system (Visual Sonics). Mice were sacrificed 1 week post-surgery and hearts isolated for morphological and biochemical analysis. Histological analysis was performed on formalin-perfused, paraffin-embedded sections with H&E and trichrome staining for analysis of fibrosis. Measurement of myocyte cross-sectional area was obtained from a transverse section of LV stained with wheat germ agglutinin. Quantitative analysis was obtained through measurement of an average of 900 cells in each section from two (sham) or three (TAC) animals.

Quantitative Analysis of GFP-LC3 Dots in Mouse Tissue Sections.

To avoid post-mortem autophagy induction, dead mice were immediately perfused with 4% paraformaldehyde (w:v in PBS, pH 7.4). Tissues were then harvested and further fixed with the same solution for at least 4 h, followed by treatment with 15% sucrose (w:v in PBS) for 4 h and with 30% sucrose (w:v in PBS) overnight. Tissue samples were embedded in Tissue-Tek OCT compound (Sakura Finetechnical Co. Ltd., Tokyo, Japan) and stored at −70° C. Five µm-thick tissue sections were prepared with a CM3050 S cryostat (Leica Microsystems GmbH, Wetzlar, Germany), air-dried for 1 h, washed in PBS for 5 min, dried at RT for 30 min, and mounted with VECTASHIELD anti-fading medium. In each organ, the number of GFP-LC3 dots was counted in five independent visual fields from at least five mice using a TCS SP2 confocal fluorescence microscope (Leica Microsystems GmbH).

Preparation of Cytoplasts.

U2OS cells stably expressing GFP-LC3 were trypsinized and incubated in 3 ml of complete medium supplemented with 7.5 mg/mL cytochalasin B for 45 min at 37° C. This cell suspension was layered onto a discontinuous Ficoll density gradient (3 mL of 55%, 1 mL of 90%, and 3 mL of 100% Ficoll-Paques; GE Healthcare) in complete medium containing 7.5 mg/mL cytochalasin B. Gradients were prepared in ultracentrifuge tubes and pre-equilibrated at 37° C. in a CO2 incubator overnight. Gradients containing cell suspensions were centrifugated in a prewarmed rotor (SW41; Beck-man Coulter) at 30,000 g for 30 min at 32° C. The cytoplast-enriched fraction was collected from the interface between 55 and 90% Ficoll layers, washed in complete medium, and incubated for 4 h at 37° C. before treatments.

Sample Preparation for Metabolomic Analytical Measurement.

For in vitro experiments, cell pellets were resuspended in 300 µL of water with HEPES and EDTA (pH 7.4) at 1 mM containing internal standard acetylcoenzyme A (2-$C_{13}$) at 1 mg/L, vortexed and heated at 100° C. for 1 min. Samples were incubated in liquid nitrogen for 1 min and thawed at room temperature two times. They were let for 1 h at −20° C. and centrifuged at 4° C. during 15 min at 13,000 g.

Supernatants were transferred in HPLC vials and injected in HPLC/MS or kept at −80° C. until injection. For in vivo experiments, frozen tissues were placed in ice-cold homogenization tubes containing ceramic beads. Five μL of ice-cold methanol/water (80/20; v/v) were added for 1 mg of tissue. Tissues were homogenized two times for 20 s at 5,500 rpm using Precellys 24 tissue homogenator (Bertin Technologies, Montigny-le-Bretonneux, France). Samples were placed 10 min on ice. Next they were centrifuged at 4° C. during 15 min at 13,000 g. Supernatants were transferred in HPLC vials and injected in HPLC-MS system or kept at −80° C. until injection.

Untargeted Analysis of Intracellular Metabolites by High Performance Liquid Chromatography (HPLC) Coupled to a Quadrupole-Time of Flight (QTOF) Mass Spectrometer.

Profiling of intracellular metabolites was performed on a RRLC 1260 system (Agilent Technologies) coupled to a QTOF 6520 (Agilent) equipped with an electrospray source operating in positive ion and full scan mode from 100 to 1000 Da. The gas temperature was set at 350° C. with a gas flow of 10 L·min$^{1}$. The capillary voltage was set at 4.0 kV, and the fragmentor at 150 V. Two reference masses were used to maintain the mass accuracy during analysis: 121.050873 ($C_5H_4N_4$) and 922.009798 ($C_{18}H_{18}O_6N_3P_3F_{24}$). Five μL of sample were injected on a 150 mm×2.1 mm 3.5 μm SB Aq column (Agilent) with a pre-column 30 mm×2.1 mm 3.5 μm Eclipse plus (Agilent). The gradient mobile phase consisted of water with 10 mmol/L of ammonium acetate and 0.01% of acetic acid (A) and acetonitrile (B). Initial composition of mobile phase was 2% of B, followed by an increase to 95% of B in 10 min. The flow rate was set to 0.3 mL·min$^{-1}$.

Targeted Analysis of AcCoA by HPLC Coupled to a Triple Quadruple (QQQ) Mass Spectrometer.

Targeted analyses were performed on Rapid Resolution Liquid Chromatography (RRLC) 1200SL system (Agilent Technologies, Waldbronn, Germany) coupled to a Triple Quadruple QQQ 6410 mass spectrometer (Agilent Technologies). RRLC analysis was done on 150×2.1 mm, 3.5 μm Eclipse Plus SB-Aq column with a pre-column 30 mm×2.1 mm 3.5 μm Eclipse plus (Agilent Technologies) with water containing 10 mmol/L of ammonium acetate and 0.01% of acetic acid in channel A and acetonitrile in channel B in gradient mode at a flow rate of 0.3 mL·min$^{-1}$: t=0 min 2% B; t=9 min 95% B; t=11 min 95% B; re-equilibration time of 3 min. Mass spectrometer analysis was done in positive electrospray ionization mode at +4 kV on the QQQ system operating in MRM mode. MRM transitions were optimized with standard of AcCoA and AcCoA A 2-C$^{13}$ with direct infusion. Two transitions were recorded for each compound;
- AcCoA 810>303 CE (collision energy) 28V; fragmentor 180V
  810>428 CE 20V
- AcCoA 2-$C_{13}$ 812>305 CE 28V; fragmentor 180V
  812>428 CE 24V for 20 min at 4C to pellet nuclei and other fragments. The supernatant was the cytosolic fraction.

SILAC Cell Culture and Sample Processing.

HCT 116 cells were cultured for two weeks in three different SILAC media (Invitrogen) containing either (i) light isotopes of L-arginine and L-lysine (Arg0/Lys0), (ii) L-arginine-$^{13}C_6$ HCl (Euroisotop) and L-Lysine 2HCl 4,4,5,5-$D_4$ (Euroisotop) (Arg6/Lys4), and (iii) L-arginine-$^{13}C_6$$^{15}N_4$ HCl and L-Lysine $^{13}C_6$$^{15}N_4$ HCl (Invitrogen) (Arg10/Lys8) and complemented as previously described (Blagoev and Mann, 2006). Cells were treated for 4 h with 10 μM rapamycin (Arg10/Lys8) or incubated in Hank's Balanced Salt Solution (NF) (Arg6/Lys4) and then lysed. The lysates were precipitated using ice-cold (−20° C.) acetone (4 volumes of the sample extract), vortexed and placed for 2 h at −20° C. The resulting solution was centrifuged for 10 min at 16,000 g and the supernatant was removed. The pellet was subsequently washed twice with ice-cold 4:1 acetone/water. The final pellet was dried using a SpeedVac (Thermo-Scientific) for 10-15 min. Pellets were dissolved in denaturant 6M/2M urea/thiourea (both from Merck, Darmstadt, Germany) and benzonase (Merck) was added to the nuclear fraction. All steps were performed at RT to avoid carbamoylation of amines. Reduction of cysteines was performed with 5 mM DTT (Sigma-Aldrich) for 30 min followed by alkylation with 11 mM iodoacetamide for 20 min in the dark. The proteins were digested with 1:100 protease LysC (Wako, Neuss, Germany) for 3.5 h, diluted 4 times with 50 mM ammonium bicarbonate and the digested with 1:100 trypsin (Promega, Madison, USA) overnight. The nuclear fraction mixture was centrifuged at 10,000 g for 10 min and the supernatant was filtered through a 0.45 μm MillexHV filter (Millipore). From each fraction ~100 μg digested protein were collected for isoelectric focusing, a step required for subsequent normalization. The acetyl lysine peptide enrichment was performed as previously described (Choudhary et al., 2009). After peptide enrichment and isoelectric focusing, samples were subjected to mass spectrometry analysis and data were processed as described below.

SILAC Sample Processing and Analysis.

Upon digestion, peptides were concentrated and desalted on SepPak C18 (Waters, Milford, USA) purification cartridges and eluted using a highly organic buffer (80% acetonitrile, 0.5% acetic acid). Eluates were lyophilized in a vacuum centrifuge, dissolved in immunoprecipitation buffer (50 mM MOPS pH 7.2, 10 mM sodium phosphate, 50 mM sodium chloride) and mixed with anti-acetyl lysine antibodies conjugated to agarose beads. The mixture was left for 12 h at 4° C. on a rotation wheel. The flow-through (containing non-bound peptides) was removed and beads were washed 4 times with the immunoprecipitation buffer and twice with deionized water. Bead-bound peptides were eluted with 0.1% trifluoroacetic acid. Eluates and 3 separately collected digested protein samples were desalted using SepPak C18 cartridges and 5% of each acetyl lysine-enriched eluate was used for separate mass spectrometric (MS) analysis. Peptides were fractionated according to pI on a strong cation exchange chromatography (SCX) column using a pH step elution gradient as described (Tsonev and Hirsh, 2008). The resulting fractions were then desalted on a C18 Stage-tip as described (Rappsilber and Mann, 2007) prior to MS analysis, which was performed on either an LTQ-Orbitrap-XL (Thermo Sceintific-Pierce, Whaltam, USA) connected to an Agilent 1200 nanoflow HPLC system (Agilent) or an LTQ-Orbitrap-Velos (Thermo Sceintific-Pierce) connected to an Agilent 1100 nanoflow HPLC system (Agilent), using a nanoelectrospray ion source (Thermo Scientific-Pierce). Peptides were separated by reversed phase chromatography using an in-house made fused silica emitter (75 μm ID) packed with Reprosil-Pur C18-AQ 3 μm reversed phase material (Dr. Maisch GmbH, Ammerbuch-Entringen Germany). Peptides were loaded in 98% solvent A (0.5% acetic acid) followed by 100 min linear gradient to 50% solvent B (80% acetonitrile, 0.5% acetic acid). Survey full scan MS spectra (m/z range 300-200, resolution 60.000 @m/z 400) were acquired followed by fragmentation of the 10 (in case of using the LTQ-Orbitrap-XL) or the 20 (in case of using the LTQ-Orbitrap-Velos) most intense multiply charged ions. Ions selected for MS/MS were placed on a dynamic exclusion list for 45 sec. Real-time internal lock mass recalibration was used during data acquisition (Rappsilber and Mann, 2007). For unfractionated acetyl lysine-enriched eluates an additional MS analysis was performed on the LTQ-Orbitrap Velos using HCD fragmentation (normalized collision energy of 40) of the 10 most intense ions from each MS spectrum creating MS/MS spectra at resolution 7500. All samples used for protein normalization were analyzed on an LTQ FT ULTRA mass spectrometer (Thermo Finnigan, Ringoes, USA) where the 5 most intense ions from each precursor scan were selected for fragmentation in the LTQ. In this case, no real-time lock mass recalibration was used. Reverse phase chromatography settings were the same as described for the analysis done on the Orbitrap spectrometers.

SILAC Data Processing.

Raw files were processed with MaxQuant v. 1.1.1.14 (Cox and Mann, 2008) into centroided data and submitted to database searching using the Andromeda search algorithm (Cox et al., 2011). Pre-processing by MaxQuant was performed to determine charge states, miscleavages and SILAC states and to filter the MS/MS spectra keeping the 6 most intense peaks within a 100 Da bin. Cysteine carbamidomethyl was chosen as fixed modification while N-termini acetylation and methionine oxidation were chosen as variable modifications. Furthermore, acetylation of light, medium and heavy isotope lysines (Lys0/Lys4/Lys8) was chosen as variable modification. Processed MS/MS spectra were searched against a concatenated target-decoy database of forward and reversed sequences from the IPI database (152616 sequences, FASTA file created 20080506). For the search Trypsin/P+DP was used for the in silico protein digestion allowing 4 miscleavages. The mass tolerance for the MS spectra acquired in the Orbitrap was set to 7 ppm whereas the MS/MS tolerance was set to 0.6 Da for the CID MS/MS spectra from the LTQ and to 0.04 Da for the HCD MS/MS spectra. Upon peptide search, protein and peptide identification was performed given an estimated maximal false discovery rate (FDR) of 1% at both the protein and peptide level. For FDR calculation, posterior error probabilities were calculated based on peptides of at least 6 amino acids having an Andromeda score of at least 30. For protein quantification only unmodified peptides and peptides modified by N-termini acetylation (N-term) and methionine oxidation (M). If a counterpart to a given lysine acetylated peptide was identified, this counterpeptide was also excluded by protein quantitation. According to the protein group assignment performed by MaxQuant, both razor and unique peptides are used for protein quantification. A minimum of two ratio counts was required for protein quantification. For quantification of lysine-acetylated sites the least modified peptides were used. The ratios for the sites were normalized by the corresponding protein ratios to account for eventual changes in protein abundance. In case a protein ratio was not determined, normalization was based on a logarithm-transformation algorithm as previously described (Cox et al., 2011).

Statistical Analysis.

Unless otherwise mentioned, experiments were performed in triplicate and repeated at least twice. Data were analyzed using the GraphPad Prism 5 software and statistical significance was assessed by means of two-tailed Student's t or ANOVA tests, as appropriate.

EXAMPLE 2

Results:

Inhibition of Autophagy by Acetyltransferases and Acetylproteins.

One of the best-studied physiological inducers of autophagy is energy depletion, as it results from exposing cells to nutrient-free media or by subjecting mice to starvation (Mizushima and Komatsu, 2011). Mass spectrometric metabolomic profiling of starved cells (in vitro) or organs (in vivo) revealed the intracellular depletion of very few common metabolites including acetyl CoA (AcCoA). Starvation-induced AcCoA depletion could be confirmed in murine and human cell lines, both in total cellular homogenates and cytosolic fractions, with a stronger effect observed in the latter. Interestingly, the starvation-induced decrease of AcCoA was not accompanied by the depletion of neither ATP nor NADH at the analyzed incubation times. In mice, heart and muscle tissues respond to nutrient depletion by mounting a strong autophagic response (Mizushima et al., 2004), which we found to be commensurated with a drastic reduction in AcCoA levels accompanied by a significant decrease in cytoplasmic protein acetylation. In contrast, brain tissue, in which autophagy induction is not observed after fasting (Mizushima et al., 2004), presented no alterations in AcCoA levels or protein acetylation even after prolonged (48 h) starvation.

Starved cells exhibited a preponderant deacetylation of their proteins, as determined by SILAC technology. Starvation-induced protein deacetylation of the majority of cellular proteins was confirmed by immunoblot analyses, although some proteins like tubulin were hyperacetylated after starvation (Geeraert et al., 2010; Hamai and Codogno, 2012; Lee et al., 2010)., as detected by immunoblotting and confirmed by immunofluorescence staining. We developed a protocol in which plasma membranes but not nuclear envelopes were permeabilized (Pietrocola et al., 2012) acetylated tubulin was blocked with a specific antibody, and an antibody specific for acetylated lysines was revealed by immunofluorescence. Using this simple method, we could detect starvation-induced deacetylation of cytoplasmic proteins in multiple distinct cell lines. These results suggest that AcCoA depletion is linked to the deacetylation of cytoplasmic proteins.

Cells harbor multiple acetyltransferases and deacetylases that control the acetylation of nuclear and cytoplasmic proteins as they consume AcCoA and generate acetate, respectively (Hassig et al., 1997; Katan-Khaykovich and Struhl, 2002; Nakamura et al., 2010). To date, 78 acetyltransferases and 20 distinct deacetylases have been annotated in the human genome. Among these acetyltransferases, we chose 44 whose localization is not strictly restricted to the nucleus or whose known activity is not limited to specific processes such as meiosis or chromatin remodeling. Knockdown of most of these 44 acetylases led to the induction of autophagic GFP-LC3 puncta, reflecting the incorporation of LC3 into autophagosomal membranes. This autophagy induction occurred both in the absence and in the presence of the lysosomal inhibitor bafilomycin A1 (BafA1), which allows for accurate measurement of autophagic flux (Rubinsztein et al., 2009). Thus, the aggregate of all siRNAs targeting acetyltransferases induced significant GFP-LC3 puncta, as compared to scrambled control siRNAs.

Inhibition of acetyl transferases by broad-spectrum inhibitors including anacardic acid, garcinol, curcumin or 3-methylbutyrolactone (3-MB), elicited a marked increase in GFP-LC3 puncta, both in the absence and in the presence BafA1. In contrast, knockdown of the 20 known deacetylases failed to affect autophagy in a significant fashion. These results suggest that acetyltransferases (but less so deacetylases) participate in the physiological repression of autophagy. Consistently, knockdown of individual proteins that are commonly acetylated during autophagy induction (Morselli et al., 2011) often stimulated autophagy, whereas the depletion of proteins that are commonly deacetylated in autophagy usually failed to do so. Statistical analyses indicated that, in aggregate, acetylated (but not deacetylated) proteins function as autophagy repressors. These results are in line with the interpretation that the baseline activity of protein acetyltransferases (which transfer acetyl groups from AcCoA to the ε-amino group of accessible lysine residues on protein substrates) is more important for controlling autophagy than that of deacetylases. We conclude that conditions resulting in AcCoA depletion, inhibition of acetyltransferases, and deacetylation of cytoplasmic proteins can result in autophagy induction.

Inhibition of Autophagy by AcCoA.

Similar to mammalian cells, starved yeast cells exhibited AcCoA depletion and concomitant autophagy induction. In yeast, the most important enzyme involved in cytosolic AcCoA biogenesis is AcCoA synthase-2 (ACS2) (Takahashi et al., 2006). Overexpression of ACS2 was sufficient to keep high AcCoA levels in spite of starvation and efficiently inhibited autophagy. In mammalian cells, AcCoA is mainly produced in mitochondria and shuttled to the cytoplasm in the form of citrate, where it is converted back to AcCoA by the enzyme ATP-citrate lyase (ACLY) (Wellen et al., 2009). Based on these premises, we next asked whether increasing intracellular AcCoA concentrations by genetic or pharmacological manipulations of the main cellular pathways involved in AcCoA generation would be sufficient to inhibit starvation-induced autophagy.

One of the main sources of cellular AcCoA is pyruvate decarboxylation, which is catalyzed by the pyruvate dehydrogenase (PDH) complex. The activity of the PDH complex is tightly regulated by a product-dependent feedback loop and by inhibitory phosphorylation by the pyruvate dehydrogenase kinase (PDK) isoenzymes (PDK1, 2, 3, and 4) (Roche and Hiromasa, 2007). In fact, PDK2 and PDK4 cellular levels are increased during starvation, which leads to a reduction in PDH complex activity, coupling pyruvate decarboxylation to cellular energetic status (Jeong et al., 2012). Thus, we explored whether maintenance of high PDH activity during starvation would result in increased AcCoA levels, which in turn might inhibit autophagy. Knockdown of PDK2 or PDK4 inhibited both starvation-induced AcCoA depletion and autophagy, as measured by two assays (LC3 distribution to cytoplasmic puncta and LC3 lipidation detectable by immunoblot). Starvation-induced autophagy inhibition by PDK2/4 knockdown was accompanied by a reversion of starvation-associated mTORC1 inhibition and AMPK activation. Similarly, pharmacological inhibition of PDKs with dichloroacetate (DCA) resulted in the suppression of starvation-induced AcCoA depletion, protein deacetylation, mTORC1 inhibition, AMPK activation and autophagy, both in vitro, in starved human cells, and in vivo, in the heart (skeletal muscle and liver (not shown) from starved mice. Moreover, stimulation of PDH activity by its cofactor lipoic acid (LA) (Zachar et al., 2011) allowed mammalian cells to maintain high AcCoA and cytoplasmic acetylation levels, even in conditions of nutrient and serum depletion, as it blunted starvation-induced mTORC1 inhibition, AMPK activation and autophagy flux.

In addition to pyruvate, branched-chain amino-acids (BCAAs) can constitute an alternative source of AcCoA for mammalian cells. BCAAs can be transaminated to branched-chain α-ketoacids (BCKAs), which subsequently undergo a multi-step reaction comparable to the decarboxylation of pyruvate. This irreversible reaction is catalyzed by the mitochondrial branched-chain α-ketoacid dehydrogenase complex (BCKDH), yielding AcCoA as the end product (Chuang, 2013; Navarro et al., 2008). Supplementation of leucine (the most bioactive BCAA) was sufficient to maintain high AcCoA levels and cytoplasmic protein acetylation during nutrient and serum deprivation, correlating with the suppression of autophagy. Leucine can be transaminated to a-ketoisocaproic acid (KIC), also known as keto-leucine, which is subsequently oxidized to AcCoA (Harper et al., 1984). Addition of KIC was sufficient to avoid AcCoA depletion and protein deacetylation in starved cells, as it prevented starvation-associated mTORC1 inhibition and AMPK activation. Concomitantly, KIC inhibited the starvation-induced increase in autophagic flux and turnover of long-lived proteins. On a molar basis, KIC (which barely increased intracellular leucine levels, as determined my mass spectrometry) was more efficient than leucine in suppressing autophagy. Moreover, depletion of the BCKDH E1α subunit (BCKDHA) inhibited the conversion of KIC into AcCoA as it abolished the KIC-mediated suppression of starvation-induced autophagy. These findings support the contention that KIC inhibits autophagy through its conversion into AcCoA rather than by replenishing amino acids.

Consistent with the effects of KIC, the short chain fatty acid butyrate, which can also be catabolized to AcCoA (Donohoe et al., 2012), maintained high cytosolic AcCoA, increased protein acetylation and inhibited autophagic flux, when supplemented to starved mammalian cells. Thus, rather different strategies to replenish AcCoA levels can avoid starvation-induced autophagy. Following these lines, supplementation of dimethyl-a-ketoglutarate (DMKG), a cell-permeant precursor of α-ketoglutarate (Willenborg et al., 2009), also maintained high AcCoA and cytoplasmic acetylation levels and low autophagy (linked to a coordinated modulation of mTORC1 and AMPK pathways activity) under starvation conditions in vitro. DMKG supplementation failed to enhance intracellular amino acid levels in starved cells, contrasting with the observation that equimolar concentrations of glutamine (which was used as a control) did increase cellular glutamate levels. This implies that the autophagy-inhibitory effect of DMKG cannot be secondary to effects on amino acid metabolism. Depletion of both isocitrate dehydrogenase isoforms (IDH1 and IDH2) abolished the ability of DMKG to replenish cytosolic AcCoA levels as well as its anti-autophagic function. These results suggest that DMKG-derived α-ketoglutarate undergoes reductive carboxylation to isocitrate, followed by IDH1/2-mediated isomerization to the AcCoA precursor citrate. Beyond these in vitro effects, DMKG efficiently reduced autophagy in vivo, in mice. Parenteral administration of DMKG to starved mice avoided the depletion of AcCoA, the deacetylation of cytosolic proteins, as well as fasting-induced autophagy in heart and skeletal muscles (not shown). Moreover, DMKG inhibited the maladaptive accumulation of autophagosomes induced by cardiac pressure overload following surgical thoracic aortic constriction (TAC). Repeated injections of DMKG suppressed multiple features of TAC-induced heart failure, namely cardiomyocyte hypertrophy, cardiac hypertrophy, left ventricular dilatation, cardiac muscle fibrosis, and reduced contractile performance measured as ejection fraction or fractional shortening. Thus, suppression of maladaptive autophagy by increasing AcCoA levels can blunt afterload-induced pathological cardiac remodeling, confirming previously reported beneficial effects of genetic autophagy inhibition in this model (Cao et al., 2013; Zhu et al., 2007).

It should be noted that none of the AcCoA-replenishing agents (DCA, LA, KIC, butyrate or DMKG) was capable of increasing cellular ATP levels in starved cells. Rather, such agents induced a decrease in cellular ATP, which may be attributed to autophagy inhibition, as treatment with the autophagy inhibitor 3-methyladenine (3-MA) similarly reduced ATP content and autophagy-deficient $Atg5^{-/-}$ or $Atg7^{-/-}$ MEFs contained lower cellular ATP levels than WT MEFs (Lin et al., 2012b). These results suggest that an increase in cellular AcCoA levels is sufficient to counteract autophagy induction by nutrient and serum deprivation. Moreover, pharmacological and metabolic manipulations designed to increase AcCoA were capable of suppressing autophagy induced by clinically relevant compounds including metformin, rotenone, Akt inhibitors and rapamycin. Thus, AcCoA acts as broad-spectrum autophagy repressor, well beyond its capacity to inhibit starvation-induced autophagy.

Induction of Autophagy by AcCoA Depletion.

To further characterize the role of AcCoA in autophagy regulation, we addressed the question as to whether a reduction in AcCoA levels would be sufficient to increase autophagic activity, even in cells that are kept in rich medium. Before it can be converted to AcCoA, pyruvate has to be transported across the inner mitochondrial membrane by the mitochondrial pyruvate carrier complex (MPC) (Herzig et al., 2012). Knockdown of MPC or its pharmacological inhibition by the α-cyanocinnamate derivative UK5099 led to the depletion of intracellular AcCoA. AcCoA depletion was coupled to deacetylation of cytoplasmic proteins, induction of GFP-LC3 puncta and lipidation of endogenous LC3-I to LC3-II, both in the presence or absence of BafA1, confirming an increase of autophagic flux. AcCoA depletion also increased the autophagy-dependent turnover of long-lived proteins. Consistently, transfection-enforced overexpression of several pyruvate dehydrogenase kinase (PDK) iso forms, which as mentioned above catalyze the inhibitory phosphorylation of PDH, also led to a reduction in both AcCoA levels and cytoplasmic protein acetylation, together with an increase of autophagic flux and autophagy-dependent protein degradation. In addition to pyruvate decarboxylation, cells may use fatty acid-oxidation to generate AcCoA Inhibition of mitochondrial carnitine palmitoyltransferase-1 (CPT1), the rate-limiting enzyme in fatty acid-oxidation, by perhexiline (PHX) (Foster, 2004; Kennedy et al., 1996), reduced AcCoA cellular levels and induced signs of autophagy. Similarly, knockdown of CPT1c, a CPT1 isoform highly expressed in human cancer cells (Zaugg et al., 2011), stimulated autophagic flux in U2OS osteosarcoma cells.

Interestingly, all the interventions shown to induce autophagy by depleting AcCoA were accompanied by both mTORC1 inhibition (as measured by a reduction in the phosphorylation of its substrate $p70^{s6k}$) and AMPK stimulation, indicating that the activity of autophagy-regulatory pathways is coupled to AcCoA levels. None of the manipulations decreasing cellular AcCoA led to a reduction in ATP levels, indicating that AcCoA depletion can stimulate autophagy in a context of high ATP. Moreover, mitochondrial outer membrane permeabilization (MOMP) was not induced with any of the treatments reducing cellular AcCoA, excluding the possibility that the detected increase in autophagic flux is a consequence of toxic mitochondrial stress. Depletion of AcCoA was not cytotoxic and actually prevented cell death induced by transgenic Q74 huntingtin (Williams et al., 2008) (Pankiv et al., 2007), consistent with the reported cytoprotective action of conventional autophagy inducers (Rubinsztein et al., 2007). We therefore conclude that the interruption of glycolytic and lipolytic AcCoA generation in mitochondria, via inhibition of MCP or CPT1, respectively, can induce cytoprotective autophagy.

Regulation of Autophagy by Cytosolic AcCoA.

Acetylation affects the function of cellular proteins in multiple organelles including nuclei, the endoplasmic reticulum or mitochondria (Hebert et al., 2013; Masri et al., 2013; Pehar et al., 2012; Wellen et al., 2009), implying that AcCoA levels might regulate autophagy in specific cellular compartments. In mammalian cells, cytosolic AcCoA is mostly generated from citrate, which is transported from mitochondria to the cytosol by the mitochondrial citrate carrier (CiC). Once in the cytosol, citrate is converted back to oxaloacetate and AcCoA by the ATP citrate lyase (ACLY) (Wellen et al., 2009). Based on these premises, we analyzed whether cytoplasmic AcCoA reduction would be sufficient to increase autophagic flux Inhibition of CiC by the substrate analogue 1,2,3-benzenetricarboxylate (BTC), as well as by direct knockdown of ACLY, induced the triad of AcCoA depletion (measured specifically in the cytosolic, organelle-free fraction), protein deacetylation and autophagy. Consistently, addition of hydroxycitrate (HC), a competitive inhibitor of ACLY (Lowenstein and Brunengraber, 1981; Watson et al., 1969), also reduced cytoplasmic AcCoA levels, induced cytosolic protein deacetylation and strongly stimulated autophagy both in vitro and in vivo. Prolonged treatment of mice with hydroxycitrate is known to cause significant weight loss (Onakpoya et al., 2011), and this effect was only observed for autophagy-competent wild type mice, not for autophagy-deficient $atg4b^{-/-}$ mice (Mariño et al., 2010), underlining the impact of autophagy in the in vivo pharmacology of hydroxycitrate. Oral administration of hydroxycitrate to WT mice for two days triggered a systemic autophagic response comparable to that induced by starvation yet provoked a less drastic weight loss and had no impact on food intake. However, hydroxycitrate enhanced the tumor growth-inhibitory effect of chemotherapy as efficiently as did starvation (Lee et al., 2012), underscoring the potential therapeutic utility of this compound. Moreover, the administration for two days of others two well-known autophagy inducers, spermidine and resveratrol, was capable to recapitulate the positive combinatorial effect of starvation and the antrhacenedione mitoxanthrone in a tumor growth experiment.

Although cytosolic AcCoA in mammalian cells is mostly generated from citrate via ATP-citrate lyase (ACLY) (Wellen et al., 2009; Wellen and Thompson, 2012), an alternative potential source of cytosolic AcCoA is acetate, as a result of the catalytic activity of acyl-CoA synthetase short-chain family member 2 (ACCS2) (Wellen et al., 2009; Wellen and Thompson, 2012). Knockdown of ACCS2 induced the triad of cytosolic AcCoA depletion, protein deacetylation and autophagy induction. The downregulation of the yeast ACCS2 orthologue, ACS2, also led to a reduction of cellular AcCoA concentrations that was accompanied by an increase in autophagy. Altogether these results indicate that cytosolic AcCoA depletion stimulates autophagy in a phylogenetically conserved fashion.

Depletion of cytosolic AcCoA was accompanied by an increase in AMPK phosphorylation and a decrease in mTORC1 activity (as measured by $p70^{s6k}$ phosphorylation).

Importantly, mitochondrial citrate carrier inhibition by BTC or ACLY inhibition by HC cancelled the inhibitory effects of the PDH activator DCA, the a-ketoglutarate precursor DMKG or the leucine derivate KIC on starvation-induced protein deacetylation and autophagy. This supports the idea that the cytosolic (not the mitochondrial) pool of AcCoA regulates the activity of acetyltransferases and ultimately modulates autophagic flux. Consistent with this notion, all treatments that increased total cellular AcCoA levels (DCA, LA, DMKG, KIC and UK 5099) also raised the cytosolic concentration of AcCoA, thus reinforcing the link between cytosolic AcCoA levels and autophagy regulation. To directly assess the impact of cytosolic AcCoA on autophagy, starved U2OS cells stably expressing GFP-LC3 were microinjected with AcCoA together with dextran red to visualize injected cells. Injection of AcCoA (but not that of CoA) into the cytoplasm of starved cells increased the levels of cytoplasmic protein acetylation and simultaneously reduced starvation-induced autophagic flux. This experiment provides direct evidence in favor of the idea that cytosolic AcCoA represses autophagy.

Through nuclear pores, cysolic AcCoA can freely diffuse into the nucleus (Wellen and Thompson, 2012). Thus, through its effects on the acetylation of histone and other chromatin binding factors, the combined nucleo-cytosolic pool of AcCoA might affect gene transcription programs (Shi and Tu, 2013), which in turn could impinge on autophagy (Pietrocola et al., 2013). To evaluate this possibility, we experimentally enucleated GFP-LC3-expressing cells and exposed the resulting cytoplasts to AcCoA modulating conditions in the presence of BafA1 to measure autophagic flux in the absence of nuclei. AcCoA depleting agents (BTC, HC, UK5099) stimulated autophagy in cytoplasts as efficiently as in nucleated control cells. Moreover, starvation-induced autophagy was fully induced in cytoplasts and was indistinguishably repressed by AcCoA replenishing agents in cytoplasts and cells. These results indicate that short-term alterations in cytosolic AcCoA concentrations can regulate autophagy through purely cytoplasmic (non-nuclear) effects.

Discussion:

Here we report that depletion of several dozens of acetyltransferases induced autophagy in human cells, while inhibition of deacetylases had no such effect. Moreover, depletion of multiple proteins that are hyperacetylated upon autophagy-inducing treatments (but not that of hypoaccylated proteins) stimulated autophagy, indicating that acetyltransferases and their products usually repress autophagy. We observed by metabolomic analyses that starvation-induced AcCoA depletion precedes that of ATP or NADH. AcCoA depletion entailed the commensurate reduction in the overall acetylation of cytoplasmic proteins, as well as the induction of autophagy. Multiple distinct manipulations designed to increase or reduce intracellular AcCoA led to the suppression or induction of autophagy, respectively, in mice, cultured human cells, or yeast. Thus, the inhibition of AcCoA synthesis by interventions on pyruvate, acetate, branced-chain amino-acids and fatty acid metabolism induced autophagy, while stimulation of AcCoA synthesis inhibited autophagy induced by multiple distinct stimuli.

At variance with kinases, which operate close-to-independently from ATP concentrations (due to their high $K_d$ for ATP), acetyltransferases are profoundly influenced in their catalytic activity by the availability of acetyl groups, provided by AcCoA. Thus, subtle differences in AcCoA levels may impact on the level of overall protein acetylation, which reflects the compounded activity of acetyltransferases and deacetylases (Wellen and Thompson, 2012). As a caveat, it should be mentioned that the acetylation of specific proteins (contrasting with the overall de-acetylation of most proteins) is linked to autophagy induction. This is exemplified by the reported pro-autophagic Esa1p/T1P60-mediated hyperacetylation of Atg3p in yeast (Yi et al., 2012) or ULK1 in human cells (Lin et al., 2012a), both of which occur at least transiently in response to starvation. However, these specific reactions contrast with an overall pattern indicating that AcCoA-dependent protein acetylation represses autophagy. Starvation can induce the Sirtuin-1-induced deacetylation of essential autophagy proteins including ATG5, ATG7, ATG12 and LC3 (Lee et al., 2008; Lee and Finkel, 2009), the HDAC6-mediated deacetylation of cortactin, (Lee et al., 2010) as well as the HDAC1-mediated deacetylation and activation of PRRKA1 (a subunit of AMPK), which is counteracted by the acetyltransferase EP300 (Lin et al., 2012c). This latter mechanism may explain the tight coupling of intracellular AcCoA levels to the phosphorylation/activation status of AMPK and mTOR that we observed here. Moreover, these deacetylation reactions are likely to contribute to the ignition and completion of autophagy, yet cannot explain all details of its regulation, as indicated by the implication of multiple additional acetyl transferases and acetylated proteins in the control of autophagy. Thus, the TORC1-inhibitor rapamycin failed to re-induce autophagy upon AcCoA increasing treatments. Likewise, MEFs lacking the AMPK subunits PRKAA1 and PRKAA2 still responded to starvation and AcCoA depletion/increase by an increase/reduction in autophagic flux, supporting some redundancy in the acetylation-dependent control of autophagy.

Activation of deacetylases and inhibition of acetyltransferases by resveratrol and spermidine, respectively, can stimulate the deacetylation of cellular proteins accompanied by the induction of autophagy (Eisenberg et al., 2009). As shown here, depletion of AcCoA can induce autophagy and modulate intersecting autophagy-regulatory pathways in conditions in which the intracellular levels of ATP, NADH or free amino acids such as leucine or glutamate are not affected. We observed that experimentally induced AcCoA depletion by inhibition of the glycolytic or lipolytic pathways, suppression of the mitochondrial export of AcCoA or inhibition of cytosolic AcCoA synthase, was sufficient to stimulate autophagy. Conversely, prevention of starvation-induced AcCoA depletion by inhibition of PDKs (or in yeast by overexpression of ACS2) or replenishment of AcCoA pools (by microinjection of AcCoA itself or by administration of AcCoA precursors including butyrate, DMKG and KIC) was able to inhibit autophagy in vitro and in vivo. Therefore, we postulate that AcCoA functions as a metabolic regulator of autophagy that impinges on the acetylation of multiple autophagy-regulatory proteins through a multi-pronged effect.

The depletion of energy-rich metabolites is a strong inducer of autophagy. As an example, an unfavorable shift in the ratio between ATP and AMP causes activation of AMPK, which phosphorylates multiple substrates in the cardinal autophagy regulators, including the ULK1, mTORC1 and Beclin 1 complexes (Kim et al., 2013). Moreover, depletion of NADH causes the activation of sirtuin 1 and other sirtuins with autophagy-stimulatory consequences (Jang et al., 2012). AMPK and sirtuin 1 can cooperate in autophagy induction, forming a cooperative switch for the rapid adaptation of cells to dwindling energy sources (Canto et al., 2009; Hou et al., 2008; Lan et al., 2008; Ruderman et al., 2010). Notwithstanding the importance of ATP/AMPK and NADH/sirtuin, our results point to the existence of an additional control instance, cytosolic AcCoA. Indeed, at early time points of starvation, intracellular AcCoA was found reduced well before ATP depletion or NADH oxidation became detectable. However, it appears plausible that ATP, NADH and AcCoA-regulated processes are closely interconnected, based on multiple pathways that link energy homeostasis among these molecules, as well as on the facts that AMPK is itself a substrate of (de)acetylation (Lin et al., 2012c), phosphorylates the acetylase EP300 (Yang et al., 2001), and closely cooperates with the deacetylase sirtuin 1 (Kroemer et al., 2010; Ruderman et al., 2010). In accord with this postulated interconnectivity, artificial depletion or replenishment of AcCoA was accompanied by the activation or inhibition of AMPK, as well as the mirror-like inhibition or activation of mTORC1. Nonetheless, cells cultured in nutrient- and serum-free media during short time periods (2 to 6 h) manifested a depletion of cytosolic AcCoA and amino acids (but not ATP). AcCoA-replenishing agents (such as DCA, DMKG, KIC, LA) solely restored AcCoA but not amino acids (and actually reduced ATP) as they suppressed starvation-induced autophagy. Taken together, these results support the idea that AcCoA may control autophagy in a way that is independent from amino acids and ATP.

One of the major metabolic consequences of autophagy is an increase in AcCoA pools (Rabinowitz and White, 2010), suggesting a negative feedback circuitry that is controlled by AcCoA and that warrants further investigation. Chronic elevation of AcCoA by excessive caloric intake may suppress autophagy, thereby accelerating the manifestation of age-associated pathologies. In contrast, dietary and pharmacological manipulations causing a decrease in AcCoA might ameliorate our health by stimulating autophagy. In this context, it appears intriguing that hydroxycitric acid, an anti-obesity agent (Onakpoya et al., 2011), enhances autophagic flux, which in turn is required for body weight reduction. In contrast, several components used to experimentally stimulate weight gain such as DMKG or KIC (Campbell et al., 2006; Zanchi et al., 2011) were found to strongly inhibit autophagy.

Altogether, the present data unravel a whole range of metabolic and pharmacological manipulations that, by targeting AcCoA, allow for the induction or suppression of autophagy irrespective of the nutritional status. This strategy may lead to the identification of therapeutically useful autophagy modulators, as exemplified by AcCoA-replenishing agents that suppress maladaptive autophagy in a model of cardiac pressure overload and AcCoA-depleting agents that improve anticancer chemotherapy in vivo and confer cytoprotection in a model of neurodegeneration-associated cell death.

EXAMPLE 3

Results:

Starvation Induces Depletion of Acetyl-CoA and Protein Deacetylation

Autophagy can be potently induced by exposing cells to nutrient-free media or by subjecting mice to starvation (Mizushima and Komatsu, 2011). Mass spectrometric metabolomic profiling of starved cells (in vitro) or organs (in vivo) revealed the intracellular depletion of very few common metabolites, one of which was AcCoA. Starvation-induced AcCoA depletion could be confirmed in murine and human cell lines, both in total cellular homogenates and in cytosolic fractions. At the analyzed short (<6 hr) incubation times, the starvation-induced decrease of AcCoA was not accompanied by the depletion of ATP or NADH. In mice, heart and muscle tissues responded to nutrient depletion by mounting a strong autophagic response (Mizushima et al., 2004), which we found to be commensurate with a reduction in AcCoA levels and a decrease in cytoplasmic protein acetylation. In contrast, brain tissue, in which autophagy induction is not observed after fasting (Mizushima et al., 2004), presented no alterations in AcCoA levels or protein acetylation even after prolonged (48 hr) starvation.

Starved cells exhibited a preponderant deacetylation of their proteins, as determined by SILAC technology. Global deacetylation of the majority of cellular proteins was confirmed by immunoblot analyses, although some proteins like tubulin were hyperacetylated after starvation (Geeraert et al., 2010 and Lee et al., 2010). For the rapid evaluation of the global acetylation status of cytoplasmic proteins, we developed a protocol in which plasma membranes but not nuclear envelopes were permeabilized (Pictrocola et al., 2012), acetylated tubulin was blocked with a specific antibody, and antibody staining of proteins with acetylated lysines was revealed by immunofluorescence. Using this method, we could detect starvation-induced deacetylation of cytoplasmic proteins. These results suggest that AcCoA depletion is linked to the deacetylation of cytoplasmic proteins.

Maintaining AcCoA Levels During Starvation Inhibits Autophagy Induction

AcCoA is produced in mitochondria by three major pathways, namely pyruvate decarboxylation, fatty acid oxidation, and the catabolism of branched-chain amino acids (BCAAs) (Wellen et al., 2009).

Pyruvate decarboxylation is catalyzed by pyruvate dehydrogenase (PDH), which is negatively regulated by pyruvate dehydrogenase kinase (PDK) isoenzymes (PDK1, PDK2, PDK3, and PDK4) (Roche and Hiromasa, 2007). Knockdown of PDK2 or PDK4 inhibited both starvation-induced AcCoA depletion and autophagy, as measured by two assays (GFP-LC3 distribution to cytoplasmic puncta and LC3 lipidation detectable by immunoblot, both in the presence/ absence of the lysosomal inhibitor bafilomycin A1, BafA1, to measure autophagic flux) but had no significant effect on cellular ATP content. Starvation-induced autophagy inhibition by PDK2/4 knockdown was accompanied by a reversion of starvation-associated mTORC1 inhibition and AMPK activation. Similarly, pharmacological inhibition of PDKs with dichloroacetate (DCA) resulted in the suppression of starvation-induced AcCoA depletion (but not in an increase of ATP levels), protein deacetylation, mTORC1 inhibition, AMPK activation, turnover of long-lived proteins, and autophagic flux, both in vitro, in starved human cells, and in vivo, in the heart, skeletal muscle, and liver (data not shown) from starved mice. Direct stimulation of PDH activity by its cofactor lipoic acid (LA) (Zachar et al., 2011) also allowed starved cells to maintain high AcCoA and cytoplasmic acetylation levels, as it blunted starvation-induced mTORC1 inhibition, AMPK activation, turnover of long-lived proteins, and autophagic flux.

BCAAs (such as leucine) are transaminated to branched-chain α-ketoacids (such as, in the case of leucine, a-ketoisocaproic acid, KIC), which subsequently undergo oxidative decarboxylation, yielding AcCoA as the end product. This irreversible reaction is catalyzed by the mitochondrial branched-chain α-ketoacid dehydrogenase complex (BCKDH) (Chuang, 2013). Supplementation of leucine, the most bioactive BCAA, was sufficient to maintain high AcCoA levels and cytoplasmic protein acetylation during nutrient deprivation, correlating with the suppression of autophagy. Addition of KIC was sufficient to avoid AcCoA depletion and protein deacetylation in starved cells, as it prevented starvation-associated mTORC1 inhibition and AMPK activation. Concomitantly, KIC inhibited the starvation-induced increase in autophagic flux and turnover of long-lived proteins. On a molar basis, KIC (which barely increased intracellular leucine levels, as determined my mass spectrometry) was more efficient than leucine in suppressing autophagy. Depletion of BCKDH E1α subunit (BCKDHA) inhibited the conversion of KIC into AcCoA as it abolished the KIC-mediated suppression of starvation-induced autophagy. In contrast, BCKDHA depletion did not abolish the slight increase in intracellular leucine concentrations induced by KIC supplementation. Altogether, these findings support the contention that KIC inhibits autophagy through its conversion into AcCoA rather than by replenishing amino acids.

When supplemented to starved cells, the short-chain fatty acid butyrate, which can be catabolized to AcCoA (Donohoe et al., 2012), maintained high cytosolic AcCoA, increased protein acetylation, and inhibited autophagic flux. Supplementation of dimethyl-α-ketoglutarate (DMKG), a cell-permeant precursor of α-ketoglutarate (Willenborg et al., 2009), also maintained high AcCoA and cytoplasmic acetylation levels and low autophagy (linked to a coordinated modulation of mTORC1 and AMPK pathways activity) under starvation conditions in vitro. DMKG supplementation failed to enhance intracellular amino acid levels in starved cells. Simultaneous depletion of both isocitrate dehydrogenase isoforms (IDH1 and IDH2) abolished the ability of DMKG to replenish cytosolic AcCoA levels as well as its antiautophagic function. These results suggest that DMKG-derived α-ketoglutarate undergoes reductive carboxylation to isocitrate, followed by IDH1/2-mediated isomerization to the AcCoA precursor citrate.

Beyond these in vitro effects, DMKG efficiently reduced autophagy in vivo. Parenteral administration of DMKG to starved mice avoided the depletion of AcCoA and the deacetylation of cytoplasmic proteins, as well as fasting-induced autophagy in heart and skeletal muscles. Moreover, DMKG inhibited the maladaptive accumulation of autophagosomes induced by surgical thoracic aortic constriction (TAC). Repeated DMKG injections suppressed multiple features of TAC-induced heart failure, namely cardiomyocyte hypertrophy, left ventricular dilatation, cardiac muscle fibrosis, and reduced contractile performance. Thus, suppression of maladaptive autophagy by increasing AcCoA levels can blunt pressure overload-induced cardiomyopathy, confirming the beneficial effects of genetic autophagy inhibition in this pathology (Zhu et al., 2007).

It should be noted that none of the AcCoA-replenishing agents (DCA, LA, KIC, butyrate, or DMKG) were capable of increasing cellular ATP levels in starved cells. Rather, when combined with starvation, such agents induced a decrease in cellular ATP, which may be attributed to autophagy inhibition, as treatment with the autophagy inhibitor 3-methyladenine (3-MA) similarly reduced ATP content and autophagy-deficient Atg5−/− or Atg7−/− mouse embryonic fibroblasts (MEFs) contained lower cellular ATP levels than WT MEFs (Lin et al., 2012b). These results suggest that an increase in cellular AcCoA levels is sufficient to counteract autophagy induction by nutrient deprivation. Moreover, pharmacological and metabolic manipulations designed to increase AcCoA were capable of suppressing autophagy induced by clinically relevant compounds, including metformin, rotenone, Akt inhibitors, and rapamycin. Thus, AcCoA acts as a broad-spectrum autophagy repressor, well beyond its capacity to inhibit starvation-induced autophagy.

AcCoA Depletion is Sufficient to Induce Autophagy

Next, we addressed the question as to whether a reduction in AcCoA levels would be sufficient to increase autophagic activity, even in cells that are kept in rich medium. Before it can be converted to AcCoA, pyruvate has to be transported across the inner mitochondrial membrane by the mitochondrial pyruvate carrier (MPC) complex (Herzig et al., 2012). Knockdown of MPC or its inhibition by UK5099 led to the depletion of intracellular AcCoA without reducing ATP. AcCoA depletion was coupled to deacetylation of cytoplasmic proteins, induction of GFP-LC3 puncta, and lipidation of endogenous LC3-I to LC3-II, both in the presence and absence of BafA1, confirming an increase of autophagic flux. UK5099 also increased the autophagy-dependent turnover of long-lived proteins. Moreover, transfection-enforced overexpression of several PDK iso forms, which catalyze the inhibitory phosphorylation of PDH, led to a reduction in both AcCoA levels (without significantly altering ATP concentration) and cytoplasmic protein acetylation, together with an increase in autophagic flux and autophagy-dependent protein degradation.

In addition to pyruvate decarboxylation, fatty acid oxidation may generate AcCoA. Inhibition of mitochondrial carnitine palmitoyltransferase-1 (CPT1), the rate-limiting enzyme in fatty acid-oxidation, by perhexiline (PHX) (Foster, 2004), reduced AcCoA cellular levels, and induced signs of autophagy. Similarly, knockdown of CPT1c, a CPT1 isoform highly expressed in human cancer cells (Zaugg et al., 2011), stimulated autophagic flux in U2OS osteosarcoma cells.

Importantly, all the interventions designed to deplete AcCoA also resulted in mTORC1 inhibition (as indicated by reduced phosphorylation of its substrate p70s6k) and AMPK stimulation yet failed to reduce intracellular ATP levels or to reduce the mitochondrial transmembrane potential. Depletion of AcCoA was not cytotoxic and actually prevented cell death induced by transgenic Q74 huntingtin (Williams et al., 2008), consistent with the reported cytoprotective action of autophagy (Rubinsztein et al., 2007). Thus, the interruption of glycolytic and lipolytic AcCoA generation in mitochondria, via inhibition of MCP or CPT1, respectively, can induce cytoprotective autophagy.

Cytosolic, not Mitochondrial Nor Nuclear, AcCoA Regulates Autophagy

AcCoA-dependent acetylation affects the function of proteins in mitochondria, as well as in other organelles including nuclei (Hebert et al., 2013, Masri et al., 2013 and Wellen et al., 2009). Cytosolic AcCoA is mostly generated from citrate, which is transported from mitochondria to the cytosol by the mitochondrial citrate carrier (CiC). Once in the cytosol, citrate is converted back to oxaloacetate and AcCoA by ATP-citrate lyase (ACLY) (Wellen et al., 2009). Based on these premises, we analyzed whether cytosolic AcCoA reduction would be sufficient to stimulate autophagic flux. Inhibition of CiC by the substrate analog 1,2,3-benzenetricarboxylate (BTC) induced the triad of AcCoA depletion (measured specifically in the cytosolic fraction), protein deacetylation, and autophagy. Similarly, either knockdown of ACLY or addition of hydroxycitrate (HC), its competitive inhibitor (Lowenstein and Brunengraber, 1981), also reduced cytoplasmic AcCoA levels, induced cytoplasmic protein deacetylation C and strongly stimulated autophagy in vitro.

Oral administration of HC to WT mice for 2 days triggered a systemic autophagic response comparable to that induced by starvation. Prolonged treatment (2 weeks) with HC is known to cause significant weight loss (Onakpoya et al., 2011), and this effect was not accompanied by reduced food intake. Surprisingly, weight reduction by HC was only observed in autophagy-competent wild-type mice, not in autophagy-deficient Atg4b−/− mice (Mariño et al., 2010).

Although cytosolic AcCoA is mostly generated from citrate via ACLY, it can also be generated from acetate by the acyl-CoA synthetase short-chain family member 2 (ACSS2) (Wellen and Thompson, 2012). Knockdown of ACSS2 induced the triad of cytosolic AcCoA depletion, protein deacetylation, and autophagy induction.

Depletion of cytosolic AcCoA by the aforementioned experimental approaches was accompanied by an increase in AMPK phosphorylation and a decrease in mTORC1-mediated p70s6k phosphorylation. Importantly, interventions designed to deplete cytosolic AcCoA (i.e., blockade of the mitochondrial citrate carrier by BTC or inhibition of ACLY by HC) abolished both the protein hyperacetylation and autophagy suppression by manipulations designed to elevate mitochondrial AcCoA levels in starved cells (i.e., addition of the PDH activator DCA, the a-ketoglutarate precursor DMKG, or the leucine derivate K1C). This supports the idea that the cytosolic (rather than the mitochondrial) pool of AcCoA modulates autophagic flux. Consistent with this notion, all treatments that increased total cellular AcCoA levels (DCA, LA, DMKG, KIC, and UK5099) also raised the cytosolic concentration of AcCoA. To directly assess the impact of cytosolic AcCoA on autophagy, starved U2OS cells stably expressing GFP-LC3 were microinjected with AcCoA. The introduction of AcCoA (but not that of CoA) into the cytosol of starved cells increased cytoplasmic protein acetylation and simultaneously reduced starvation-induced autophagic flux. This experiment provides direct evidence in favor of the idea that cytosolic AcCoA represses autophagy.

Through nuclear pores, cytosolic AcCoA can freely diffuse into the nucleus, modulate the acetylation of histone and other chromatin binding factors, and hence affect gene transcription programs (Wellen and Thompson, 2012), which in turn might impinge on autophagy. To evaluate this possibility, we experimentally enucleated GFP-LC3-expressing cells and exposed the resulting cytoplasts to AcCoA-modulating conditions in the presence of BafA1. AcCoA-depleting agents (BTC, HC, UK5099) stimulated autophagic flux in cytoplasts as efficiently as in nucleated control cells. Moreover, starvation-induced autophagy was fully induced in cytoplasts and was indistinguishably repressed by AcCoA replenishing agents in cytoplasts and cells. Thus, short-term alterations in cytosolic AcCoA concentrations can regulate autophagy through purely cytoplasmic (nonnuclear) effects.

The Acetyltransferase EP300 is Required for AcCoA-Mediated Autophagy Inhibition

Cells harbor multiple acetyltransferases and deacetylases that control the acetylation of nuclear and cytoplasmic proteins (Nakamura et al., 2010). Among the 78 acetyltransferases annotated in the human genome, we chose 43 whose localization is not strictly restricted to the nucleus. We evaluated the effects of the knockdown of these 43 acetyltransferases on the modulation of autophagic flux by AcCoA-elevating agents, as measured by the accumulation of GFP-LC3 dots in the presence of BafA1 and p62 degradation. Although the knockdown of several acetyltransferases increased autophagic flux, only that of EP300 reverted the autophagy-inhibitory effects of butyrate, DCA, KIC, LA, and DMKG. These results were confirmed by quantifying GFP-LC3 dots in the presence of BafA1 or by assessing LC3 lipidation in U2OS cells. Moreover, knockdown of EP300 decreased mTORC1 activity and abolished the activation of mTORC1 by AcCoA donors. Pharmacological inhibition of EP300 protein by c646, which competes for AcCoA binding to EP300 (Bowers et al., 2010), also induced autophagy both in vitro, in cultured cells, and in vivo, in mice. Consistently, either EP300 inhibition by c646 (in human cells) or EP300 gene deletion (in MEFs) precluded the inhibitory effect of AcCoA-replenishing agents on starvation-induced autophagy.

The activity of EP300 was highly sensitive to variations in AcCoA concentrations that are close to those observed in the cytosol of mammalian cells (Yeh and Kim, 1980). In fact, the autoacetylation of recombinant EP300 protein on K1499 (which reflects its acetyltransferase activity) (Thompson et al., 2004), as well as its capacity to acetylate other substrates (such as recombinant tumor suppressor p53 or histone H3 proteins), was influenced by AcCoA concentration in a cell-free system. Acetylation of EP300 was also reduced after the culture of cells in nutrient-free conditions, as determined by SILAC technology and confirmed by immunobloting. Starvation-induced deacetylation of the K1499 residue in EP300 could be avoided when AcCoA was replenished by addition of DCA, KIC, DMKG, or LA.

Taken together, these results indicate that EP300 is responsible for AcCoA-mediated autophagy repression and underscore the link between AcCoA concentration, EP300 activity, and autophagy regulation.

Discussion

Here we report that multiple distinct manipulations designed to increase or reduce intracellular AcCoA lead to the suppression or induction of autophagy, respectively, in mice or in cultured human cells. Thus, the inhibition of AcCoA synthesis by interventions on pyruvate, acetate, BCAAs, and fatty acid metabolism induces autophagy, while stimulation of AcCoA synthesis inhibits autophagy induced by multiple distinct stimuli.

At variance with kinases, which operate close to independently from ATP concentrations (due to their high Kd for ATP), acetyltransferases are profoundly influenced in their catalytic activity by the availability of acetyl groups, provided by AcCoA. Thus, subtle differences in AcCoA levels may impact on the level of overall protein acetylation, which reflects the compounded activity of acetyltransferases and deacetylases (Wellen and Thompson, 2012). Accordingly, AcCoA depletion was accompanied by a reduction of the acetylation of most proteins, as indicated by immunofluorescence detection of acetylated proteins or mass spectrometry. This finding is in accord with multiple reports showing that deacetylation favors autophagy. Starvation can induce the sirtuin-1-induced deacetylation of essential autophagy proteins including ATG5, ATG7, ATG12, and LC3 (Lee et al., 2008 and Lee and Finkel, 2009); the HDAC6-mediated deacetylation of cortactin (Lee et al., 2010); and the HDAC6-mediated deacetylation and activation of salt-inducible kinase 2 (SIK2), a member of the AMPK family, which is counteracted by the acetyltransferase EP300 (Yang et al., 2013). Moreover, the direct activation of deacetylases and inhibition of acetyltransferases can stimulate the induction of autophagy (Eisenberg et al., 2009 and Morselli et al., 2011). Contrasting with this general pattern, the hyperacetylation of some specific proteins has been linked to autophagy induction by starvation. This is exemplified by the proautophagic Esa1p/TIP60-mediated hyperacetylation of Atg3p in yeast (Yi et al., 2012) or the hyperacetylaton of tubulin (Geeraert et al., 2010 and Lee et al., 2010) and ULK1 in human cells (Lin et al., 2012a). Accordingly, we found that starvation led to the hyperacetylation of a few proteins, as determined by SILAC technology. Future studies must determine through which mechanisms starvation may stimulate the hyperacetylation of a few exceptional substrates in spite of a context of reduced AcCoA levels.

The depletion of energy-rich metabolites is a strong inducer of autophagy. As an example, an unfavorable shift in the ratio between ATP and AMP causes activation of AMPK, which phosphorylates multiple substrates in the cardinal autophagy regulators, including the ULK1, mTORC1, and Beclin 1 complexes (Kim et al., 2013). Moreover, depletion of NADH causes the activation of sirtuin-1 and other sirtuins with autophagy-stimulatory consequences (Jang et al., 2012). AMPK and sirtuin-1 can cooperate in autophagy induction, forming a cooperative switch for the rapid adaptation of cells to dwindling energy sources (Cantó et al., 2009 and Lan et al., 2008). Notwithstanding the importance of ATP/AMPK and NADH/sirtuin-1, our results point to the existence of an additional control instance, cytosolic AcCoA. Indeed, at early time points of starvation, intracellular AcCoA was found to be reduced well before ATP depletion or NADH oxidation became detectable.

It is possible that ATP-, NADH-, and AcCoA-regulated processes are closely interconnected, based on multiple pathways that link energy homeostasis among these molecules, as well as on the fact that AMPK phosphorylates the acetyltransferase EP300 (Yang et al., 2001) and closely cooperates with the deacetylase sirtuin-1 (Kroemer et al., 2010). Moreover, sirtuin-1 deacetylates liver kinase B1 (LKB1), increasing its capacity to phosphorylate and activate AMPK (Lan et al., 2008). In accord with this postulated interconnectivity, artificial depletion or replenishment of AcCoA was accompanied by the activation or inhibition of AMPK, as well as the mirror-like inhibition or activation of mTORC1. MEFs lacking the AMPK subunits PRKAA1 and PRKAA2 still responded to starvation and AcCoA depletion/increase by an increase/reduction in autophagic flux (Figures S6A and S6B), supporting the idea that acetylation-dependent control of autophagy can occur independently from AMPK. In contrast, our data are fully compatible with the possibility that cytosolic AcCoA depletion stimulates autophagy via the repression of mTORC1 activity. Indeed, in all experiments, cytosolic AcCoA levels negatively correlated with the phosphorylation of the mTORC1 substrate p70S6K.

Interestingly, inhibition of EP300 acetyltransferase counteracted the autophagy-suppressive action of high AcCoA. In fact, none of the AcCoA-elevating agents used in this study were able to inhibit starvation-induced autophagy in the absence of EP300 expression. Moreover, genetic or pharmacological inhibition of EP300 consistently induced autophagy in several model systems. Notwithstanding the caveat that EP300 inhibition might induce autophagy via toxic side effects, these results, together with the fact that EP300 activity is regulated by AcCoA levels, suggest that EP300 may function as an AcCoA sensor that translates elevations in intracellular AcCoA into autophagy inhibition. EP300 is known to acetylate ATG proteins, thereby interfering with their proautophagic function (Lee and Finkel, 2009). Although this seems a plausible mechanism by which high AcCoA may inhibit autophagy in an EP300-dependent fashion, additional EP300 targets may be involved in this process. Thus, EP300 inhibition prevented mTORC1 activation upon AcCoA replenishment, suggesting that EP300 inhibition might stimulate autophagy indirectly, via the suppression of mTORC1 activity. The molecular links between EP300 and mTORC1 require further in-depth investigation.

Chronic elevation of AcCoA by excessive caloric intake may suppress autophagy, thereby accelerating the manifestation of age-associated pathologies. On the other hand, dietary and pharmacological manipulations causing a decrease in AcCoA might ameliorate our health by stimulating autophagy. In this context, it appears intriguing that HC, an antiobesity agent (Onakpoya et al., 2011), enhances autophagic flux, which in turn is required for body weight reduction. In contrast, several components used to experimentally stimulate weight gain, such as DMKG or KIC (Campbell et al., 2006 and Zanchi et al., 2011), were found to suppress autophagy.

Altogether, the present data unravel a whole range of metabolic and pharmacological manipulations that, by targeting AcCoA, allow for the induction or suppression of autophagy irrespective of the nutritional status.

EXAMPLE 4

Material & Methods:

Chemicals and Culture Conditions:

Culture media and supplements for cell culture were purchased from GIBCO Invitrogen (Carlsbad) and plasticware from Corning (Corning). Human osteosarcoma U2OS cells, their GFP-LC3-expressing derivatives and human neuroblastoma H4 GFP-LC3 cells (gift from Professor J. Yuan), were cultured in DMEM medium containing 10% fetal bovine serum, 100 mg/L sodium pyruvate, 10 mM HEPES buffer, 100 units/mL penicillin G sodium, and 100 mg/mL streptomycin sulfate (37 _C, 5% CO2). Murine fibrosarcoma MCA205 cells, their GFP-LC3 expressing derivatives and shRNA transfected cells, as well as murine colorectal cancer CT26 and lung cancer TC1 cell lines, were cultured in RPMI medium containing 10% fetal bovine serum, 100 mg/L sodium pyruvate, 10 mM HEPES buffer, 100 units/mL penicillin G sodium, and 100 mg/mL streptomycin sulfate (37 _C, 5% CO2). Cells were seeded in 6-well, 96-wells or 384 well plates before treatment with 20 mM Potassium Hydroxycitrate (Sigma Aldrich), 20 mM Potassium Citrate (Sigma Aldrich), 30 µM SB 204990 (Tocris Bioscience), 30 µM BMS 303141 (Tocris Bioscience), 10 µM Simvastatin (Sigma Aldrich), 10 µM Mevastatin (Sigma Aldrich), 100 µM Mevalonolactone (Sigma Aldrich), 50 µM TOFA (Sigma Aldrich), 1 µM Sodium Salycilate (Sigma Aldrich), 3 µM C646 (Sigma Aldrich), 100 nM Bafilomycin A1 (Lc Laboratories), 2 µM Mitoxanthrone Dhydrochloride (Sigma Aldrich).

Immunoblotting

For immunoblotting, protein extracts obtained by cellular lysis via RIPA buffer were run on 4-12% Bis-Tris acrylamide (Invitrogen) and electrotransferred to 0.2 µM PVDF membranes (Biorad, USA). Unspecific binding sites were saturated by incubating membranes for 1 h in 0.05% Tween 20 (v:v in TBS) supplemented with 5% non-fat powdered milk (w:v in TBS), followed by an overnight incubation with primary antibodies specific for, LC3, phospho-AMPK (Thr172), AMPK, phosphor-ACC (Ser79), ACC, phospho-ribosomal protein S6 kinase (Thr421/Ser424), ribosomal protein S6 kinase, or SQSTM/p62 (Abnova). Membranes were opportunely cut in order to allow simultaneous detection of different molecular weight proteins. Development was performed with horseradish peroxidase (HRP)-labeled secondary antibodies (Southern Biotech, Birmingham, USA) plus the SuperSignal West Pico chemo luminescent substrate (Thermo Scientific-Pierce). An anti-glyceraldehyde-3-phosphate dehydrogenase antibody (Abcam) and anti-Actin antibody (Abcam) were used to ensure equal loading of lanes. Quantification was performed by densitometry by means of Image J software.

RNA Interference in Cell Culture:

Two different siRNA sequences targeting Acetyl CoA Carboxylase (Signal Silence AcetylCoA carboxylase, #6224, #6237) and HMG-CoA reductase (#SI00017136, #SI00017150, Qiagen) were reversed transfected by means of RNAi MAX transfection reagent.

Microinjection Experiments.

For microinjection, U2OS cells were cultured overnight on culture dishes before injection. The setup for the injection itself was as follows: 10 mM CoA or AcCoA in PBS were injected for 0.2 s under an injection pressure of 150 hPa and a compensatory pressure of 9 hPa, using a microinjector (Eppendorf, Hamburg, Germany). Before injection, cells were cultured for 2 h in the presence of 100 nM bafilomycin A1 (BafA1) in control medium and in presence of 20 mm Hydroxycitrate. One hour after injection, cells were fixed with 4% PFA and analyzed by fluorescent and automated videomicroscopy.

Immunofluorescence.

Cells were fixed with 4% PFA for 15 min at room temperature, and permeabilized with 0.1% Triton X-100 for 10 min. For cytoplasmic Acetyl Lysine staining, we proceeded as described in 35. Non-specific binding sites were blocked with 5% bovine serum albumin in PBS, followed by incubation with primary antibodies overnight at 4° C. After 1 hour incubation, appropriate Alexa-conjugated Fluorophores (Invitrogen) were used for antigen detection. Ten µM Hoechst 33342 (Molecular Probes-Invitrogen, Eugene, USA) was employed for nuclear counterstaining Fluorescence wide-field and confocal microscopyassessments were performed on an DM IRE2 microscope (Leica Microsystems, Wetzlar, Germany) equipped with a DC300F camera and with an LSM 510 microscope (Carl Zeiss, Jena, Germany), respectively.

Fluorescent Microscopy

Non-confocal images were acquired with an Axio Observer inverted fluorescence microscope (Carl Zeiss). For experiments with human cell lines, a Leica APO 63× NA 1.3 immersion objective was used, whereas for the analysis of GFP-LC3 mice tissue sections, a Leica APO 40× NA 1.15 immersion objective was employed. Zeiss Immersol® immersion oil was used for all microscopic analyses. Images were acquired with a Leica DFC 350 Fxcamera (version 1.8.0) using Leica LAS AF software and processed with Adobe Photoshop (version CS5) software.

Automated Microscopy.

U2OS and H4 cells stably expressing GFP-LC3 were seeded in 96-well or 384-well imaging plates (BD Falcon, Sparks, USA). 24 h before stimulation, ells were treated with the indicated agents for 6 hours in absence of lysososomal ATPase inhibitors and for 3 hours in presence of Bafilomycin A1. Subsequently, cells were fixed with 4% PFA and counterstained with 10 µM Hoechst 33342. Images were acquired using a BD pathway 855 automated microscope (BD Imaging Systems, San Jose, USA) equipped with a 40× objective (Olympus, Center Valley, USA) coupled to a robotized Twister II plate handler (Caliper Life Sciences, Hopkinton, USA). Images were analyzed for the detection of GFP-LC3 puncta in the cytoplasm by means of the BD Attovision software (BD Imaging Systems. Cellular regions of interest, cytoplasm and nucleus, were defined and segmented according to standard proceedings. RB 2×2 and Marr-Hildreth algorithms were employed to allow the detection of GFP LC3 puncta. Statistical analyses were conducted using the R and Prism softwares (http://www.r-project.org/).

For quantitative analyses of protein acetylation, cell surfaces were segmented intocytoplasmic and nucleic regions, and staining intensity of each individual cell was measured for statistical analysis.

Mouse Experiments and Tissue Processing.

Six weeks old female C57BL/6, Balb/c and nude athymic mice (Harlan Laboratory, Gannat, France) were bred and maintained according to both the FELASA and the Animal Experimental Inserm Ethics Committee Guidelines (project: 2012-69). Mice were housed in a temperature-controlled environment with 12 h light/dark cycles and received food and water ad libitum. For tumor growth experiments, procedures adopted are described as follows: $3 \times 10^5$ tumor cells were subcutaneously inoculated; when tumors became palpable (day −1 before chemotherapy), mice were first intraperitoneally injected with 100 mg/kg Potassium Hydroxycitrate, 10 mg/kg Acetylsalicylic Acid, 30 mg/kg SB204990, 30 mg/kg c646, 5 mg/kg Rapamycin, 25 mg/kg Resveratrol, 50 mg/kg Spermidine. At day 0, mice were intraperitoneally injected with the abovementioned compounds and with 5.17 mg/Kg Mitoxanthrone or 5 mg/kg Oxaliplatin. Tumor size was measured every two days. For starvation experiments, mice underwent 48 hour fasting followed by intreperitoneal injection of chemotherapeutics. For autophagy induction study, 6 hours after CRMs administration, mice were sacrificed and tissues were snap-frozen in liquid nitrogen after extraction and homogenized two cycles for 20 s at 5,500 rpm using Precellys 24 tissue homogenator (Bertin Technologies, Montigny-le-Bretonneux, France) in a 20 mM Tris buffer (pH 7.4) containing 150 mM NaCl, 1% Triton X-100, 10 mM EDTA and Complete® protease inhibitor cocktail (Roche Applied Science, Penzberg, Germany). Tissue extracts were then centrifuged at 12,000 g at 4° C. and supernatants were collected. Protein concentration in the supernatants was evaluated by the bicinchoninic acid technique (BCA protein assay kit, Pierce Biotechnology, Rockford, US.

MPA/DMBA Induced Mammary Tumor

Six-week-old female Balb/c mice underwent surgical implantation of slow-release MPA (Medroxyprogesterone Acetate) pellets (50 mg, 90-day release; Innovative Research of America) subcutaneously on the right flank. 200 uL of 5 mg/mL DMBA (Dimethylbenzantracene)

(Sigma Aldrich) dissolved in Corn Oil was administered by oral gavage six times during 8 weeks. Tumor formation was monitored by palpation. When tumors became palpable, mice were assigned to following groups of treatment: PBS, HCA, MTX, MTX plus HCA and the MTX plus HCA upon CD4/CD8 lymphocytes depletion. Combinatorial groups were treated as previously described, whereas for CD4/CD8 depletion, mice were intraperitoneally administrated with 500 µg of anti CD4 and CD8 antibodies the day before the onset of the treatment.

Generation of LSL-K-rasG12D;Atg5fl/fl Mice.

Atg5fl/fl mice were kindly given by Dr Noboru Mizushima. LSL-K-rasG12D;Atg5fl/fl mice were obtained as described in[7]. In all experiments, only littermate mice were used as controls. All mice were maintained according to the ethical animal licence protocol complying with the Austrian and European legislation. All experiments were approved by Bundesministerium for Wissenschaft and Forschung, Austria (BMWF-66.015/0013-II/3b/2012).

Induction of Lung Cancer.

Inhalation of 6-8-week-old mice with AdCre viruses was performed as previously reported (REF). In brief, experimental animals were anaesthetized with 10% Ketasol/Xylasol and placed on a heated pad. An AdCre-CaCl2 precipitate was produced by mixing 60 ml MEM, 2.5 ml AdCre (1010 p.f.u. ml_1; University of Iowa, Gene Transfer Vector Core Iowa, USA) and 0.6 ml CaCl2 (1 M) for each mouse and incubated for 20 min at room temperature. One week after AdCre inhalation, mice were administered with 900 mg/kg HC per body weight in drinking water for 5 weeks and tumors lesions were evaluated by immunohistochemistry.

Histology and Immunohistochemistry.

For KRas-induced lung cancers hisology, 2 mm sections from at least three different planes were cut and stained with haematoxylin and eosin. Sections were scanned using a Mirax slide scanner and lung/tumour areas were automatically scored by an algorithm programmed and executed using the Definiens software suite and visually analyzed in a double blinded fashion. Immunhistochemical staining was performed by automatic staining machine (Leica Bond3) or manually processed. Sections were dehydrated and antigenic epitopes were retrieved using a 10-mM citrate buffer and microwaving for 10 min. Specimen were then incubated with rabbit polyclonal anti-Foxp3 (eBioscience, 13-5773, :100), anti-CD3E (Santa Cruz, 101442, 1:100). Primary Ab staining was detected by peroxidase conjugated anti-rabbit IgG (DAKO, P0448, 1:500). Positive cells were counted on 20 randomly chosen tumour areas at _400 magnifications in a double blinded fashion. Quantitative analysis was performed using HistoQuest software (TissueGnostics GmbH, Vienna, Austria; http://www.tissuegnostics.com).

Real Time In Vivo Imaging of ATP Release

BALB/c mice were subcutaneously inoculated with $3\times10^5$ SCR or ATG5$^{KD}$ CT26 clones stably expressing pmeLUC probe, and tumor growth was monitored every 2 days. When tumor became palpable (about 8 days after injection), mice were divided in four experimental groups. The first one was intraperitoneally injected with 200 □l PBS and after 48 hs from the first injection, 200 □l of PBS was injected again (control group). The second one was injected the first time with 100 mg/kg hydroxycitrate in 200 □l of PBS and 48 hs later again 100 mg/kg hydroxycitrate in 200 □l of PBS. The third one was intraperitoneally injected with 100 mg/kg hydroxycitrate in 200 □l of PBS and 48 hs later with 100 mg/kg hydroxycitrate in 200 □l of PBS and 5.17 mg/Kg MTX in 200 □l di PBS. The last group were injected the first time with 200 □l of PBS and 48 hs later with 5.17 mg/Kg MTX in 200 □l di PBS. Thereafter, mice were anesthetized and imaged with Xenogen—IVIS® Lumina II (Caliper, Hopkinton, Mass., USA). D-luciferin (150 mg/kg) was intraperitoneally administered to mice 15 minutes before acquisitions, which were performed immediately before and after 48 hrs from compound injections. The regions of interest were identified around tumor sites and in vivo luminescence was identified as photons/s using the Living ImageH software (Caliper).

In Vitro Acetylation Assay.

Recombinant GST-EP300 fusion protein, corresponding to the amino acids 1066-1707(14-418, Millipore), was assessed for its acetyltransferase activity on the EP300 natural substrates recombinant histone H3 protein (M2503S, New England Biolabs). Briefly, 1 µg of EP300 HAT domain was incubated in presence of an HAT assay buffer (250 mM Tris-HCl, pH 8.0, 50% glycerol, 0.5 mM EDTA and 5 mM dithiothreitol), 1 µg of substrate protein and two different concentrations of Acetyl CoA (A2056, Sigma Aldrich) for 1 hour at 30° C. in presence of 5o uM anacardic acid, 3 uM c646 and 1 mM salycilic acid. The reaction was stopped by adding 4×SDS buffer and boiling the samples. Acetylation of substrate proteins was measured by immunoblotting using specific antibodies against H3K56 (Cell Signaling, Danvers, USA), Labeling of Vesicular ATP In Vitro MCA205 cells were loaded with 5 mM quinacrine in Krebs-Ringer solution (125 mM NaCl, 5 mM KCl, 1 mM MgSO4, 0.7 mM KH2PO4, 2 mM CaCl$_2$), 6 mM glucose and 25 mM HEPES buffer, pH 7.4) for 30 min at 37 1C. Thereafter, cells were co-stained for 10 min with 1 mg/ml propidium iodide (PI) and 10 mM Hoechst 33342 (both from Molecular Probes-Life Technologies), rinsed with Krebs-Ringer solution and analyzed by automated fluorescence microscopy.

Sample Preparation Tissues

About 50 mg of tissues for each condition were first weighted and solubilized into 1.5 mL polypropylene microcentrifuge tubes, with a proportional volume of cold lysate buffer (MeOH/Water/Chloroform, 9/1/1, −20° C.) (1 mg of tissu in 5 µl of lysate buffer). They were then homogenized two times for 20 s at 5,500 rpm using Precellys 24 tissue homogenator (Bertin Technologies, Montigny-le-Bretonneux, France), followed by a centrifugation (10 min at 15000 rmp 4° C.). Upper phase of the supernatant (150 µl) is collected and evaporated in microcentrifuge tubes at 40° C. in a pneumatically-assisted concentrator (Techne DB3). On dried extract, add 300 µl of methanol, split in two parts of 150 µl: the first one as back-up, and the second one used for the following LC-MS experimentation. After a second evaporation of the aliquots, the LC-MS dried extracts are solubilized with 300 µl of MilliQ water, centrifugate (10 min at 15000 rmp 4° C.) and aliquot in 3 microcentrifuge tubes (100 µl). Aliquot were transferred in UHPLC vials and injected into UHPLC/MS or kept at −80° C. until injection.

Plasma Preparation

A volume of 100 µl of plasma was mixed with a cold solvent mixture (acetonitrile/2-propanol/water, 3/3/2, −20° C.), into 1.5 mL polypropylene microcentrifuge tubes, vortexed and centrifugated (10 min at 15000 rmp 4° C.). Supernatant is collected and evaporated in microcentrifuge tubes at 40° C. in a pneumatically-assisted concentrator (Techne DB3). On dried extract, add 300 µl of methanol, split in two parts of 150 µl: the first one as back-up, and the second one used for the following LC-MS experimentation. After a second evaporation of the aliquots, the LC-MS dried extracts are solubilized with 300 µl of MilliQ water, centrifugate (10 min at 15000 rmp 4° C.) and aliquot in 3 microcentrifuge tubes (100 µl). Aliquot were transferred in UHPLC vials and injected into UHPLC/MS or kept at −80° C. until injection.

Untargeted Analysis of Intracellular Metabolites by Ultra-High Performance Liquid Chromatography (UHPLC) Coupled to a Quadrupole-Time of Flight (QTOF) Mass Spectrometer.

Profiling of intracellular metabolites was performed on a RRLC 1260 system (Agilent Technologies, Waldbronn, Germany) coupled to a QTOF 6520 (Agilent Technologies) equipped with an electrospray source operating in both positive and negative mode and full scan mode from 50 to 1000 Da. The gas temperature was set at 350° C. with a gas flow of 12 l/min. The capillary voltage was set at 3.5 kV, and the fragmentor at 120 V. Two reference masses were used to maintain the mass accuracy during analysis: m/z 121.050873 and m/z 922.009798 in positive mode and m/z 112.985587 and m/z 980.016375 in negative mode. 10 µL of sample were injected on a SB Aq column (100 mm×2.1 mm particle size 1.8 µm) from Agilent Technologies, protected by a guard column XDB-C18 (5 mm×2.1 mm particle size 1.8 μm) and heated at 40° C. The gradient mobile phase consisted of water with 0.2% of acetic acid (A) and acetonitrile (B). The flow rate was set to 0.3 ml/min. Initial condition is 98% phase A and 2% phase B. Molecules are then eluted using a gradient from 2% to 95% phase B in 7 min. The column was washed using 95% mobile phase B for 3 minutes and equilibrated using 2% mobile phase B for 3 min. The autosampler was kept at 4° C.

Targeted Analysis of Intracellular Metabolites by Ultra-High Performance Liquid Chromatography (UHPLC) Coupled to a Triple Quadrupole (QQQ) Mass Spectrometer.

Targeted analysis was performed on a RRLC 1260 system (Agilent Technologies, Waldbronn, Germany) coupled to a Triple Quadrupole 6410 (Agilent Technologies) equipped with an electrospray source operating in positive mode. The gas temperature was set at 350° C. with a gas flow of 12 l/min. The capillary voltage was set at 3.5 kV. 5 μL of sample were injected on a Column Zorbax Eclipse plus C18 (100 mm×2.1 mm particle size 1.8 μm) from Agilent technologies, protected by a guard column XDB-C18 (5 mm×2.1 mm particle size 1.8 μm) and heated at 40° C. The gradient mobile phase consisted of water with 0.5 mM of DBAA (A) and acetonitrile (B). The flow rate was set to 0.2 ml/min, and gradient as follow:

| time (min) | A (%) | B (%) |
|---|---|---|
| 0 | 90 | 10 |
| 4 | 90 | 10 |
| 7 | 5 | 95 |
| 10 | 5 | 95 |
| 10.25 | 90 | 10 |
| 13 | 90 | 10 |

Antibodies.

For T-cell depletion, monoclonal anti-CD8a (clone 2.43) and anti-CD4 (clone GK1.5) antibodies were injected at a dose of 500 μg in the peritoneal cavity two days before chemotherapy. Selective T-cell depletion was confirmed by flow cytometry on blood samples (data not shown). For regulatory T-cell neutralization, 10 μg of monoclonal anti-FR4 (clone 2.43) antibody were injected systemically through the retro-orbital venous sinus two days before as well as the day of chemotherapy. Depleting and neutralizing antibodies were purchased from BioXCell (West Lebanon, N.H.). For flow cytometry assays, the following monoclonal antibodies were used: anti-CD16/CD32 (clone 2.4G2, BD Biosciences) to block Fc receptors, anti-CD3-APC (clone 145-2C11, eBioscience), anti-CD8a-PE (clone 53-6.7, BD Biosciences), anti-CD4-PerCP-Cy5.5 (clone RM4-5, eBioscience) and anti-CD25-PE-Cy7 (clone PC61 5.3, eBioscience) for detecting cell surface markers and anti-Foxp3-FITC (clone FJK-16s, eBioscience) for intracellular staining.

Isolation of TILs.

Tumors were digested using Miltenyi Biotec tumor digestion kit according to manufacturer's protocol. Single cells were resuspended in RPMI 1640 and sequentially passed through 100 μm and 70 μM nylon cell strainers (BD Biosciences). Leukocytes were purified using Miltenyi Biotec magnetic beads conjugated to monoclonal anti-mouse CD45 (clone 30F11.1) according to the supplier's recommendations. Prior to staining of TIL populations for flow cytometry analysis, samples were incubated with LIVE/DEAD® Fixable Yellow Dead Cell dyes (Invitrogen) to discriminate viable cells from damaged cells.

Detection of Tumor-Infiltrated Tregs.

TILs were incubated with antibodies against CD16/CD32 before staining with fluorescent-labeled antibodies targeting T-cell surface markers. Then, cells were permeabilized and fixed with eBioscience Foxp3/Transcription Factor Staining Buffer Set and stained for intracellular Foxp3. Data were acquired using a MACSQuant flow cytometer (Miltenyi Biotec) and analyzed with FlowJo v. X PC software (Treestar, Oreg., USA). Tregs were defined as CD3+ CD4+ CD8− CD25+ Foxp3+ T-cell population.

Results:

Accumulating evidence suggests that the long-term success of antineoplastic therapies is largely determined by their capacity to reinstate anticancer immunosurveillance.[1,2] This does not only apply to so-called immunotherapies but may also hold true to conventional chemo- and radiotherapies. In particular, chemotherapies with anthracyclines or oxaliplatin can stimulate immunogenic cell death (ICD), thus converting dying tumor cells into a therapeutic vaccine that elicits a potent immune response mediated by cytotoxic T lymphocytes (CTLs) against residual tumor cells.[3] Premortem autophagy is not essential for chemotherapy-elicited cancer cell death to occur[4], but indispensable for ICD, because autophagy is required for the release of adenosine triphosphate (ATP) into the extracellular space where ATP serves as a chemotactic factor to attract antigen-presenting cells into the vicinity of dying cells[5,6]. When autophagy is inhibited, tumor cells produce immunosuppressive adenosine instead of immunostimulatory ATP, hence attracting regulatory T cells (Treg) into the tumor bed[7]. After treatment with ICD inducers, autophagy-deficient tumor cells fail to elicit a therapeutic immune response, which facilitates resistance against conventional cancer treatments[5,8]. One particularly efficient strategy for increasing therapeutic efficacy in mouse models of cancer consists in combining chemotherapy with a regimen of short-term (48 h) starvation[9]. Of note, starvation for 24-48 hours is also one of the most efficient ways to elicit autophagy in most cells of the organism[10]. Based on these premises, we investigated the hypothesis that starvation and pharmacological autophagy induction might stimulate anticancer immunosurveillance.

The biochemical effects of starvation can be mimicked by so-called caloric restriction mimetics (CRMs), which are pharmacological agents or natural compounds that reduce cellular protein acetylation, increase autophagic flux and lack cytotoxicity[11]. One compound that falls into this definition is hydroxycitrate (HC)[12], an over-the-counter weight loss agent that has been evaluated in clinical trials[13]. HC acts as a competitive inhibitor of the ATP citrate lyase (ACLY), an enzyme that generates cytosolic acetyl coenzyme A (AcCoA)[13]. HC (but not citrate) and two additional chemically unrelated ACLY inhibitors (SB-204990, BMS-303141) stimulated autophagic flux in cultured cancer cells, as indicated by the autophagy-associated conversion of LC3 I to II and the distribution of initially diffuse GFP-LC3 fusion protein to cytoplasmic puncta (FIG. 7A), even in the presence of Bafilomycin A1 (which blocks the lysosomal removal of LC3 II- or GFP-LC3-containing autophagosomes)[14]. HC-induced autophagy was suppressed by microinjection of AcCoA (FIG. 7B) but not by supplementation of mevalonate, which only suppresses statin-induced autophagy (FIG. 7D). Hydroxycitrate also reduced cytoplasmic protein acetylation, as determined by immunofluorescence staining with an antibody reacting with N-ε-acetyl lysine residues (FIG. 7C). Two intraperitoneal injections of HC on consecutive days were similarly efficient as a starvation period of 48 h (during which mice had ad libitum access to water, but not food) to induce LC3I-II conversion in mouse tissues in vivo (FIG. 7E), with a similar efficiency as well established CRMs such as spermidine, resveratrol and the E1A binding protein p300 (EP300) acetyltransferase inhibitor c646[12,15]. However, compared to 48 h starvation, HC induced a relatively mild weight loss (FIG. 7F). Starvation and a diverse array of CRMs including HC caused largely convergent changes in the metabolome in vivo, in multiple distinct organs (FIG. 7G,H).

Caloric restriction is known to reduce the growth of $KRas^{G12D}$-induced lung cancers, as induced by delivering a Cre recombinase-encoding adenovirus (Ad-Cre) into the lungs of mice bearing a Lox-Stop-Lox-KRasG12D transgene[16]. We therefore explored the effects of HC, which induced autophagy in KRas induced lung adenocarcinomas, but only if they expressed at least one normal allele of the essential autophagy gene Atg5 ($Atg5^{fl/+}$). When both alleles of Atg5 were floxed ($Atg5^{fl/fl}$), the resulting Atg5-deficient tumor cells were unable to generate LC3 dots in response to HC (data not shown). HC also reduced the number and size of Ad-Cre-induced tumor lesions in $KRas;Atg5^{fl/+}$, not in $KRas;Atg5^{fl/fl}$ mice (FIG. 8A,B). Paralleling its anticancer effects, HC reduced the density of tumor infiltration by lymphocytes expressing the Treg marker Foxp3 (FIG. 8C) with a consequent improvement in the ratio between $CD8^+$ and $Foxp3^+$ lymphocytes in $KRas;Atg5^{fl/+}$ tumors only (FIG. 8D). Depletion of Tregs by antibodies recognizing two Treg surface antigens, namely CD25 or FR4, also reduced KRas-induced oncogenesis, and this effect could not be further improved by simultaneous treatment with HC (FIG. 8E). These results are compatible with the interpretation that HC-mediated stimulation of autophagy within tumor cells causes Treg depletion, which in turn improves immunosurveillance against KRas-induced neoplasia. Indeed, HC had no positive effect on lung cancers evolving in $Rag2^{--}$ mice that are unable to mount adaptive immune responses due to the absence of T and B lymphocytes (data not shown).

Immunodeficiency also compromised the improvement of chemotherapeutic efficiency by a 48 h starvation period that precedes the systemic injection of the anthracycline mitoxanthrone (MTX). Thus, starvation plus MTX caused a protracted reduction in tumor growth, provided that the cancers evolved in immunocompetent wild type (WT) mice, not in T cell-deficient nu/nu mice (FIG. 8F). Similarly, two injections of hydroxycitrate (one day before and on the same day as chemotherapy) into ad libitum fed mice improved the therapeutic outcome of treatments with MTX (FIG. 8G) or oxaliplatin (data not shown). The combination of MTX and HC was particularly efficient in reducing the frequency of $Foxp3^+$ Tregs in tumors (FIG. 8H). Moreover, epistatic analyses revealed that Treg depletion and HC administration similarly improved tumor growth reduction by MTX, yet failed to exhibit additive effects (FIG. 8I), suggesting again that HC increases the efficacy of chemotherapy secondary to the reduction of Treg infiltration into the tumor.

Combined therapy with HC plus MTX was more efficient than monotherapy with MTX on a variety of transplantable cancers including MCA205 fibrosarcomas (FIG. 8G), TC1 lung cancers and CT26 colon carcinomas (data not shown), but only if such tumors evolved in immunocompetent, not in immunodeficient nu/nu mice (data not shown). This applies also the combination of HC plus oxaliplatin, which caused superior tumor growth reduction, but only in WT, not in nu/nu mice (data not shown). Monotherapies with MTX or HC had little effect on the growth of primary, chemical carcinogen-induced breast cancers unless they were combined (left panels in FIG. 9A,B). Again, this tumor growth-reducing and survival-extending effect was lost when the animals were rendered immunodeficient by injecting antibodies that deplete CD4 and CD8 T lymphocytes (right panels in FIG. 9A,B). Hence, the capacity of HC to improve the outcome of chemotherapy was entirely immune dependent.

The combination of HC and MTX was particularly efficient in inducing the autophagy-dependent release of ATP from cultured tumor cells in vitro (FIG. 9C). Similarly, both agents together induced a higher level of extracellular ATP accumulation (that can be measured in vivo by tethering a luciferase construct on the surface of tumor cells)[17] than either agent alone. This effect was only found for autophagy-competent tumors, not for tumors in which Atg5 had been depleted by transfection with a specific shRNA (FIG. 9E). Since the combined HC plus MTX regimen lost its therapeutic efficacy on tumors engineered to express the ecto-ATPase CD39 ([18] and data not shown), it appears that autophagy-dependent ATP release plays a decisive role in the anticancer activity of HC. Accordingly, only autophagy competent tumors (that were transfected with a scrambled control shRNA) exhibited a major therapeutic response to HC plus MTX, while cancers depleted from Atg5 or Atg7 were largely therapy-resistant (FIG. 9F). Importantly, HC could be replaced by other, chemically unrelated CRMs that act through a variety of distinct molecular mechanisms: SB-204990 (a synthetic and specific inhibitor of ACLY) (FIG. 9G), spermidine (a natural compound that inhibits several acetyltransferases including EP300) {Eisenberg, 2009, Ser. No. 19/801,973; Pietrocola, 2014, CDD} (FIG. 9H), C646 (a drug that selectively inhibits EP300),[19] (FIG. 9H) and resveratrol (a polyphenol from red wine that activates the deacetylase Sirtuin 1)[20] (data not shown). Moreover, a short treatment course (on the day before and during chemotherapy) with a clinically approved autophagy inducer, rapamycin, enhanced the therapeutic effects of anthracyclines (FIG. 9J). None of these autophagy inducers did mediate any major tumor growth reduction when administered alone, and all combination regimens (MTX+SB-204990, MTX+spermidine, MTX+C646, MTX+resveratrol, MTX+rapamycin) failed when the cellular immune system was compromised due to the nu/nu mutation (FIG. 8G, J). These results suggest that pharmacological autophagy induction may enhance the efficacy of anticancer therapies by boosting a T cell-mediated immune response.

None of the aforementioned CRMs is FDA-approved, and rapamycin (which is not a CRM stricto sensu) is used as an immunosuppressive agent to avoid the rejection of allotransplants[21]. We therefore searched for an FDA-approved alternative drug. Driven by the fact that anacardic acid (AA, also known as 6-pentadecylsalicylic acid), a salicylate derivative, is a competitive inhibitor of EP300 that triggers autophagy, {Balasubramanyam, 2003, Ser. No. 12/624,111; Pietrocola, 2014, CDD} we investigated the possibility that salicylate itself and its pro-drug, aspirin (acetylsalicylate), might induce autophagy. Indeed, salicylate increased autophagic flux in cultured cells (FIG. 10A), reduced the acetylation of cytoplasmic proteins (FIG. 10B), and inhibited the acetyltransferase activity of recombinant EP300 protein in vitro, in a cell-free system, when used at a dose of 1 mM (which is in the similar range than the dose require for direct activation of adenosine monophosphate-activated kinase, AMPK).[22] This inhibitory effect was abolished by high-dose AcCoA, suggesting that it occurs through a competitive mechanism (FIG. 10C,D). Although we have no proof that aspirin acts through EP300 inhibition or alternative mechanisms, injections of aspirin induced signs of autophagy in vivo, in various mouse organs such as heart (FIG. 10D), liver and muscle (data not shown). Aspirin also improved the anticancer activity of MTX (FIG. 10F) and oxaliplatin (data not shown). These effects depended on the active participation of the host's cellular immune system (FIG. 10F), as well as on the capacity of tumor cells to mount an autophagic response (FIG. 10G). Treatment with MTX plus aspirin caused a major depletion of regulatory T cells from the tumor bed (FIG. 10H). These findings suggest that aspirin may be used as a CRM to ameliorate immunosurveillance.

Circumstantial and epidemiological evidence indicates that overfeeding and obesity constitute negative prognostic factors with regard to the incidence, progression and therapeutic response of several human malignancies[23-25]. In contrast, caloric restriction and fasting have been related to positive therapeutic outcome, both in animal models[9,16] and in humans subjected to voluntary fasting[26] or bariatric surgery[27]. Here, we report that a 48-hour starvation period (which in mice causes a dramatic, yet recoverable weight loss of ~20%) can improve the efficacy of chemotherapy via an immune-related mechanism that involves a reduction in the intratumoral infiltration by Tregs. Starvation cycles reportedly trigger the rejuvenation of immune-relevant hematopoietic stem cells, suggesting additional immunostimulatory effects that might contribute to the improved immunosurveillance[28]. Our present data suggest that starvation can be advantageously replaced by a special diet or by natural compounds that mimic starvation with regard to the induction of metabolic alterations and autophagic responses in vivo. Autophagy occurring within the tumor cells was indeed obligatory for the efficacy of HC, likely because autophagy-deficient cells escape from natural and therapy-induced immunosurveillance as they attract Tregs into the tumor bed[5-7,29]. Similarly as HC, aspirin was found to act as an efficient autophagy inducer that triggers Treg depletion as it improves the efficacy of anticancer chemotherapy with regard to tumor growth reduction in an immune-dependent fashion. Aspirin reduces the occurrence and progression of several human cancer types[30,31], and it remains to be determined to which extent autophagy induction and immunosurveillance may contribute to its chemopreventive action beyond its well established anti-inflammatory and cell-autonomous effects.

Several among the agents that we describe here as CRMs with positive effects on anticancer immunosurveillance have a rather favorable toxicological profile. Thus, chronic treatment with aspirin, spermidine or rapamycin even extends the health and life spans of mice[32-34], suggesting that at least some CRMs might have a rather favorable risk/benefit profile. Future work will be required to understand with particular CRM (or CRMs combination) will be optimally suitable for the treatment of neoplasia.

REFERENCES

Throughout this application, various references describe the state of the art to which this invention pertains. The disclosures of these references are hereby incorporated by reference into the present disclosure.

Banreti, A., Sass, M., and Graba, Y. (2013). The emerging role of acetylation in the regulation of autophagy. Autophagy 9, 819-829.

Behrends, C., Sowa, M. E., Gygi, S. P., and Harper, J. W. (2010). Network organization of the human autophagy system. Nature 466, 68-76.

Blagoev, B., and Mann, M. (2006). Quantitative proteomics to study mitogen-activated protein kinases. Methods 40, 243-250.

Brunet, A., Sweeney, L. B., Sturgill, J. F., Chua, K. F., Greer, P. L., Lin, Y., Tran, H., Ross, S. E., Mostoslaysky, R., Cohen, H. Y., et al. (2004). Stress-dependent regulation of FOXO transcription factors by the SIRT1 deacetylase. Science 303, 2011-2015.

Campbell, B., Roberts, M., Kerksick, C., Wilborn, C., Marcello, B., Taylor, L., Nassar, E., Leutholtz, B., Bowden, R., Rasmussen, C., et al. (2006). Pharmacokinetics, safety, and effects on exercise performance of L-arginine alpha-ketoglutarate in trained adult men. Nutrition 22, 872-881.

Canto, C., Gerhart-Hines, Z., Feige, J. N., Lagouge, M., Noriega, L., Milne, J. C., Elliott, P. J., Puigserver, P., and Auwerx, J. (2009). AMPK regulates energy expenditure by modulating NAD+ metabolism and SIRT1 activity. Nature 458, 1056-1060.

Cao, D. J., Jiang, N., Blagg, A., Johnstone, J. L., Gondalia, R., Oh, M., Luo, X., Yang, K. C., Shelton, J. M., Rothermel, B. A., et al. (2013). Mechanical unloading activates FoxO3 to trigger Bnip3-dependent cardiomyocyte atrophy. Journal of the American Heart Association 2, e000016.

Choi, A. M., Ryter, S. W., and Levine, B. (2013). Autophagy in human health and disease. N Engl J Med 368, 1845-1846.

Choudhary, C., Kumar, C., Gnad, F., Nielsen, M. L., Rehman, M., Walther, T. C., Olsen, J. V., and Mann, M. (2009). Lysine acetylation targets protein complexes and co-regulates major cellular functions. Science 325, 834-840.

Chuang, D. (2013). Branched-Chain Amino Acids. In Encyclopedia of Biological Chemistry, pp. 244-249.

Contreras, G. A., Bell, C. S., Del Bianco, G. P., Perez, N., Kleinosky, M. T., Murphy, J. R., and Heresi, G. P. (2013). Prevalence and risk factors associated with resistance-associated mutations to etravirine in a cohort of perinatally HIV-infected children. The Journal of antimicrobial chemotherapy.

Cox, J., and Mann, M. (2008). MaxQuant enables high peptide identification rates, individualized p.p.b.-range mass accuracies and proteome-wide protein quantification. Nature biotechnology 26, 1367-1372.

Cox, J., Neuhauser, N., Michalski, A., Scheltema, R. A., Olsen, J. V., and Mann, M. (2011). Andromeda: a peptide search engine integrated into the MaxQuant environment. J Proteome Res 10, 1794-1805.

Crighton, D., Wilkinson, S., O'Prey, J., Syed, N., Smith, P., Harrison, P. R., Gasco, M., Garrone, O., Crook, T., and Ryan, K. M. (2006). DRAM, a p53-induced modulator of autophagy, is critical for apoptosis. Cell 126, 121-134.

Donohoe, D. R., Collins, L. B., Wali, A., Bigler, R., Sun, W., and Bultman, S. J. (2012). The Warburg effect dictates the mechanism of butyrate-mediated histone acetylation and cell proliferation. Mol Cell 48, 612-626. Eisenberg, T., Knauer, H., Schauer, A., Buttner, S., Ruckenstuhl, C., Carmona-Gutierrez, D., Ring, J., Schroeder, S., Magnes, C., Antonacci, L., et al. (2009). Induction of autophagy by spermidine promotes longevity. Nat Cell Biol 11, 1305-1314.

Fabrizio, P., Hoon, S., Shamalnasab, M., Galbani, A., Wei, M., Giaever, G., Nislow, C., and Longo, V. D. (2010). Genome-wide screen in Saccharomyces cerevisiae identifies vacuolar protein sorting, autophagy, biosynthetic, and tRNA methylation genes involved in life span regulation. PLoS Genet 6, e1001024.

Foster, D. W. (2004). The role of the carnitine system in human metabolism. Ann N Y Acad Sci 1033, 1-16.

Geeraert, C., Ratier, A., Pfisterer, S. G., Perdiz, D., Cantaloube, I., Rouault, A., Pattingre, S., Proikas-Cezanne, T., Codogno, P., and Pous, C. (2010). Starvation-induced hyperacetylation of tubulin is required for the stimulation of autophagy by nutrient deprivation. J Biol Chem 285, 24184-24194.

Guo, J. Y., Chen, H. Y., Mathew, R., Fan, J., Strohecker, A. M., Karsli-Uzunbas, G., Kamphorst, J. J., Chen, G., Lemons, J. M., Karantza, V., et al. (2011). Activated Ras requires autophagy to maintain oxidative metabolism and tumorigenesis. Genes Dev 25, 460-470.

Hamai, A., and Codogno, P. (2012). New targets for acetylation in autophagy. Science signaling 5, pe29.

Harper, A. E., Miller, R. H., and Block, K. P. (1984). Branched-chain amino acid metabolism. Annu Rev Nutr 4, 409-454.

Hassig, C. A., Fleischer, T. C., Billin, A. N., Schreiber, S. L., and Ayer, D. E. (1997). Histone deacetylase activity is required for full transcriptional repression by mSin3A. Cell 89, 341-347.

Hebert, A. S., Dittenhafer-Reed, K. E., Yu, W., Bailey, D. J., Selen, E. S., Boersma, M. D., Carson, J. J., Tonelli, M., Balloon, A. J., Higbee, A. J., et al. (2013). Calorie Restriction and SIRT3 Trigger Global Reprogramming of the Mitochondrial Protein Acetylome. Mol Cell 49, 186-199.

Herzig, S., Raemy, E., Montessuit, S., Veuthey, J. L., Zamboni, N., Westermann, B., Kunji, E. R., and Martinou, J. C. (2012). Identification and functional expression of the mitochondrial pyruvate carrier. Science 337, 93-96.

Hou, X., Xu, S., Maitland-Toolan, K. A., Sato, K., Jiang, B., Ido, Y., Lan, F., Walsh, K., Wierzbicki, M., Verbeuren, T. J., et al. (2008). SIRT1 regulates hepatocyte lipid metabolism through activating AMP-activated protein kinase. J Biol Chem 283, 20015-20026.

Husnjak, K., and Dikic, I. (2012). Ubiquitin-binding proteins: decoders of ubiquitin-mediated cellular functions. Annu Rev Biochem 81, 291-322.

Jang, S. Y., Kang, H. T., and Hwang, E. S. (2012). Nicotinamide-induced mitophagy: event mediated by high NAD+/NADH ratio and SIRT1 protein activation. J Biol Chem 287, 19304-19314.

Jeong, J. Y., Jeoung, N. H., Park, K. G., and Lee, I. K. (2012). Transcriptional regulation of pyruvate dehydrogenase kinase. Diabetes & metabolism journal 36, 328-335.

Katan-Khaykovich, Y., and Struhl, K. (2002). Dynamics of global histone acetylation and deacetylation in vivo: rapid restoration of normal histone acetylation status upon removal of activators and repressors. Genes Dev 16, 743-752.

Kennedy, J. A., Unger, S. A., and Horowitz, J. D. (1996) Inhibition of carnitine palmitoyltransferase-1 in rat heart and liver by perhexiline and amiodarone. Biochemical pharmacology 52, 273-280.

Kim, J., Kim, Y. C., Fang, C., Russell, R. C., Kim, J. H., Fan, W., Liu, R., Zhong, Q., and Guan, K. L. (2013). Differential Regulation of Distinct Vps34 Complexes by AMPK in Nutrient Stress and Autophagy. Cell 152, 290-303.

Kroemer, G., Mariño, G., and Levine, B. (2010). Autophagy and the integrated stress response. Mol Cell 40, 280-293.

Ladoire, S., Chaba, K., Martins, I., Sukkurwala, A. Q., Adjemian, S., Michaud, M., Poirier-Colame, V., Andreiuolo, F., Galluzzi, L., White, E., et al. (2012). Immunohistochemical detection of cytoplasmic LC3 puncta in human cancer specimens. Autophagy 8, 1175-1184.

Lan, F., Cacicedo, J. M., Ruderman, N., and Ido, Y. (2008). SIRT1 modulation of the acetylation status, cytosolic localization, and activity of LKB1. Possible role in AMP-activated protein kinase activation. J Biol Chem 283, 27628-27635.

Lee, I. H., Cao, L., Mostoslavsky, R., Lombard, D. B., Liu, J., Bruns, N. E., Tsokos, M., Alt, F. W., and Finkel, T. (2008). A role for the NAD-dependent deacetylase Sirt1 in the regulation of autophagy. Proc Natl Acad Sci USA 105, 3374-3379.

Lee, I. H., and Finkel, T. (2009). Regulation of autophagy by the p300 acetyltransferase. J Biol Chem 284, 6322-6328.

Lee, J. Y., Koga, H., Kawaguchi, Y., Tang, W., Wong, E., Gao, Y. S., Pandey, U. B., Kaushik, S., Tresse, E., Lu, J., et al. (2010). HDAC6 controls autophagosome maturation essential for ubiquitin-selective quality-control autophagy. Embo J 29, 969-980.

Lee, C., Raffaghello, L., Brandhorst, S., Safdie, F. M., Bianchi, G., Martin-Montalvo, A., Pistoia, V., Wei, M., Hwang, S., Merlino, A., et al. (2012). Fasting cycles retard growth of tumors and sensitize a range of cancer cell types to chemotherapy. Science translational medicine 4, 124ra127.

Levine, B., and Kroemer, G. (2008). Autophagy in the pathogenesis of disease. Cell 132, 27-42.

Lin, S. Y., Li, T. Y., Liu, Q., Zhang, C., Li, X., Chen, Y., Zhang, S. M., Lian, G., Liu, Q., Ruan, K., et al. (2012a). GSK3-TIP60-ULK1 signaling pathway links growth factor deprivation to autophagy. Science 336, 477-481.

Lin, T. C., Chen, Y. R., Kensicki, E., Li, A. Y., Kong, M., Li, Y., Mohney, R. P., Shen, H. M., Stiles, B., Mizushima, N., et al. (2012b). Autophagy: resetting glutamine-dependent metabolism and oxygen consumption. Autophagy 8, 1477-1493.

Lin, Y. Y., Kiihl, S., Suhail, Y., Liu, S. Y., Chou, Y. H., Kuang, Z., Lu, J. Y., Khor, C. N., Lin, C. L., Bader, J. S., et al. (2012c). Functional dissection of lysine deacetylases reveals that HDAC1 and p300 regulate AMPK. Nature 482, 251-255.

Löpez-Otin, C. B., M. A.; Partridge, L.; Serrano, M.; Kroemer, G.; (2013). The Hallmarks of Aging Cell 153, 1194-1217.

Lowenstein, J. M., and Brunengraber, H. (1981). Hydroxycitrate. Methods Enzymol 72, 486-497.

Mariño, G., Fernandez, A. F., Cabrera, S., Lundberg, Y. W., Cabanillas, R., Rodriguez, F., Salvador-Montoliu, N., Vega, J. A., Germana, A., Fueyo, A., et al. (2010). Autophagy is essential for mouse sense of balance. J Clin Invest 120, 2331-2344.

Mariño, G., Madeo, F., and Kroemer, G. (2011). Autophagy for tissue homeostasis and neuroprotection. Curr Opin Cell Biol 23, 198-206.

Masri, S., Patel, V. R., Eckel-Mahan, K. L., Peleg, S., Forne, I., Ladurner, A. G., Baldi, P., Imhof, A., and Sassone-Corsi, P. (2013). Circadian acetylome reveals regulation of mitochondrial metabolic pathways. Proc Natl Acad Sci USA.

Mizushima, N., and Komatsu, M. (2011). Autophagy: renovation of cells and tissues. Cell 147, 728-741.

Mizushima, N., Yamamoto, A., Matsui, M., Yoshimori, T., and Ohsumi, Y. (2004). In vivo analysis of autophagy in response to nutrient starvation using transgenic mice expressing a fluorescent autophagosome marker. Mol Biol Cell 15, 1101-1111.

Morselli, E., Mariño, G., Bennetzen, M. V., Eisenberg, T., Megalou, E., Schroeder, S., Cabrera, S., Benit, P., Rustin, P., Criollo, A., et al. (2011). Spermidine and resveratrol induce autophagy by distinct pathways converging on the acetylproteome. J Cell Biol 192, 615-629.

Nakamura, A., Kawakami, K., Kametani, F., Nakamoto, H., and Goto, S. (2010). Biological significance of protein modifications in aging and calorie restriction. Ann N Y Acad Sci 1197, 33-39.

Navarro, D., Zwingmann, C., and Butterworth, R. F. (2008). Impaired oxidation of branched-chain amino acids in the medial thalamus of thiamine-deficient rats. Metabolic brain disease 23, 445-455.

Onakpoya, I., Hung, S. K., Perry, R., Wider, B., and Ernst, E. (2011). The Use of Garcinia Extract (Hydroxycitric Acid) as a Weight loss Supplement: A Systematic Review and Meta-Analysis of Randomised Clinical Trials. Journal of obesity 2011, 509038.

Pankiv, S., Clausen, T. H., Lamark, T., Brech, A., Bruun, J. A., Outzen, H., Overvatn, A., Bjorkoy, G., and Johansen, T. (2007). p62/SQSTM1 binds directly to Atg8/LC3 to facilitate degradation of ubiquitinated protein aggregates by autophagy. J Biol Chem 282, 24131-24145.

Pehar, M., Jonas, M. C., Hare, T. M., and Puglielli, L. (2012). SLC33A1/AT-1 protein regulates the induction of autophagy downstream of IRE1/XBP1 pathway. J Biol Chem 287, 29921-29930.

Pietrocola, F., Izzo, V., Niso-Santano, M., Vacchelli, E., Galluzzi, L., Maiuri, M. C., and Kroemer, G. (2013). Regulation of autophagy by stress-responsive transcription factors. Seminars in cancer biology.

Pictrocola, F., Mariño, G., Lissa, D., Vacchelli, E., Malik, S. A., Niso-Santano, M., Zamzami, N., Galluzzi, L., Maiuri, M. C., and Kroemer, G. (2012). Pro-autophagic polyphenols reduce the acetylation of cytoplasmic proteins. Cell Cycle 11, 3851-3860.

Rabinowitz, J. D., and White, E. (2010). Autophagy and metabolism. Science 330, 1344-1348.

Rappsilber, J., and Mann, M. (2007). Analysis of the topology of protein complexes using cross-linking and mass spectrometry. CSH protocols 2007, pdb prot4594.

Roche, T. E., and Hiromasa, Y. (2007). Pyruvate dehydrogenase kinase regulatory mechanisms and inhibition in treating diabetes, heart ischemia, and cancer. Cell Mol Life Sci 64, 830-849.

Rubinsztein, D. C., Cuervo, A. M., Ravikumar, B., Sarkar, S., Korolchuk, V., Kaushik, S., and Klionsky, D. J. (2009). In search of an "autophagomometer". Autophagy 5, 585-589.

Rubinsztein, D. C., Gestwicki, J. E., Murphy, L. O., and Klionsky, D. J. (2007). Potential therapeutic applications of autophagy. Nat Rev Drug Discov 6, 304-312.

Rubinsztein, D. C., Mariño, G., and Kroemer, G. (2011). Autophagy and aging. Cell 146, 682-695.

Ruderman, N. B., Xu, X. J., Nelson, L., Caciccdo, J. M., Saha, A. K., Lan, F., and Ido, Y. (2010). AMPK and SIRT1: a long-standing partnership? Am J Physiol Endocrinol Metab 298, E751-760.

Settembre, C., Di Malta, C., Polito, V. A., Garcia Arencibia, M., Vetrini, F., Erdin, S., Erdin, S. U., Huynh, T., Medina, D., Colella, P., et al. (2011). TFEB links autophagy to lysosomal biogenesis. Science 332, 1429-1433.

Shi, C. S., and Kehrl, J. H. (2010). TRAF6 and A20 regulate lysine 63-linked ubiquitination of Beclin-1 to control TLR4-induced autophagy. Science signaling 3, ra42.

Shi, L., and Tu, B. P. (2013). Acetyl-CoA induces transcription of the key G1 cyclin CLN3 to promote entry into the cell division cycle in *Saccharomyces cerevisiae*. Proc Natl Acad Sci USA 110, 7318-7323.

Takahashi, H., McCaffery, J. M., Irizarry, R. A., and Boeke, J. D. (2006). Nucleocytosolic acetyl-coenzyme a synthetase is required for histone acetylation and global transcription. Mol Cell 23, 207-217.

Tasdemir, E., Maiuri, M. C., Galluzzi, L., Vitale, I., Djavaheri-Mergny, M., D'Amelio, M., Criollo, A., Morselli, E., Zhu, C., Harper, F., et al. (2008). Regulation of autophagy by cytoplasmic p53. Nat Cell Biol 10, 676-687.

Tsonev, L. I., and Hirsh, A. G. (2008). Theory and applications of a novel ion exchange chromatographic technology using controlled pH gradients for separating proteins on anionic and cationic stationary phases. Journal of chromatography A 1200, 166-182.

Warr, M. R., Binnewies, M., Flach, J., Reynaud, D., Garg, T., Malhotra, R., Debnath, J., and Passegue, E. (2013). FOXO3A directs a protective autophagy program in haematopoietic stem cells. Nature 494, 323-327.

Watson, J. A., Fang, M., and Lowenstein, J. M. (1969). Tricarballylate and hydroxycitrate: substrate and inhibitor of ATP: citrate oxaloacetate lyase. Archives of biochemistry and biophysics 135, 209-217.

Wellen, K. E., Hatzivassiliou, G., Sachdeva, U. M., Bui, T. V., Cross, J. R., and Thompson, C. B. (2009). ATP-citrate lyase links cellular metabolism to histone acetylation. Science 324, 1076-1080.

Wellen, K. E., and Thompson, C. B. (2012). A two-way street: reciprocal regulation of metabolism and signalling. Nat Rev Mol Cell Biol 13, 270-276.

Willenborg, M., Panten, U., and Rustenbeck, I. (2009). Triggering and amplification of insulin secretion by dimethyl alpha-ketoglutarate, a membrane permeable alpha-ketoglutarate analogue. Eur J Pharmacol 607, 41-46.

Williams, A., Sarkar, S., Cuddon, P., Ttofi, E. K., Saiki, S., Siddiqi, F. H., Jahreiss, L., Fleming, A., Pask, D., Goldsmith, P., et al. (2008). Novel targets for Huntington's disease in an mTOR-independent autophagy pathway. Nat Chem Biol 4, 295-305.

Yang, W., Hong, Y. H., Shen, X. Q., Frankowski, C., Camp, H. S., and Leff, T. (2001). Regulation of transcription by AMP-activated protein kinase: phosphorylation of p300 blocks its interaction with nuclear receptors. J Biol Chem 276, 38341-38344.

Yi, C., Ma, M., Ran, L., Zheng, J., Tong, J., Zhu, J., Ma, C., Sun, Y., Zhang, S., Feng, W., et al. (2012). Function and molecular mechanism of acetylation in autophagy regulation. Science 336, 474-477.

Zachar, Z., Marecek, J., Maturo, C., Gupta, S., Stuart, S. D., Howell, K., Schauble, A., Lem, J., Piramzadian, A., Karnik, S., et al. (2011). Non-redox-active lipoate derivates disrupt cancer cell mitochondrial metabolism and are potent anticancer agents in vivo. J Mol Med (Berl) 89, 1137-1148.

Zanchi, N. E., Gerlinger-Romero, F., Guimaraes-Ferreira, L., de Siqueira Filho, M. A., Felitti, V., Lira, F. S., Seelaender, M., and Lancha, A. H., Jr. (2011). HMB supplementation: clinical and athletic performance-related effects and mechanisms of action. Amino acids 40, 1015-1025.

Zaugg, K., Yao, Y., Reilly, P. T., Kannan, K., Kiarash, R., Mason, J., Huang, P., Sawyer, S. K., Fuerth, B., Faubert, B., et al. (2011). Carnitine palmitoyltransferase 1C promotes cell survival and tumor growth under conditions of metabolic stress. Genes Dev 25, 1041-1051.

Zhu, H., Tannous, P., Johnstone, J. L., Kong, Y., Shelton, J. M., Richardson, J. A., Le, V., Levine, B., Rothermel, B.

A., and Hill, J. A. (2007). Cardiac autophagy is a maladaptive response to hemodynamic stress. J Clin Invest 117, 1782-1793.
1. Loi S, Sirtaine N, Piette F, Salgado R, Viale G, Van Eenoo F, et al. Prognostic and predictive value of tumor-infiltrating lymphocytes in a phase III randomized adjuvant breast cancer trial in node-positive breast cancer comparing the addition of docetaxel to doxorubicin with doxorubicin-based chemotherapy: BIG 02-98. J Clin Oncol 2013; 31:860-7;
2. Zitvogel L, Galluzzi L, Smyth M J, Kroemer G. Mechanism of action of conventional and targeted anticancer therapies: reinstating immunosurveillance. Immunity 2013; 39:74-88;
3. Kepp O, Senovilla L, Kroemer G. Immunogenic cell death inducers as anticancer agents. Oncotarget 2014; 5:5190-1;
4. Guo J Y, Xia B, White E. Autophagy-mediated tumor promotion. Cell 2013; 155:1216-9;
5. Michaud M, Martins I, Sukkurwala A Q, Adjemian S, Ma Y, Pellegatti P, et al. Autophagy-dependent anticancer immune responses induced by chemotherapeutic agents in mice. Science 2011; 334:1573-7;
6. Ma Y, Adjemian S, Mattarollo S R, Yamazaki T, Aymeric L, Yang H, et al. Anticancer chemotherapy-induced intratumoral recruitment and differentiation of antigen-presenting cells. Immunity 2013; 38:729-41;
7. Rao S, Tortola L, Perlot T, Wirnsberger G, Novatchkova M, Nitsch R, et al. A dual role for autophagy in a murine model of lung cancer. Nat Commun 2014; 5:3056;
8. Ko A, Kanehisa A, Martins I, Senovilla L, Chargari C, Dugue D, et al. Autophagy inhibition radiosensitizes in vitro, yet reduces radioresponses in vivo due to deficient immunogenic signalling. Cell Death Differ 2014; 21:92-9;
9. Lee C, Raffaghello L, Brandhorst S, Safdie F M, Bianchi G, Martin-Montalvo A, et al. Fasting cycles retard growth of tumors and sensitize a range of cancer cell types to chemotherapy. Sci Transl Med 2012; 4:124ra27;
10. Mizushima N, Yamamoto A, Matsui M, Yoshimori T, Ohsumi Y. In vivo analysis of autophagy in response to nutrient starvation using transgenic mice expressing a fluorescent autophagosome marker. Mol Biol Cell 2004; 15:1101-11;
11. Madeo F, Pietrocola F, Eisenberg T, Kroemer G. Caloric restriction mimetics: towards a molecular definition. Nat Rev Drug Discov 2014
12. Mariño G, Pietrocola F, Eisenberg T, Kong Y, Malik S A, Andryushkova A, et al. Regulation of autophagy by cytosolic acetyl-coenzyme A. Mol Cell 2014; 53:710-25;
13. Onakpoya I, Hung S K, Perry R, Wider B, Ernst E. The Use of Garcinia Extract (Hydroxycitric Acid) as a Weight loss Supplement: A Systematic Review and Meta-Analysis of Randomised Clinical Trials. J Obes 2011; 2011: 509038;
14. Klionsky D J, Abdalla F C, Abeliovich H, Abraham R T, Acevedo-Arozena A, Adeli K, et al. Guidelines for the use and interpretation of assays for monitoring autophagy. Autophagy 2012; 8:445-544;
15. Morselli E, Mariño G, Bennetzen M V, Eisenberg T, Megalou E, Schroeder S, et al. Spermidine and resveratrol induce autophagy by distinct pathways converging on the acetylproteome. J Cell Biol 2011; 192:615-29;
16. Kalaany N Y, Sabatini D M. Tumours with PI3K activation are resistant to dietary restriction. Nature 2009; 458:725-31;
17. Pellegatti P, Raffaghello L, Bianchi G, Piccardi F, Pistoia V, Di Virgilio F. Increased level of extracellular ATP at tumor sites: in vivo imaging with plasma membrane luciferase. PLoS One 2008; 3:e2599;
18. Michaud M, Sukkurwala A Q, Martins I, Shen S, Zitvogel L, Kroemer G. Subversion of the chemotherapy-induced anticancer immune response by the ecto-ATPase CD39. Oncoimmunology 2012; 1:393-5;
19. Bowers E M, Yan G, Mukherjee C, Orry A, Wang L, Holbert M A, et al. Virtual ligand screening of the p300/CBP histone acetyltransferase: identification of a selective small molecule inhibitor. Chem Biol 2010; 17:471-82;
20. Sinclair D A, Guarente L. Small-molecule allosteric activators of sirtuins. Annu Rev Pharmacol Toxicol 2014; 54:363-80;
21. Touzot M, Soulillou J P, Dantal J. Mechanistic target of rapamycin inhibitors in solid organ transplantation: from benchside to clinical use. Curr Opin Organ Transplant 2012; 17:626-33;
22. Hawley S A, Fullerton M D, Ross F A, Schertzer J D, Chevtzoff C, Walker K J, et al. The ancient drug salicylate directly activates AMP-activated protein kinase. Science 2012; 336:918-22;
23. Gilbert C A, Slingerland J M. Cytokines, obesity, and cancer: new insights on mechanisms linking obesity to cancer risk and progression. Annu Rev Med 2013; 64:45-57;
24. Makarem N, Chandran U, Bandera E V, Parekh N. Dietary fat in breast cancer survival. Annu Rev Nutr 2013; 33:319-48;
25. Casagrande D S, Rosa D D, Umpierre D, Sarmento R A, Rodrigues C G, Schaan B D. Incidence of cancer following bariatric surgery: systematic review and meta-analysis. Obes Surg 2014; 24:1499-509;
26. Lee C, Longo V D. Fasting vs dietary restriction in cellular protection and cancer treatment: from model organisms to patients. Oncogene 2011; 30:3305-16;
27. Tee M C, Cao Y, Warnock G L, Hu F B, Chavarro J E. Effect of bariatric surgery on oncologic outcomes: a systematic review and meta-analysis. Surg Endosc 2013; 27:4449-56;
28. Cheng C W, Adams G B, Perin L, Wei M, Zhou X, Lam B S, et al. Prolonged fasting reduces IGF-1/PKA to promote hematopoietic-stem-cell-based regeneration and reverse immunosuppression. Cell Stem Cell 2014; 14:810-23;
29. Uhl M, Kepp O, Jusforgues-Saklani H, Vicencio J M, Kroemer G, Albert M L. Autophagy within the antigen donor cell facilitates efficient antigen cross-priming of virus-specific CD8+ T cells. Cell Death Differ 2009; 16:991-1005;
30. Rothwell P M, Wilson M, Price J F, Belch J F, Meade T W, Mehta Z. Effect of daily aspirin on risk of cancer metastasis: a study of incident cancers during randomised controlled trials. Lancet 2012; 379:1591-601;
31. Li P, Wu H, Zhang H, Shi Y, Xu J, Ye Y, et al. Aspirin use after diagnosis but not prediagnosis improves established colorectal cancer survival: a meta-analysis. Gut 2014
32. Strong R, Miller R A, Astle C M, Floyd R A, Flurkey K, Hensley K L, et al. Nordihydroguaiaretic acid and aspirin increase lifespan of genetically heterogeneous male mice. Aging Cell 2008; 7:641-50;
33. Harrison D E, Strong R, Sharp Z D, Nelson J F, Astle C M, Flurkey K, et al. Rapamycin fed late in life extends lifespan in genetically heterogeneous mice. Nature 2009; 460:392-5;

34. Kibe R, Kurihara S, Sakai Y, Suzuki H, Ooga T, Sawaki E, et al. Upregulation of colonic luminal polyamines produced by intestinal microbiota delays senescence in mice. Sci Rep 2014; 4:4548;

35. Pietrocola F, Mariño G, Lissa D, Vacchelli E, Malik S A, Niso-Santano M, et al. Pro-autophagic polyphenols reduce the acetylation of cytoplasmic proteins. Cell Cycle 2012; 11:3851-60;

The invention claimed is:

1. A method of treating cancer in a subject in need thereof, comprising administering to the subject at least one acetyl CoA (AcCoA) depleting agent and at least one chemotherapeutic agent, wherein the at least one AcCoA depleting agent is hydroxycitrate, wherein the at least one chemotherapeutic agent is a chemotherapeutic agent inducing immunogenic cell death (ICD), and wherein the method does not comprise administering an AcCoA-replenishing agent selected from the group consisting of dichloroacetate, lipoic acid, ketoisocaproic acid, butyrate, and dimethyl-α-ketoglutarate.

2. The method according to claim 1, wherein the chemotherapeutic agent is selected from the group consisting of epirubicin, idarubicin, mitoxantrone, paclitaxel, docetaxel, dolastatin, pancratistatin, mechlorethamine, mechlorethamine oxide hydrochloride, dactinomycin, thioguanine, an epothilone, maytansinoids, 6-thioguanine, oxaliplatin, carboplatin, vinblastine, vincristine, vinorelbine, novantrone, retinoids, irinotecan, camptothecin, topotecan, bryostatin, callystatin, CC-1065, adozelesin, carzelesin, bizelesin, spongistatin, ifosfamide, trofosfamide, fotemustine, enediyne antibiotics, hydroxyurea, dideoxyuridine, aldophosphamide glycoside, amsacrine, diaziquone, lentinan, mitoguazone, pentostatin, pirarubicin, losoxantrone, rhizoxin, dacarbazine, thiotepa, teniposide, ibandronate, denopterin, pteropterin, trimetrexate, PSK polysaccharide complex, neocarzinostatin chromophore, chromoprotein enediyne antibiotic chromophores, aclacinomysins, actinomycin, authrarnycin, azaserine, cactinomycin, carabicin, caminomycin, carzinophilin, chromomycin, dactinomycin, detorubicin, 6-diazo-5-oxo-L-norleucine, esorubicin, marcellomycin, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin, and pharmaceutically acceptable salts, acids or derivatives thereof.

3. The method according to claim 1, wherein the cancer is selected from the group consisting of cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, and uterus.

4. The method according to claim 1, wherein the cancer is selected from the group consisting of malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous; adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; Sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

5. The method according to claim 1, wherein the cancer is a KRAS mutated cancer.

6. The method according to claim 5, wherein the KRAS mutation is selected from the group consisting of G12C, G12D, G13D, G12R, G12S, and G12V.

7. The method according to claim 1, wherein the cancer is an autophagy competent cancer.

8. The method according to claim 1, wherein the AcCoA depleting agent is administered prior to the chemotherapeutic agent.

9. The method according to claim 1, wherein the AcCoA depleting agent is administered 12; 13; 14; 15; 16; 17; 18; 19; 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; 50; 51; 52; 53; 54; 55; or 56 h before the administration of the chemotherapeutic agent.

10. The method according to claim 1, wherein the AcCoA depleting agent is administered in combination with a chemotherapeutic agent.

11. A composition for treating cancer, comprising a therapeutically effective amount of an AcCoA depleting agent and a therapeutically effective amount of a chemotherapeutic agent, wherein the AcCoA depleting agent is hydroxycitrate, wherein the chemotherapeutic agent is a chemotherapeutic agent inducing immunogenic cell death (ICD), and wherein the composition for treating cancer does not comprise an AcCoA-replenishing agent selected from the group consisting of dichloroacetate, lipoic acid, ketoisocaproic acid, butyrate, and dimethyl-α-ketoglutarate.

12. The composition according to claim 11, wherein the chemotherapeutic agent is selected from the group consisting of epirubicin, idarubicin, mitoxantrone, paclitaxel, docetaxel, dolastatin, pancratistatin, mechlorethamine, mechlorethamine oxide hydrochloride, dactinomycin, thioguanine, an epothilone, maytansinoids, 6-thioguanine, oxaliplatin, carboplatin, vinblastine, vincristine, vinorelbine, novantrone, retinoids, irinotecan, camptothecin, topotecan, bryostatin, callystatin, CC-1065, adozelesin, carzelesin, bizelesin, spongistatin, ifosfamide, trofosfamide, fotemustine, enediyne antibiotics, hydroxyurea, dideoxyuridine, aldophosphamide glycoside, amsacrine, diaziquone, lentinan, mitoguazone, pentostatin, pirarubicin, losoxantrone, rhizoxin, dacarbazine, thiotepa, teniposide, ibandronate, denopterin, pteropterin, trimetrexate, PSK polysaccharide complex, neocarzinostatin chromophore, chromoprotein enediyne antibiotic chromophores, aclacinomysins, actinomycin, authrarnycin, azaserine, cactinomycin, carabicin, caminomycin, carzinophilin, chromomycin, dactinomycin, detorubicin, 6-diazo-5-oxo-L-norleucine, esorubicin, marcellomycin, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin, and pharmaceutically acceptable salts, acids or derivatives thereof.

* * * * *